US006818750B2

(12) United States Patent
Reed

(10) Patent No.: US 6,818,750 B2
(45) Date of Patent: Nov. 16, 2004

(54) CARD PROTEINS INVOLVED IN CELL DEATH REGULATION

(75) Inventor: John C. Reed, Rancho Santa Fe, CA (US)

(73) Assignee: The Burnham Institute, La Jolla, CA (US)

(*) Notice: Subject to any disclaimer, the term of this patent is extended or adjusted under 35 U.S.C. 154(b) by 77 days.

(21) Appl. No.: 09/388,221

(22) Filed: Sep. 1, 1999

(65) Prior Publication Data

US 2002/0192643 A1 Dec. 19, 2002

(51) Int. Cl.⁷ .................. C07H 21/04; C12N 15/00; C12N 15/63; C12N 15/74; C12N 5/00

(52) U.S. Cl. ............... 536/23.1; 536/23.5; 536/24.3; 435/6; 435/69.1; 435/320.1; 435/325; 435/455

(58) Field of Search ...................... 536/23.1, 23.5, 536/24.3; 435/325, 69.1, 6, 455, 320.1

(56) References Cited

FOREIGN PATENT DOCUMENTS

| WO | WO 96/12016 | 4/1996 |
|----|-------------|--------|
| WO | WO 99/40102 | 8/1999 |
| WO | WO 01/00826 | 1/2001 |
| WO | WO 01/18042 | 3/2001 |
| WO | WO 01/30971 | 5/2001 |
| WO | WO 01/66690 | 9/2001 |
| WO | WO 01/72822 | 10/2001 |

OTHER PUBLICATIONS

Ding, et al, 2000, Journal of Experimental Medicine, vol. 191, No. 2, pp. 213–223.*
Eck, et al., 1996, In Goodmand & Gilman's the Pharmacological Basis of Therapeutics, ninth edition. McGrwy–Hill, New York, pp. 77–101.*
Nagase et al. (1998) DNA Res. vol. 5, 277–286, 1998.*
Russell et al. (1994) vol. 244, 332–350, 1994.*
Gerhold et al. (1996) BioEssays, vol. 18(12), 973–981, 1996.*
Wells et al. (1997) J. Leuk. Biol., vol. 61, 545–550, 1997.*
Verma et al. (1997) Nature, vol. 389, 239–242, 1997.*
Nagase et al. (1999) DNA Res. vol. 6, 63–70, 1999.*
Marshall et al. (1995) Science, vol. 269, 1050–1055, 1995.*
Orkin et al. (1995) "Report and Recommendations.of the Panel to Assess the NIH . . . ", 1995.*
Ahmad et al., "CRADD, a novel human apoptotic adaptor molecule for caspase–2, and FasL/tumor necrosis factor receptor–interacting protein RIP" *Cancer Res.*, 57:615–619 (1997).
Bertin et al., "Human CARD4 protein is a novel CED–4/Apaf–1 cell death family member that activates NF–κB*" *J. Biol. Chem.*, 274:12955–12958.
Cardone et al., "Regulation of cell death protease caspase–9 by phosphorylation" *Science*, 282:1318–1321 (1998).

Chinnaiyan et al., "Role of CED–4 in the activation of CED–3" *Nature*, 388:728–729 (1997).
Chinnaiyan et al., "Interaction of CED–4 with CED–3 and CED–9: a molecular framework for cell death" *Science*, 275:1122–1126 (1997).
DiDonato et al., "A cytokine–responsive IκB kinase that activates the transcription factor NF–κB" *Nature*, 388:548–554 (1997).
Durfee et al., "The retinoblastoma protein associates with the protein phosphatase type 1 catalytic subunit" *Genes & Dev.*, 7:555–569 (1993).
Gene/protein characteristic table for KIAA0955, http://zearth.kazusa.or.jp/huge/gfpage/KIAA0955/ as of Aug. 11, 1999 (also see gene bank accession AB023172).
Gene/protein characteristic table for KIAA0926, http://zearth.kazusa.or.jp/huge/gfpage/KIAA0926/ as of Aug. 11, 1999 (also see gene bank accession AB023143).
Gyuris et al., "Cdi1, a human G1 and S phase protein phosphatase that associates with Cdk2" *Cell*, 75:791–803 (1993).
Hofmann et al., "The CARD domain: a new apoptotic signalling motif" *Trends Biochem. Sci.*, 22:155–156 (1997).
Inohara et al., "Nod1, an Apaf–1–like activator of caspase–9 and nuclear factor–κB*" *J. Biol. Chem.*, 274: 14560–14567 (1999).
Irmler et al., "Direct physical interaction between the *caenorhabditis elegans* 'death proteins' CED–3 and CED–4" *FEBS Letters*, 406:189–190 (1997).
Krajewski et al., "Release of caspase–9 from mitochondria during neuronal apoptosis and cerebral ischemia" *Proc. Natl. Acad. Sci. USA*, 96:5752–5757 (1999).
Li et al., "Cytochrome c and dATP–dependent formation of Apaf–1/caspase–9 complex initiates an apoptotic protease cascade" *Cell*, 91:479–489 (1997).
Nagase et al., "Prediction of the coding sequences of unidentified human genes. XIII. the complete sequences of 100 new cDNA clones from brain which code for large proteins in vitro" *DNA Research*, 6:63–70 (1999).

(List continued on next page.)

Primary Examiner—Anne Marie S. Wehbé
(74) Attorney, Agent, or Firm—McDermott Will & Emery

(57) ABSTRACT

The present invention provides NB-ARC and CARD-containing proteins (NACs), nucleic acid molecules encoding NACs and antibodies specific for at least one NAC. The invention further provides chimeric NAC proteins. The invention also provides screening assays for identifying an agent that can effectively alter the association of a NAC with a NAC-associated protein. The invention further provides methods of modulating apoptosis in a cell by introducing into the cell a nucleic acid molecule encoding a NAC or an antisense nucleotide sequence. The invention also provides a method of using a reagent that can specifically bind to a NAC to diagnose a pathology that is characterized by an increased or decreased level of apoptosis in a cell.

44 Claims, 9 Drawing Sheets

OTHER PUBLICATIONS

Qin et al., "Structural basis of procaspase–9 recruitment by the apoptotic protease–activating factor 1" *Nature*, 399:549–557 (1999).

Rothe et al., "The TNFR2–TRAF signaling complex contains two novel proteins related to baculoviral inhibitor of apoptosis proteins" *Cell*, 83:1243–1252 (1995).

Saleh et al., "Cytochrome c and dATP–mediated oligomerization of Apaf–1 is a prerequisite for procaspase–9 activation" *J. Biol. Chem.*, 274:17941–17945 (1999).

Sato et al., "Cloning and sequencing of a cDNA encoding the rat Bcl–2 protein" *Gene*, 140:291–292 (1994).

Seshagiri and Miller "Caenorhabditis elegans CED–4 stimulates CED–3 processing and CED–3–induced apoptosis" *Curr. Biol.*, 7:455–460 (1997).

Shaham and Horvitz, "An alternatively spliced *C. elegans* CED–4 RNA encodes a novel cell death inhibitor" *Cell*, 86:201–208 (1996).

Spector et al, "Interaction between the *C. elegans* cell–death regulators CED–9 and CED–4" *Nature* 385:653–656 (1997).

Srinivasula et al., "Autoactivation of procaspase–9 by Apaf–1–mediated oligomerization" *Molecular Cell*, 1:949–957 (1998).

Thome et al., "Identification of CARDIAK, a RIP–like kinase that associates with caspase–1", *Curr. Biol.*, 8:885–888 (1998).

Thornberry and Lazebnik, "Caspases:enemies within" *Science*, 281:1312–1316 (1998).

van der Biezen and Jones, "The NB–ARC domain: a novel signalling motif shared by plant resistance gene products and regulators of cell death in animals" *Curr. Biol.*, 8:R226–R227 (1998).

Willis et al., "Bc 10 is involved in t(1;14) (p22;q32) of MALT B cell lymphoma and mutated in multiple tumor types" *Cell*, 96:35–45 (1999).

Wu et al., "Interaction and regulation of subcellular localization of CED–4 by CED–9" *Science*, 275:1126–1129 (1997).

Yang et al., "Essential role of CED–4 oligomerization in CED–3 activation and apoptosis" *Science*, 281:1355–1357 (1998).

Yuan and Horvitz, "The *Caenorhabditis elegans* cell death gene ced–4 encodes a novel protein and is expressed during the period of extensive programmed cell death" *Development*, 116:309–320 (1992).

Zervos et al. "Mxi1, a protein that specifically interacts with max to bind Myc–Max recognition sites" *Cell*, 72:223–232 (1993).

Zou et al., "Apaf–1, a human protein homologous to *C. elegans* CED–4, participates in cytochrome c–dependent activation of caspase–3" *Cell*, 90:405–413 (1997).

Zou et al., "An APAF–1•cytochrome c multimeric complex is a functional apoptosome that activates procaspase–9" *J. Biol. Chem.*, 274:11549–11556 (1999).

van der Biezen and Jones, "The NB–ARC domain: a novel signalling motif shared by plant resistance gene products and regulators of cell death in animals," *Current Biology* 8(7):226–227 (1998).

EMBL Database Accession No. AB023143.

Damiano et al., "*CLAN*, a Novel Human CED–4–like Gene," *Genomics* 75:77–83 (2001).

Geddes et al., "Human CARD12 Is a Novel CED4/Apaf–1 Family Member That Induces Apoptosis," *Biochemical and Biophysical Research Communications* 284:77–82 (2001).

Hofmann et al., "The CARD domain: a new apoptotic signalling motif," *TIBS* 22(5):155–156 (1997).

Kobe and Deisenhofer, "Proteins with leucine–rich repeats," *Current Opinion in Structural Biology*, 3(5):409–416 (1995).

Koonin and Aravind, "The NACHT family—a new group of predicted NHPases implicated in apoptosis and MHC transcription activation," *TIBS* 25(5):223–224 (2000).

Ogura et al., "Nod2, a Nod1/Apag–1 Family Member That Is Restricted to Monocytes and Activates NG–κB," *Journal of Biological Chemistry* 276(7):4812–4818 (2001).

Poyet et al., "Identification of Ipaf, a Human Caspase–1–activating Protein Related to Apaf–1," *Journal of Biological Chemistry* 276:28309–28313 (2001).

Rychlewski et al., "Comparison of sequence profiles. Strategies for structural predictions using sequence information," *Protein Science* 9:232–241 (2000).

Stapleton et al., "The crystal structure of an Eph receptor SAM domain reveals a mechanism for modular dimerization," *Nature Structural Biology* 6(1):44–49 (1999).

Database Accession No. AC007728, Database EMBL, "Homo sapiens chromosome 16 clone RP11–327f22, complete sequence" (Jun. 7, 1999).

Database Accession No. AC010968, Database EMBL, "Homo sapiens chromosome 2 clone RP11–9302, Working Draft Sequence, 11 unordered pieces" (Sep. 29, 1999).

Database Accession No. AC016492, Database EMBL, "Homo sapiens chromosome 4 clone RP11–94C22 map 4, Low–Pass Sequence Sampling" (Dec. 10, 1999).

Database Accession No. AC025758, Database EMBL, "Homo sapiens chromosome 5 clone CTD–2235A13, Working Draft Sequence, 16 ordered pieces" (Mar. 16, 2000).

Database Accession No. AC026732, Database EMBL, "Homo sapiens chromosome 5 clone CTD–2303L1, complete sequence" (Mar. 24, 2000).

Database Accession No. AQ534686, Database EBML, "Homo sapiens genomic clone RPCI–11–384F21, genomic survey sequence," (May 18, 1999).

* cited by examiner

```
                                   P-loop (Walker A)
NAC    (329-547)  IMLDGAAGIGKSTLARQVKEAWGRGQI-YQDRFQHVFYFS-------QREUA--Q-SKVISLAELIGKD
CARD4  (197-408)  TFFTLGDAGVGKSMELQRLQSMATSRUDASVKF--FSHER-----SRMPSCKE-SDT-LQDLFKH
Apaf-1 (138-352)  WYAEEGVMGCGKSVLVAE----NVRDHSLIE-CFPGGVHVSGKQDKSGLAMKLQNLCTRLDQDESFSQR
CD4    (154-374)  FRSLHGRGGSKSVLLSI--NLSKSDQI-SINYDSIVLKDSGTAPKSTFLSIDILLMLKSEDDI-LN Walker B
NAC    (329-547)  -----GTATACPAPHRQIL-------SR-PERLRPILDGV--DE--PGMVLQEPSSEL QLHWSQPQPADALLGS LLGSK
CARD4  (197-408)  YCYPBRDPEEVFAFL------------LRFPHVALFIFPGL--DELHSDLD-SRVPDSS--PWEPAHPL--VIIANI LSG
Apaf-1 (138-352)  LPLNIEEAKDRERILM---------LRKHPRSELIDFDWDS--MIKAFDSQ---QILLNTRDSVIDSVMGPH
CD4    (154-374)  FBSVBHVTSVLKRMICNALIDRENTEVFDMVQEITRMA-DELRLR--S---VLLRDVELSNEASQTC NAC    (329-547)  TILPEASFILRAR-----TLFQNLIPSLEQARMVEMLFFSESSRKETYRV--FIDE
CARD4  (197-408)  KLLKGASKLIFAR-----------LGIE-----VPRQFLRKKVIPERGRSPEHURAHARM--EPER
Apaf-1 (138-352)  YVMPVFSSLGKEKGLEILSLF-VNEKKADLPFQA--HSI--KBCCKSF-----LWSLIGKVLQRDFPNSMEYLK
CD4    (154-374)  EFFLEM--ISLEIDBCYDFLBAYGMPFPVGEKEEDVNKTLELSSNPAMMFMSCEPKIEBKMAQLN-N NAC    (329-547)  RQEIRAFRLVKSNKEIWALCLIPWVSILACTCMQQMKRK
CARD4  (197-408)  ATQDRLIESQLEANPNICSLCSSVELFCNIIFRCFQHFRAAF
Apaf-1 (138-352)  QLONKQFKRIRKSSY----------DMEAHDEA
CD4    (154-374)  KJESLBGBECITPY------------SVKSI
```

FIGURE 1E

| LexA | B42 | Leu+ | Leu- | LacZ |
|---|---|---|---|---|
| NAC-CARD | Casp-9 (CARD)<br>Casp-8 (Pro)<br>Apaf-1 (-WD)<br>Bcl-XL (-TM)<br>Bcl-2 (-TM)<br>Bax (-TM)<br>vRas | | | ++<br>+/-<br>++<br>+/-<br>+/-<br>-<br>- |
| Casp-9 (CARD) | NAC-CARD<br>Apaf-1 (-WD)<br>vRas | | | ++<br>++<br>- |
| Casp-8 (Pro) | NAC-CARD<br>FADD<br>vRas | | | -<br>++++<br>- |
| Apaf-1 (-WD) | NAC-CARD<br>Casp-9 (CARD)<br>vRas | | | +<br>++++<br>- |
| Bcl-XL (-TM) | NAC-CARD<br>Bcl-XL (-TM)<br>Apaf-1 (-WD)<br>vRas | | | +++<br>+++<br>+++<br>- |
| Bax | NAC-CARD<br>Bax (-TM)<br>Bcl-2 (-TM)<br>vRas | | | +/-<br>++++<br>+<br>- |
| Bcl-2 (-TM) | NAC-CARD<br>Bcl-2 (-TM)<br>Bax (-TM)<br>vRas | | | ++<br>+++<br>+++<br>- |

WB:  Lysate | IP: myc Flag myc
     1 2 3  | 1 2 3

WB:
myc                    ← NAC

HA                     ← Apaf-1 (ΔWD)

myc-NAC         − + +   − + +
HA-Apaf-1 (ΔWD) + + +   + + +

FIGURE 5B

WB:  Lysate | IP: myc Flag myc
     1 2 3  | 1 2 3

WB:
myc                    ← NAC

HA                     ← CED4 myc-NAC   − + +   − + +
HA-CED4   + + +   + + +

SEQUENCE LISTING

<160> NUMBER OF SEQ ID NOS: 30

<210> SEQ ID NO 1
<211> LENGTH: 4422
<212> TYPE: DNA
<213> ORGANISM: Homo sapiens
<220> FEATURE:
<221> NAME/KEY: CDS
<222> LOCATION: (1)..(4422)

<400> SEQUENCE: 1

```
atg gct ggc gga gcc tgg ggc cgc ctg gcc tgt tac ttg gag ttc ctg         48
Met Ala Gly Gly Ala Trp Gly Arg Leu Ala Cys Tyr Leu Glu Phe Leu
  1               5                  10                  15 aag aag gag gag ctg aag gag ttc cag ctt ctg ctc gcc aat aaa gcg         96
Lys Lys Glu Glu Leu Lys Glu Phe Gln Leu Leu Leu Ala Asn Lys Ala
             20                  25                  30 cac tcc agg agc tct tcg ggt gag aca ccc gct cag cca gag aag acg        144
His Ser Arg Ser Ser Ser Gly Glu Thr Pro Ala Gln Pro Glu Lys Thr
         35                  40                  45 agt ggc atg gag gtg gcc tcg tac ctg gtg gct cag tat ggg gag cag        192
Ser Gly Met Glu Val Ala Ser Tyr Leu Val Ala Gln Tyr Gly Glu Gln
     50                  55                  60 cgg gcc tgg gac cta gcc ctc cat acc tgg gag cag atg ggg ctg agg        240
Arg Ala Trp Asp Leu Ala Leu His Thr Trp Glu Gln Met Gly Leu Arg
 65                  70                  75                  80 tca ctg tgc gcc caa gcc cag gaa ggg gca ggc cac tct ccc tca ttc        288
Ser Leu Cys Ala Gln Ala Gln Glu Gly Ala Gly His Ser Pro Ser Phe
                 85                  90                  95 ccc tac agc cca agt gaa ccc cac ctg ggg tct ccc agc caa ccc acc        336
Pro Tyr Ser Pro Ser Glu Pro His Leu Gly Ser Pro Ser Gln Pro Thr
            100                 105                 110 tcc acc gca gtg cta atg ccc tgg atc cat gaa ttg ccg gcg ggg tgc        384
Ser Thr Ala Val Leu Met Pro Trp Ile His Glu Leu Pro Ala Gly Cys
        115                 120                 125 acc cag ggc tca gag aga agg gtt ttg aga cag ctg cct gac aca tct        432
Thr Gln Gly Ser Glu Arg Arg Val Leu Arg Gln Leu Pro Asp Thr Ser
    130                 135                 140
```

-continued

| | |
|---|---|
| gga cgc cgc tgg aga gaa atc tct gcc tca ctc ctc tac caa gct ctt<br>Gly Arg Arg Trp Arg Glu Ile Ser Ala Ser Leu Leu Tyr Gln Ala Leu<br>145                            150                        155                    160 | 480 |
| cca agc tcc cca gac cat gag tct cca agc cag gag tca ccc aac gcc<br>Pro Ser Ser Pro Asp His Glu Ser Pro Ser Gln Glu Ser Pro Asn Ala<br>                    165                        170                        175 | 528 |
| ccc aca tcc aca gca gtg ctg ggg agc tgg gga tcc cca cct cag ccc<br>Pro Thr Ser Thr Ala Val Leu Gly Ser Trp Gly Ser Pro Pro Gln Pro<br>              180                        185                        190 | 576 |
| agc cta gca ccc aga gag cag gag gct cct ggg acc caa tgg cct ctg<br>Ser Leu Ala Pro Arg Glu Gln Glu Ala Pro Gly Thr Gln Trp Pro Leu<br>        195                        200                        205 | 624 |
| gat gaa acg tca gga att tac tac aca gaa atc aga gaa aga gag aga<br>Asp Glu Thr Ser Gly Ile Tyr Tyr Thr Glu Ile Arg Glu Arg Glu Arg<br>210                            215                        220 | 672 |
| gag aaa tca gag aaa ggc agg ccc cca tgg gca gcg gtg gta gga acg<br>Glu Lys Ser Glu Lys Gly Arg Pro Pro Trp Ala Ala Val Val Gly Thr<br>225                            230                        235                    240 | 720 |
| ccc cca cag gcg cac acc agc cta cag ccc cac cac cac cca tgg gag<br>Pro Pro Gln Ala His Thr Ser Leu Gln Pro His His His Pro Trp Glu<br>                    245                        250                        255 | 768 |
| cct tct gtg aga gag agc ctc tgt tcc aca tgg ccc tgg aaa aat gag<br>Pro Ser Val Arg Glu Ser Leu Cys Ser Thr Trp Pro Trp Lys Asn Glu<br>        260                        265                        270 | 816 |
| gat ttt aac caa aaa ttc aca cag ctg cta ctt cta caa aga cct cac<br>Asp Phe Asn Gln Lys Phe Thr Gln Leu Leu Leu Leu Gln Arg Pro His<br>                    275                        280                        285 | 864 |
| ccc aga agc caa gat ccc ctg gtc aag aga agc tgg cct gat tat gtg<br>Pro Arg Ser Gln Asp Pro Leu Val Lys Arg Ser Trp Pro Asp Tyr Val<br>        290                        295                        300 | 912 |
| gag gag aat cga gga cat tta att gag atc aga gac tta ttt ggc cca<br>Glu Glu Asn Arg Gly His Leu Ile Glu Ile Arg Asp Leu Phe Gly Pro<br>305                            310                        315                    320 | 960 |
| ggc ctg gat acc caa gaa cct cgc ata gtc ata ctg cag ggg gct gct<br>Gly Leu Asp Thr Gln Glu Pro Arg Ile Val Ile Leu Gln Gly Ala Ala<br>                    325                        330                        335 | 1008 |
| gga att ggg aag tca aca ctg gcc agg cag gtg aag gaa gcc tgg ggg<br>Gly Ile Gly Lys Ser Thr Leu Ala Arg Gln Val Lys Glu Ala Trp Gly<br>        340                        345                        350 | 1056 |
| aga ggc cag ctg tat ggg gac cgc ttc cag cat gtc ttc tac ttc agc<br>Arg Gly Gln Leu Tyr Gly Asp Arg Phe Gln His Val Phe Tyr Phe Ser<br>                    355                        360                        365 | 1104 |
| tgc aga gag ctg gcc cag tcc aag gtg gtg agt ctc gct gag ctc atc<br>Cys Arg Glu Leu Ala Gln Ser Lys Val Val Ser Leu Ala Glu Leu Ile<br>        370                        375                        380 | 1152 |
| gga aaa gat ggg aca gcc act ccg gct ccc att aga cag atc ctg tct<br>Gly Lys Asp Gly Thr Ala Thr Pro Ala Pro Ile Arg Gln Ile Leu Ser<br>385                            390                        395                    400 | 1200 |
| agg cca gag cgg ctg ctc ttc atc ctc gat ggt gta gat gag cca gga<br>Arg Pro Glu Arg Leu Leu Phe Ile Leu Asp Gly Val Asp Glu Pro Gly<br>                    405                        410                        415 | 1248 |
| tgg gtc ttg cag gag ccg agt tct gag ctc tgt ctg cac tgg agc cag<br>Trp Val Leu Gln Glu Pro Ser Ser Glu Leu Cys Leu His Trp Ser Gln<br>                    420                        425                        430 | 1296 |
| cca cag ccg gcg gat gca ctg ctg ggc agt ttg ctg ggg aaa act ata<br>Pro Gln Pro Ala Asp Ala Leu Leu Gly Ser Leu Leu Gly Lys Thr Ile<br>        435                        440                        445 | 1344 |
| ctt ccc gag gca tcc ttc ctg atc acg gct cgg acc aca gct ctg cag<br>Leu Pro Glu Ala Ser Phe Leu Ile Thr Ala Arg Thr Thr Ala Leu Gln | 1392 |

```
                450                 455                 460
aac ctc att cct tct ttg gag cag gca cgt tgg gta gag gtc ctg ggg         1440
Asn Leu Ile Pro Ser Leu Glu Gln Ala Arg Trp Val Glu Val Leu Gly
465                 470                 475                 480 ttc tct gag tcc agc agg aag gaa tat ttc tac aga tat ttc aca gat         1488
Phe Ser Glu Ser Ser Arg Lys Glu Tyr Phe Tyr Arg Tyr Phe Thr Asp
                485                 490                 495 gaa agg caa gca att aga gcc ttt agg ttg gtc aaa tca aac aaa gag         1536
Glu Arg Gln Ala Ile Arg Ala Phe Arg Leu Val Lys Ser Asn Lys Glu
            500                 505                 510 ctc tgg gcc ctg tgt ctt gtg ccc tgg gtg tcc tgg ctg gcc tgc act         1584
Leu Trp Ala Leu Cys Leu Val Pro Trp Val Ser Trp Leu Ala Cys Thr
        515                 520                 525 tgc ctg atg cag cag atg aag cgg aag gaa aaa ctc aca ctg act tcc         1632
Cys Leu Met Gln Gln Met Lys Arg Lys Glu Lys Leu Thr Leu Thr Ser
    530                 535                 540 aag acc acc aca acc ctc tgt cta cat tac ctt gcc cag gct ctc caa         1680
Lys Thr Thr Thr Thr Leu Cys Leu His Tyr Leu Ala Gln Ala Leu Gln
545                 550                 555                 560 gct cag cca ttg gga ccc cag ctc aga gac ctc tgc tct ctg gct gct         1728
Ala Gln Pro Leu Gly Pro Gln Leu Arg Asp Leu Cys Ser Leu Ala Ala
                565                 570                 575 gag ggc atc tgg caa aaa aag acc ctt ttc agt cca gat gac ctc agg         1776
Glu Gly Ile Trp Gln Lys Lys Thr Leu Phe Ser Pro Asp Asp Leu Arg
            580                 585                 590 aag cat ggg tta gat ggg gcc atc atc tcc acc ttc ttg aag atg ggt         1824
Lys His Gly Leu Asp Gly Ala Ile Ile Ser Thr Phe Leu Lys Met Gly
        595                 600                 605 att ctt caa gag cac ccc atc cct ctg agc tac agc ttc att cac ctc         1872
Ile Leu Gln Glu His Pro Ile Pro Leu Ser Tyr Ser Phe Ile His Leu
    610                 615                 620 tgt ttc caa gag ttc ttt gca gca atg tcc tat gtc ttg gag gat gag         1920
Cys Phe Gln Glu Phe Phe Ala Ala Met Ser Tyr Val Leu Glu Asp Glu
625                 630                 635                 640 aag ggg aga ggt aaa cat tct aat tgc atc ata gat ttg gaa aag acg         1968
Lys Gly Arg Gly Lys His Ser Asn Cys Ile Ile Asp Leu Glu Lys Thr
                645                 650                 655 cta gaa gca tat gga ata cat ggc ctg ttt ggg gca tca acc aca cgt         2016
Leu Glu Ala Tyr Gly Ile His Gly Leu Phe Gly Ala Ser Thr Thr Arg
            660                 665                 670 ttc cta ttg ggc ctg tta agt gat gag ggg gag aga gag atg gag aac         2064
Phe Leu Leu Gly Leu Leu Ser Asp Glu Gly Glu Arg Glu Met Glu Asn
        675                 680                 685 atc ttt cac tgc cgg ctg tct cag ggg agg aac ctg atg cag tgg gtc         2112
Ile Phe His Cys Arg Leu Ser Gln Gly Arg Asn Leu Met Gln Trp Val
    690                 695                 700 ccg tcc ctg cag ctg ctg ctg cag cca cac tct ctg gag tcc ctc cac         2160
Pro Ser Leu Gln Leu Leu Leu Gln Pro His Ser Leu Glu Ser Leu His
705                 710                 715                 720 tgc ttg tac gag act cgg aac aaa acg ttc ctg aca caa gtg atg gcc         2208
Cys Leu Tyr Glu Thr Arg Asn Lys Thr Phe Leu Thr Gln Val Met Ala
                725                 730                 735 cat ttc gaa gaa atg ggc atg tgt gta gaa aca gac atg gag ctc tta         2256
His Phe Glu Glu Met Gly Met Cys Val Glu Thr Asp Met Glu Leu Leu
            740                 745                 750 gtg tgc act ttc tgc att aaa ttc agc cgc cac gtg aag aag ctt cag         2304
Val Cys Thr Phe Cys Ile Lys Phe Ser Arg His Val Lys Lys Leu Gln
        755                 760                 765 ctg att gag ggc agg cag cac aga tca aca tgg agc ccc acc atg gta         2352
```

```
                                                          -continued

Leu Ile Glu Gly Arg Gln His Arg Ser Thr Trp Ser Pro Thr Met Val
        770                 775                 780 gtc ctg ttc agg tgg gtc cca gtc aca gat gcc tat tgg cag att ctc        2400
Val Leu Phe Arg Trp Val Pro Val Thr Asp Ala Tyr Trp Gln Ile Leu
785                 790                 795                 800 ttc tcc gtc ctc aag gtc acc aga aac ctg aag gag ctg gac cta agt        2448
Phe Ser Val Leu Lys Val Thr Arg Asn Leu Lys Glu Leu Asp Leu Ser
                805                 810                 815 gga aac tcg ctg agc cac tct gca gtg aag agt ctt tgt aag acc ctg        2496
Gly Asn Ser Leu Ser His Ser Ala Val Lys Ser Leu Cys Lys Thr Leu
            820                 825                 830 aga cgc cct cgc tgc ctc ctg gag acc ctg cgg ttg gct ggc tgt ggc        2544
Arg Arg Pro Arg Cys Leu Leu Glu Thr Leu Arg Leu Ala Gly Cys Gly
        835                 840                 845 ctc aca gct gag gac tgc aag gac ctt gcc ttt ggg ctg aga gcc aac        2592
Leu Thr Ala Glu Asp Cys Lys Asp Leu Ala Phe Gly Leu Arg Ala Asn
850                 855                 860 cag acc ctg acc gag ctg gac ctg agc ttc aat gtg ctc acg gat gct        2640
Gln Thr Leu Thr Glu Leu Asp Leu Ser Phe Asn Val Leu Thr Asp Ala
865                 870                 875                 880 gga gcc aaa cac ctt tgc cag aga ctg aga cag ccg agc tgc aag cta        2688
Gly Ala Lys His Leu Cys Gln Arg Leu Arg Gln Pro Ser Cys Lys Leu
                885                 890                 895 cag cga ctg cag ctg gtc agc tgt ggc ctc acg tct gac tgc tgc cag        2736
Gln Arg Leu Gln Leu Val Ser Cys Gly Leu Thr Ser Asp Cys Cys Gln
            900                 905                 910 gac ctg gcc tct gtg ctt agt gcc agc ccc agc ctg aag gag cta gac        2784
Asp Leu Ala Ser Val Leu Ser Ala Ser Pro Ser Leu Lys Glu Leu Asp
        915                 920                 925 ctg cag cag aac aac ctg gat gac gtt ggc gtg cga ctg ctc tgt gag        2832
Leu Gln Gln Asn Asn Leu Asp Asp Val Gly Val Arg Leu Leu Cys Glu
    930                 935                 940 ggg ctc agg cat cct gcc tgc aaa ctc ata cgc ctg ggg ctg gac cag        2880
Gly Leu Arg His Pro Ala Cys Lys Leu Ile Arg Leu Gly Leu Asp Gln
945                 950                 955                 960 aca act ctg agt gat gag atg agg cag gaa ctg agg gcc ctg gag cag        2928
Thr Thr Leu Ser Asp Glu Met Arg Gln Glu Leu Arg Ala Leu Glu Gln
                965                 970                 975 gag aaa cct cag ctg ctc atc ttc agc aga cgg aaa cca agt gtg atg        2976
Glu Lys Pro Gln Leu Leu Ile Phe Ser Arg Arg Lys Pro Ser Val Met
            980                 985                 990 acc cct act gag ggc ctg gat acg gga gag atg agt aat agc aca tcc        3024
Thr Pro Thr Glu Gly Leu Asp Thr Gly Glu Met Ser Asn Ser Thr Ser
        995                 1000                1005 tca ctc aag cgg cag aga ctc gga tca gag agg gcg gct tcc cat gtt        3072
Ser Leu Lys Arg Gln Arg Leu Gly Ser Glu Arg Ala Ala Ser His Val
    1010                1015                1020 gct cag gct aat ctc aaa ctc ctg gac gtg agc aag atc ttc cca att        3120
Ala Gln Ala Asn Leu Lys Leu Leu Asp Val Ser Lys Ile Phe Pro Ile
1025                1030                1035                1040 gct gag att gca gag gaa agc tcc cca gag gta gta ccg gtg gaa ctc        3168
Ala Glu Ile Ala Glu Glu Ser Ser Pro Glu Val Val Pro Val Glu Leu
                1045                1050                1055 ttg tgc gtg cct tct cct gcc tct caa ggg gac ctg cat acg aag cct        3216
Leu Cys Val Pro Ser Pro Ala Ser Gln Gly Asp Leu His Thr Lys Pro
            1060                1065                1070 ttg ggg act gac gat gac ttc tgg ggc ccc acg ggg cct gtg gct act        3264
Leu Gly Thr Asp Asp Asp Phe Trp Gly Pro Thr Gly Pro Val Ala Thr
        1075                1080                1085
```

```
gag gta gtt gac aaa gaa aag aac ttg tac cga gtt cac ttc cct gta      3312
Glu Val Val Asp Lys Glu Lys Asn Leu Tyr Arg Val His Phe Pro Val
    1090                1095                1100 gct ggc tcc tac cgc tgg ccc aac acg ggt ctc tgc ttt gtg atg aga      3360
Ala Gly Ser Tyr Arg Trp Pro Asn Thr Gly Leu Cys Phe Val Met Arg
1105                1110                1115                1120 gaa gcg gtg acc gtt gag att gaa ttc tgt gtg tgg gac cag ttc ctg      3408
Glu Ala Val Thr Val Glu Ile Glu Phe Cys Val Trp Asp Gln Phe Leu
            1125                1130                1135 ggt gag atc aac cca cag cac agc tgg atg gtg gca ggg cct ctg ctg      3456
Gly Glu Ile Asn Pro Gln His Ser Trp Met Val Ala Gly Pro Leu Leu
        1140                1145                1150 gac atc aag gct gag cct gga gct gtg gaa gct gtg cac ctc cct cac      3504
Asp Ile Lys Ala Glu Pro Gly Ala Val Glu Ala Val His Leu Pro His
    1155                1160                1165 ttt gtg gct ctc caa ggg ggc cat gtg gac aca tcc ctg ttc caa atg      3552
Phe Val Ala Leu Gln Gly Gly His Val Asp Thr Ser Leu Phe Gln Met
    1170                1175                1180 gcc cac ttt aaa gag gag ggg atg ctc ctg gag aag cca gcc agg gtg      3600
Ala His Phe Lys Glu Glu Gly Met Leu Leu Glu Lys Pro Ala Arg Val
1185                1190                1195                1200 gag ctg cat cac ata gtt ctg gaa aac ccc agc ttc tcc ccc ttg gga      3648
Glu Leu His His Ile Val Leu Glu Asn Pro Ser Phe Ser Pro Leu Gly
            1205                1210                1215 gtc ctc ctg aaa atg atc cat aat gcc ctg cgc ttc att ccc gtc acc      3696
Val Leu Leu Lys Met Ile His Asn Ala Leu Arg Phe Ile Pro Val Thr
        1220                1225                1230 tct gtg gtg ttg ctt tac cac cgc gtc cat cct gag gaa gtc acc ttc      3744
Ser Val Val Leu Leu Tyr His Arg Val His Pro Glu Glu Val Thr Phe
    1235                1240                1245 cac ctc tac ctg atc cca agt gac tgc tcc att cgg aag gcc ata gat      3792
His Leu Tyr Leu Ile Pro Ser Asp Cys Ser Ile Arg Lys Ala Ile Asp
    1250                1255                1260 gat cta gaa atg aaa ttc cag ttt gtg cga atc cac aag cca ccc ccg      3840
Asp Leu Glu Met Lys Phe Gln Phe Val Arg Ile His Lys Pro Pro Pro
1265                1270                1275                1280 ctg acc cca ctt tat atg ggc tgt cgt tac act gtg tct ggg tct ggt      3888
Leu Thr Pro Leu Tyr Met Gly Cys Arg Tyr Thr Val Ser Gly Ser Gly
            1285                1290                1295 tca ggg atg ctg gaa ata ctc ccc aag gaa ctg gag ctc tgc tat cga      3936
Ser Gly Met Leu Glu Ile Leu Pro Lys Glu Leu Glu Leu Cys Tyr Arg
        1300                1305                1310 agc cct gga gaa gac cag ctg ttc tcg gag ttc tac gtt ggc cac ttg      3984
Ser Pro Gly Glu Asp Gln Leu Phe Ser Glu Phe Tyr Val Gly His Leu
    1315                1320                1325 gga tca ggg atc agg ctg caa gtg aaa gac aag aaa gat gag act ctg      4032
Gly Ser Gly Ile Arg Leu Gln Val Lys Asp Lys Lys Asp Glu Thr Leu
    1330                1335                1340 gtg tgg gag gcc ttg gtg aaa cca gga gat ctc atg cct gca act act      4080
Val Trp Glu Ala Leu Val Lys Pro Gly Asp Leu Met Pro Ala Thr Thr
1345                1350                1355                1360 ctg atc cct cca gcc cgc ata gcc gta cct tca cct ctg gat gcc ccg      4128
Leu Ile Pro Pro Ala Arg Ile Ala Val Pro Ser Pro Leu Asp Ala Pro
            1365                1370                1375 cag ttg ctg cac ttt gtg gac cag tat cga gag cag ctg ata gcc cga      4176
Gln Leu Leu His Phe Val Asp Gln Tyr Arg Glu Gln Leu Ile Ala Arg
        1380                1385                1390 gtg aca tcg gtg gag gtt gtc ttg gac aaa ctg cat gga cag gtg ctg      4224
Val Thr Ser Val Glu Val Val Leu Asp Lys Leu His Gly Gln Val Leu
    1395                1400                1405
```

-continued

```
agc cag gag cag tac gag agg gtg ctg gct gag aac acg agg ccc agc    4272
Ser Gln Glu Gln Tyr Glu Arg Val Leu Ala Glu Asn Thr Arg Pro Ser
    1410            1415                1420 cag atg cgg aag ctg ttc agc ttg agc cag tcc tgg gac cgg aag tgc    4320
Gln Met Arg Lys Leu Phe Ser Leu Ser Gln Ser Trp Asp Arg Lys Cys
1425            1430                1435                1440 aaa gat gga ctc tac caa gcc ctg aag gag acc cat cct cac ctc att    4368
Lys Asp Gly Leu Tyr Gln Ala Leu Lys Glu Thr His Pro His Leu Ile
                1445                1450                1455 atg gaa ctc tgg gag aag ggc agc aaa aag gga ctc ctg cca ctc agc    4416
Met Glu Leu Trp Glu Lys Gly Ser Lys Lys Gly Leu Leu Pro Leu Ser
            1460                1465                1470 agc tga                                                            4422
Ser
```

<210> SEQ ID NO 2
<211> LENGTH: 1473
<212> TYPE: PRT
<213> ORGANISM: Homo sapiens

<400> SEQUENCE: 2

```
Met Ala Gly Gly Ala Trp Gly Arg Leu Ala Cys Tyr Leu Glu Phe Leu
  1               5                  10                  15

Lys Lys Glu Glu Leu Lys Glu Phe Gln Leu Leu Leu Ala Asn Lys Ala
             20                  25                  30

His Ser Arg Ser Ser Ser Gly Glu Thr Pro Ala Gln Pro Glu Lys Thr
         35                  40                  45

Ser Gly Met Glu Val Ala Ser Tyr Leu Val Ala Gln Tyr Gly Glu Gln
     50                  55                  60

Arg Ala Trp Asp Leu Ala Leu His Thr Trp Glu Gln Met Gly Leu Arg
 65                  70                  75                  80

Ser Leu Cys Ala Gln Ala Gln Glu Gly Ala Gly His Ser Pro Ser Phe
                 85                  90                  95

Pro Tyr Ser Pro Ser Glu Pro His Leu Gly Ser Pro Ser Gln Pro Thr
            100                 105                 110

Ser Thr Ala Val Leu Met Pro Trp Ile His Glu Leu Pro Ala Gly Cys
        115                 120                 125

Thr Gln Gly Ser Glu Arg Arg Val Leu Arg Gln Leu Pro Asp Thr Ser
    130                 135                 140

Gly Arg Arg Trp Arg Glu Ile Ser Ala Ser Leu Leu Tyr Gln Ala Leu
145                 150                 155                 160

Pro Ser Ser Pro Asp His Glu Ser Pro Ser Gln Glu Ser Pro Asn Ala
                165                 170                 175

Pro Thr Ser Thr Ala Val Leu Gly Ser Trp Gly Ser Pro Pro Gln Pro
            180                 185                 190

Ser Leu Ala Pro Arg Glu Gln Glu Ala Pro Gly Thr Gln Trp Pro Leu
        195                 200                 205

Asp Glu Thr Ser Gly Ile Tyr Tyr Thr Glu Ile Arg Glu Arg Glu Arg
    210                 215                 220

Glu Lys Ser Glu Lys Gly Arg Pro Pro Trp Ala Ala Val Val Gly Thr
225                 230                 235                 240

Pro Pro Gln Ala His Thr Ser Leu Gln Pro His His Pro Trp Glu
                245                 250                 255

Pro Ser Val Arg Glu Ser Leu Cys Ser Thr Trp Pro Trp Lys Asn Glu
            260                 265                 270
```

-continued

```
Asp Phe Asn Gln Lys Phe Thr Gln Leu Leu Leu Gln Arg Pro His
        275                 280                 285
Pro Arg Ser Gln Asp Pro Leu Val Lys Arg Ser Trp Pro Asp Tyr Val
    290                 295                 300
Glu Glu Asn Arg Gly His Leu Ile Glu Ile Arg Asp Leu Phe Gly Pro
305                 310                 315                 320
Gly Leu Asp Thr Gln Glu Pro Arg Ile Val Ile Leu Gln Gly Ala Ala
                325                 330                 335
Gly Ile Gly Lys Ser Thr Leu Ala Arg Gln Val Lys Glu Ala Trp Gly
                340                 345                 350
Arg Gly Gln Leu Tyr Gly Asp Arg Phe Gln His Val Phe Tyr Phe Ser
                355                 360                 365
Cys Arg Glu Leu Ala Gln Ser Lys Val Val Ser Leu Ala Glu Leu Ile
    370                 375                 380
Gly Lys Asp Gly Thr Ala Thr Pro Ala Pro Ile Arg Gln Ile Leu Ser
385                 390                 395                 400
Arg Pro Glu Arg Leu Leu Phe Ile Leu Asp Gly Val Asp Glu Pro Gly
                405                 410                 415
Trp Val Leu Gln Glu Pro Ser Ser Glu Leu Cys Leu His Trp Ser Gln
                420                 425                 430
Pro Gln Pro Ala Asp Ala Leu Leu Gly Ser Leu Leu Gly Lys Thr Ile
                435                 440                 445
Leu Pro Glu Ala Ser Phe Leu Ile Thr Ala Arg Thr Thr Ala Leu Gln
                450                 455                 460
Asn Leu Ile Pro Ser Leu Glu Gln Ala Arg Trp Val Glu Val Leu Gly
465                 470                 475                 480
Phe Ser Glu Ser Ser Arg Lys Glu Tyr Phe Tyr Arg Tyr Phe Thr Asp
                485                 490                 495
Glu Arg Gln Ala Ile Arg Ala Phe Arg Leu Val Lys Ser Asn Lys Glu
                500                 505                 510
Leu Trp Ala Leu Cys Leu Val Pro Trp Val Ser Trp Leu Ala Cys Thr
                515                 520                 525
Cys Leu Met Gln Gln Met Lys Arg Lys Glu Lys Leu Thr Leu Thr Ser
    530                 535                 540
Lys Thr Thr Thr Thr Leu Cys Leu His Tyr Leu Ala Gln Ala Leu Gln
545                 550                 555                 560
Ala Gln Pro Leu Gly Pro Gln Leu Arg Asp Leu Cys Ser Leu Ala Ala
                565                 570                 575
Glu Gly Ile Trp Gln Lys Lys Thr Leu Phe Ser Pro Asp Asp Leu Arg
                580                 585                 590
Lys His Gly Leu Asp Gly Ala Ile Ile Ser Thr Phe Leu Lys Met Gly
                595                 600                 605
Ile Leu Gln Glu His Pro Ile Pro Leu Ser Tyr Ser Phe Ile His Leu
                610                 615                 620
Cys Phe Gln Glu Phe Phe Ala Ala Met Ser Tyr Val Leu Glu Asp Glu
625                 630                 635                 640
Lys Gly Arg Gly Lys His Ser Asn Cys Ile Ile Asp Leu Glu Lys Thr
                645                 650                 655
Leu Glu Ala Tyr Gly Ile His Gly Leu Phe Gly Ala Ser Thr Thr Arg
                660                 665                 670
Phe Leu Leu Gly Leu Leu Ser Asp Glu Gly Glu Arg Glu Met Glu Asn
                675                 680                 685
Ile Phe His Cys Arg Leu Ser Gln Gly Arg Asn Leu Met Gln Trp Val
```

-continued

```
            690                 695                 700
Pro Ser Leu Gln Leu Leu Gln Pro His Ser Leu Glu Ser Leu His
705                 710                 715                 720

Cys Leu Tyr Glu Thr Arg Asn Lys Thr Phe Leu Thr Gln Val Met Ala
                725                 730                 735

His Phe Glu Glu Met Gly Met Cys Val Glu Thr Asp Met Glu Leu Leu
                740                 745                 750

Val Cys Thr Phe Cys Ile Lys Phe Ser Arg His Val Lys Lys Leu Gln
                755                 760                 765

Leu Ile Glu Gly Arg Gln His Arg Ser Thr Trp Ser Pro Thr Met Val
770                 775                 780

Val Leu Phe Arg Trp Val Pro Val Thr Asp Ala Tyr Trp Gln Ile Leu
785                 790                 795                 800

Phe Ser Val Leu Lys Val Thr Arg Asn Leu Lys Glu Leu Asp Leu Ser
                805                 810                 815

Gly Asn Ser Leu Ser His Ser Ala Val Lys Ser Leu Cys Lys Thr Leu
                820                 825                 830

Arg Arg Pro Arg Cys Leu Leu Glu Thr Leu Arg Leu Ala Gly Cys Gly
                835                 840                 845

Leu Thr Ala Glu Asp Cys Lys Asp Leu Ala Phe Gly Leu Arg Ala Asn
850                 855                 860

Gln Thr Leu Thr Glu Leu Asp Leu Ser Phe Asn Val Leu Thr Asp Ala
865                 870                 875                 880

Gly Ala Lys His Leu Cys Gln Arg Leu Arg Gln Pro Ser Cys Lys Leu
                885                 890                 895

Gln Arg Leu Gln Leu Val Ser Cys Gly Leu Thr Ser Asp Cys Cys Gln
                900                 905                 910

Asp Leu Ala Ser Val Leu Ser Ala Ser Pro Ser Leu Lys Glu Leu Asp
                915                 920                 925

Leu Gln Gln Asn Asn Leu Asp Asp Val Gly Val Arg Leu Leu Cys Glu
                930                 935                 940

Gly Leu Arg His Pro Ala Cys Lys Leu Ile Arg Leu Gly Leu Asp Gln
945                 950                 955                 960

Thr Thr Leu Ser Asp Glu Met Arg Gln Glu Leu Arg Ala Leu Glu Gln
                965                 970                 975

Glu Lys Pro Gln Leu Leu Ile Phe Ser Arg Arg Lys Pro Ser Val Met
                980                 985                 990

Thr Pro Thr Glu Gly Leu Asp Thr Gly Glu Met Ser Asn Ser Thr Ser
                995                 1000                1005

Ser Leu Lys Arg Gln Arg Leu Gly Ser Glu Arg Ala Ala Ser His Val
                1010                1015                1020

Ala Gln Ala Asn Leu Lys Leu Leu Asp Val Ser Lys Ile Phe Pro Ile
1025                1030                1035                1040

Ala Glu Ile Ala Glu Ser Ser Pro Glu Val Val Pro Val Glu Leu
                1045                1050                1055

Leu Cys Val Pro Ser Pro Ala Ser Gln Gly Asp Leu His Thr Lys Pro
                1060                1065                1070

Leu Gly Thr Asp Asp Phe Trp Gly Pro Thr Gly Pro Val Ala Thr
                1075                1080                1085

Glu Val Val Asp Lys Glu Lys Asn Leu Tyr Arg Val His Phe Pro Val
                1090                1095                1100

Ala Gly Ser Tyr Arg Trp Pro Asn Thr Gly Leu Cys Phe Val Met Arg
1105                1110                1115                1120
```

```
Glu Ala Val Thr Val Glu Ile Glu Phe Cys Val Trp Asp Gln Phe Leu
            1125                1130                1135

Gly Glu Ile Asn Pro Gln His Ser Trp Met Val Ala Gly Pro Leu Leu
        1140                1145                1150

Asp Ile Lys Ala Glu Pro Gly Ala Val Glu Ala Val His Leu Pro His
        1155                1160                1165

Phe Val Ala Leu Gln Gly Gly His Val Asp Thr Ser Leu Phe Gln Met
    1170                1175                1180

Ala His Phe Lys Glu Glu Gly Met Leu Leu Glu Lys Pro Ala Arg Val
1185                1190                1195                1200

Glu Leu His His Ile Val Leu Glu Asn Pro Ser Phe Ser Pro Leu Gly
            1205                1210                1215

Val Leu Leu Lys Met Ile His Asn Ala Leu Arg Phe Ile Pro Val Thr
            1220                1225                1230

Ser Val Val Leu Leu Tyr His Arg Val His Pro Glu Glu Val Thr Phe
        1235                1240                1245

His Leu Tyr Leu Ile Pro Ser Asp Cys Ser Ile Arg Lys Ala Ile Asp
        1250                1255                1260

Asp Leu Glu Met Lys Phe Gln Phe Val Arg Ile His Lys Pro Pro Pro
1265                1270                1275                1280

Leu Thr Pro Leu Tyr Met Gly Cys Arg Tyr Thr Val Ser Gly Ser Gly
            1285                1290                1295

Ser Gly Met Leu Glu Ile Leu Pro Lys Glu Leu Glu Leu Cys Tyr Arg
        1300                1305                1310

Ser Pro Gly Glu Asp Gln Leu Phe Ser Glu Phe Tyr Val Gly His Leu
        1315                1320                1325

Gly Ser Gly Ile Arg Leu Gln Val Lys Asp Lys Asp Glu Thr Leu
        1330                1335                1340

Val Trp Glu Ala Leu Val Lys Pro Gly Asp Leu Met Pro Ala Thr Thr
1345                1350                1355                1360

Leu Ile Pro Pro Ala Arg Ile Ala Val Pro Ser Pro Leu Asp Ala Pro
            1365                1370                1375

Gln Leu Leu His Phe Val Asp Gln Tyr Arg Glu Gln Leu Ile Ala Arg
        1380                1385                1390

Val Thr Ser Val Glu Val Val Leu Asp Lys Leu His Gly Gln Val Leu
            1395                1400                1405

Ser Gln Glu Gln Tyr Glu Arg Val Leu Ala Glu Asn Thr Arg Pro Ser
        1410                1415                1420

Gln Met Arg Lys Leu Phe Ser Leu Ser Gln Ser Trp Asp Arg Lys Cys
1425                1430                1435                1440

Lys Asp Gly Leu Tyr Gln Ala Leu Lys Glu Thr His Pro His Leu Ile
            1445                1450                1455

Met Glu Leu Trp Glu Lys Gly Ser Lys Lys Gly Leu Leu Pro Leu Ser
            1460                1465                1470

Ser

<210> SEQ ID NO 3
<211> LENGTH: 4200
<212> TYPE: DNA
<213> ORGANISM: Homo sapiens
<220> FEATURE:
<221> NAME/KEY: CDS
<222> LOCATION: (1)..(4197)

<400> SEQUENCE: 3
```

-continued

| | |
|---|---|
| atg gct ggc gga gcc tgg ggc cgc ctg gcc tgt tac ttg gag ttc ctg<br>Met Ala Gly Gly Ala Trp Gly Arg Leu Ala Cys Tyr Leu Glu Phe Leu<br>1                   5                     10                  15 | 48 |
| aag aag gag gag ctg aag gag ttc cag ctt ctg ctc gcc aat aaa gcg<br>Lys Lys Glu Glu Leu Lys Glu Phe Gln Leu Leu Leu Ala Asn Lys Ala<br>               20                     25                     30 | 96 |
| cac tcc agg agc tct tcg ggt gag aca ccc gct cag cca gag aag acg<br>His Ser Arg Ser Ser Ser Gly Glu Thr Pro Ala Gln Pro Glu Lys Thr<br>          35                     40                     45 | 144 |
| agt ggc atg gag gtg gcc tcg tac ctg gtg gct cag tat ggg gag cag<br>Ser Gly Met Glu Val Ala Ser Tyr Leu Val Ala Gln Tyr Gly Glu Gln<br>50                     55                     60 | 192 |
| cgg gcc tgg gac cta gcc ctc cat acc tgg gag cag atg ggg ctg agg<br>Arg Ala Trp Asp Leu Ala Leu His Thr Trp Glu Gln Met Gly Leu Arg<br>65                     70                     75                     80 | 240 |
| tca ctg tgc gcc caa gcc cag gaa ggg gca ggc cac tct ccc tca ttc<br>Ser Leu Cys Ala Gln Ala Gln Glu Gly Ala Gly His Ser Pro Ser Phe<br>                         85                     90                     95 | 288 |
| ccc tac agc cca agt gaa ccc cac ctg ggg tct ccc agc caa ccc acc<br>Pro Tyr Ser Pro Ser Glu Pro His Leu Gly Ser Pro Ser Gln Pro Thr<br>                100                    105                   110 | 336 |
| tcc acc gca gtg cta atg ccc tgg atc cat gaa ttg ccg gcg ggg tgc<br>Ser Thr Ala Val Leu Met Pro Trp Ile His Glu Leu Pro Ala Gly Cys<br>          115                    120                    125 | 384 |
| acc cag ggc tca gag aga agg gtt ttg aga cag ctg cct gac aca tct<br>Thr Gln Gly Ser Glu Arg Arg Val Leu Arg Gln Leu Pro Asp Thr Ser<br>130                    135                    140 | 432 |
| gga cgc cgc tgg aga gaa atc tct gcc tca ctc ctc tac caa gct ctt<br>Gly Arg Arg Trp Arg Glu Ile Ser Ala Ser Leu Leu Tyr Gln Ala Leu<br>145                    150                    155                    160 | 480 |
| cca agc tcc cca gac cat gag tct cca agc cag gag tca ccc aac gcc<br>Pro Ser Ser Pro Asp His Glu Ser Pro Ser Gln Glu Ser Pro Asn Ala<br>                165                    170                    175 | 528 |
| ccc aca tcc aca gca gtg ctg ggg agc tgg gga tcc cca cct cag ccc<br>Pro Thr Ser Thr Ala Val Leu Gly Ser Trp Gly Ser Pro Pro Gln Pro<br>          180                    185                    190 | 576 |
| agc cta gca ccc aga gag cag gag gct cct ggg acc caa tgg cct ctg<br>Ser Leu Ala Pro Arg Glu Gln Glu Ala Pro Gly Thr Gln Trp Pro Leu<br>195                    200                    205 | 624 |
| gat gaa acg tca gga att tac tac aca gaa atc aga gaa aga gag aga<br>Asp Glu Thr Ser Gly Ile Tyr Tyr Thr Glu Ile Arg Glu Arg Glu Arg<br>210                    215                    220 | 672 |
| gag aaa tca gag aaa ggc agg ccc cca tgg gca gcg gtg gta gga acg<br>Glu Lys Ser Glu Lys Gly Arg Pro Pro Trp Ala Ala Val Val Gly Thr<br>225                    230                    235                    240 | 720 |
| ccc cca cag gcg cac acc agc cta cag ccc cac cac cac cca tgg gag<br>Pro Pro Gln Ala His Thr Ser Leu Gln Pro His His His Pro Trp Glu<br>                245                    250                    255 | 768 |
| cct tct gtg aga gag agc ctc tgt tcc aca tgg ccc tgg aaa aat gag<br>Pro Ser Val Arg Glu Ser Leu Cys Ser Thr Trp Pro Trp Lys Asn Glu<br>          260                    265                    270 | 816 |
| gat ttt aac caa aaa ttc aca cag ctg cta ctt cta caa aga cct cac<br>Asp Phe Asn Gln Lys Phe Thr Gln Leu Leu Leu Leu Gln Arg Pro His<br>275                    280                    285 | 864 |
| ccc aga agc caa gat ccc ctg gtc aag aga agc tgg cct gat tat gtg<br>Pro Arg Ser Gln Asp Pro Leu Val Lys Arg Ser Trp Pro Asp Tyr Val<br>290                    295                    300 | 912 |
| gag gag aat cga gga cat tta att gag atc aga gac tta ttt ggc cca<br>Glu Glu Asn Arg Gly His Leu Ile Glu Ile Arg Asp Leu Phe Gly Pro | 960 |

```
ggc ctg gat acc caa gaa cct cgc ata gtc ata ctg cag ggg gct gct    1008
Gly Leu Asp Thr Gln Glu Pro Arg Ile Val Ile Leu Gln Gly Ala Ala
                325                 330                 335 gga att ggg aag tca aca ctg gcc agg cag gtg aag gaa gcc tgg ggg    1056
Gly Ile Gly Lys Ser Thr Leu Ala Arg Gln Val Lys Glu Ala Trp Gly
            340                 345                 350 aga ggc cag ctg tat ggg gac cgc ttc cag cat gtc ttc tac ttc agc    1104
Arg Gly Gln Leu Tyr Gly Asp Arg Phe Gln His Val Phe Tyr Phe Ser
        355                 360                 365 tgc aga gag ctg gcc cag tcc aag gtg gtg agt ctc gct gag ctc atc    1152
Cys Arg Glu Leu Ala Gln Ser Lys Val Val Ser Leu Ala Glu Leu Ile
    370                 375                 380 gga aaa gat ggg aca gcc act ccg gct ccc att aga cag atc ctg tct    1200
Gly Lys Asp Gly Thr Ala Thr Pro Ala Pro Ile Arg Gln Ile Leu Ser
385                 390                 395                 400 agg cca gag cgg ctg ctc ttc atc ctc gat ggt gta gat gag cca gga    1248
Arg Pro Glu Arg Leu Leu Phe Ile Leu Asp Gly Val Asp Glu Pro Gly
                405                 410                 415 tgg gtc ttg cag gag ccg agt tct gag ctc tgt ctg cac tgg agc cag    1296
Trp Val Leu Gln Glu Pro Ser Ser Glu Leu Cys Leu His Trp Ser Gln
            420                 425                 430 cca cag ccg gcg gat gca ctg ctg ggc agt ttg ctg ggg aaa act ata    1344
Pro Gln Pro Ala Asp Ala Leu Leu Gly Ser Leu Leu Gly Lys Thr Ile
        435                 440                 445 ctt ccc gag gca tcc ttc ctg atc acg gct cgg acc aca gct ctg cag    1392
Leu Pro Glu Ala Ser Phe Leu Ile Thr Ala Arg Thr Thr Ala Leu Gln
    450                 455                 460 aac ctc att cct tct ttg gag cag gca cgt tgg gta gag gtc ctg ggg    1440
Asn Leu Ile Pro Ser Leu Glu Gln Ala Arg Trp Val Glu Val Leu Gly
465                 470                 475                 480 ttc tct gag tcc agc agg aag gaa tat ttc tac aga tat ttc aca gat    1488
Phe Ser Glu Ser Ser Arg Lys Glu Tyr Phe Tyr Arg Tyr Phe Thr Asp
                485                 490                 495 gaa agg caa gca att aga gcc ttt agg ttg gtc aaa tca aac aaa gag    1536
Glu Arg Gln Ala Ile Arg Ala Phe Arg Leu Val Lys Ser Asn Lys Glu
            500                 505                 510 ctc tgg gcc ctg tgt ctt gtg ccc tgg gtg tcc tgg ctg gcc tgc act    1584
Leu Trp Ala Leu Cys Leu Val Pro Trp Val Ser Trp Leu Ala Cys Thr
        515                 520                 525 tgc ctg atg cag cag atg aag cgg aag gaa aaa ctc aca ctg act tcc    1632
Cys Leu Met Gln Gln Met Lys Arg Lys Glu Lys Leu Thr Leu Thr Ser
    530                 535                 540 aag acc acc aca acc ctc tgt cta cat tac ctt gcc cag gct ctc caa    1680
Lys Thr Thr Thr Thr Leu Cys Leu His Tyr Leu Ala Gln Ala Leu Gln
545                 550                 555                 560 gct cag cca ttg gga ccc cag ctc aga gac ctc tgc tct ctg gct gct    1728
Ala Gln Pro Leu Gly Pro Gln Leu Arg Asp Leu Cys Ser Leu Ala Ala
                565                 570                 575 gag ggc atc tgg caa aaa aag acc ctt ttc agt cca gat gac ctc agg    1776
Glu Gly Ile Trp Gln Lys Lys Thr Leu Phe Ser Pro Asp Asp Leu Arg
            580                 585                 590 aag cat ggg tta gat ggg gcc atc atc tcc acc ttc ttg aag atg ggt    1824
Lys His Gly Leu Asp Gly Ala Ile Ile Ser Thr Phe Leu Lys Met Gly
        595                 600                 605 att ctt caa gag cac ccc atc cct ctg agc tac agc ttc att cac ctc    1872
Ile Leu Gln Glu His Pro Ile Pro Leu Ser Tyr Ser Phe Ile His Leu
    610                 615                 620 tgt ttc caa gag ttc ttt gca gca atg tcc tat gtc ttg gag gat gag    1920
```

```
Cys Phe Gln Glu Phe Phe Ala Ala Met Ser Tyr Val Leu Glu Asp Glu
625                 630                 635                 640 aag ggg aga ggt aaa cat tct aat tgc atc ata gat ttg gaa aag acg      1968
Lys Gly Arg Gly Lys His Ser Asn Cys Ile Ile Asp Leu Glu Lys Thr
                645                 650                 655 cta gaa gca tat gga ata cat ggc ctg ttt ggg gca tca acc aca cgt      2016
Leu Glu Ala Tyr Gly Ile His Gly Leu Phe Gly Ala Ser Thr Thr Arg
            660                 665                 670 ttc cta ttg ggc ctg tta agt gat gag ggg gag aga gag atg gag aac      2064
Phe Leu Leu Gly Leu Leu Ser Asp Glu Gly Glu Arg Glu Met Glu Asn
        675                 680                 685 atc ttt cac tgc cgg ctg tct cag ggg agg aac ctg atg cag tgg gtc      2112
Ile Phe His Cys Arg Leu Ser Gln Gly Arg Asn Leu Met Gln Trp Val
    690                 695                 700 ccg tcc ctg cag ctg ctg ctg cag cca cac tct ctg gag tcc ctc cac      2160
Pro Ser Leu Gln Leu Leu Leu Gln Pro His Ser Leu Glu Ser Leu His
705                 710                 715                 720 tgc ttg tac gag act cgg aac aaa acg ttc ctg aca caa gtg atg gcc      2208
Cys Leu Tyr Glu Thr Arg Asn Lys Thr Phe Leu Thr Gln Val Met Ala
                725                 730                 735 cat ttc gaa gaa atg ggc atg tgt gta gaa aca gac atg gag ctc tta      2256
His Phe Glu Glu Met Gly Met Cys Val Glu Thr Asp Met Glu Leu Leu
            740                 745                 750 gtg tgc act ttc tgc att aaa ttc agc cgc cac gtg aag aag ctt cag      2304
Val Cys Thr Phe Cys Ile Lys Phe Ser Arg His Val Lys Lys Leu Gln
        755                 760                 765 ctg att gag ggc agg cag cac aga tca aca tgg agc ccc acc atg gta      2352
Leu Ile Glu Gly Arg Gln His Arg Ser Thr Trp Ser Pro Thr Met Val
770                 775                 780 gtc ctg ttc agg tgg gtc cca gtc aca gat gcc tat tgg cag att ctc      2400
Val Leu Phe Arg Trp Val Pro Val Thr Asp Ala Tyr Trp Gln Ile Leu
785                 790                 795                 800 ttc tcc gtc ctc aag gtc acc aga aac ctg aag gag ctg gac cta agt      2448
Phe Ser Val Leu Lys Val Thr Arg Asn Leu Lys Glu Leu Asp Leu Ser
                805                 810                 815 gga aac tcg ctg agc cac tct gca gtg aag agt ctt tgt aag acc ctg      2496
Gly Asn Ser Leu Ser His Ser Ala Val Lys Ser Leu Cys Lys Thr Leu
            820                 825                 830 aga cgc cct cgc tgc ctc ctg gag acc ctg cgg ttg gct ggc tgt ggc      2544
Arg Arg Pro Arg Cys Leu Leu Glu Thr Leu Arg Leu Ala Gly Cys Gly
        835                 840                 845 ctc aca gct gag gac tgc aag gac ctt gcc ttt ggg ctg aga gcc aac      2592
Leu Thr Ala Glu Asp Cys Lys Asp Leu Ala Phe Gly Leu Arg Ala Asn
    850                 855                 860 cag acc ctg acc gag ctg gac ctg agc ttc aat gtg ctc acg gat gct      2640
Gln Thr Leu Thr Glu Leu Asp Leu Ser Phe Asn Val Leu Thr Asp Ala
865                 870                 875                 880 gga gcc aaa cac ctt tgc cag aga ctg aga cag ccg agc tgc aag cta      2688
Gly Ala Lys His Leu Cys Gln Arg Leu Arg Gln Pro Ser Cys Lys Leu
                885                 890                 895 cag cga ctg cag ctg gtc agc tgt ggc ctc acg tct gac tgc tgc cag      2736
Gln Arg Leu Gln Leu Val Ser Cys Gly Leu Thr Ser Asp Cys Cys Gln
            900                 905                 910 gac ctg gcc tct gtg ctt agt gcc agc ccc agc ctg aag gag cta gac      2784
Asp Leu Ala Ser Val Leu Ser Ala Ser Pro Ser Leu Lys Glu Leu Asp
        915                 920                 925 ctg cag cag aac aac ctg gat gac gtt ggc gtg cga ctg ctc tgt gag      2832
Leu Gln Gln Asn Asn Leu Asp Asp Val Gly Val Arg Leu Leu Cys Glu
    930                 935                 940
```

-continued

| | |
|---|---|
| ggg ctc agg cat cct gcc tgc aaa ctc ata cgc tgg gaa cca agt<br>Gly Leu Arg His Pro Ala Cys Lys Leu Ile Arg Leu Gly Lys Pro Ser<br>945                     950                    955                   960 | 2880 |
| gtg atg acc cct act gag ggc ctg gat acg gga gag atg agt aat agc<br>Val Met Thr Pro Thr Glu Gly Leu Asp Thr Gly Glu Met Ser Asn Ser<br>                965                    970                    975 | 2928 |
| aca tcc tca ctc aag cgg cag aga ctc gga tca gag agg gcg gct tcc<br>Thr Ser Ser Leu Lys Arg Gln Arg Leu Gly Ser Glu Arg Ala Ala Ser<br>            980                    985                    990 | 2976 |
| cat gtt gct cag gct aat ctc aaa ctc ctg gac gtg agc aag atc ttc<br>His Val Ala Gln Ala Asn Leu Lys Leu Leu Asp Val Ser Lys Ile Phe<br>995                     1000                 1005 | 3024 |
| cca att gct gag att gca gag gaa agc tcc cca gag gta gta ccg gtg<br>Pro Ile Ala Glu Ile Ala Glu Glu Ser Ser Pro Glu Val Val Pro Val<br>1010                  1015                 1020 | 3072 |
| gaa ctc ttg tgc gtg cct tct cct gcc tct caa ggg gac ctg cat acg<br>Glu Leu Leu Cys Val Pro Ser Pro Ala Ser Gln Gly Asp Leu His Thr<br>1025                  1030                 1035                 1040 | 3120 |
| aag cct ttg ggg act gac gat gac ttc tgg ggc ccc acg ggg cct gtg<br>Lys Pro Leu Gly Thr Asp Asp Asp Phe Trp Gly Pro Thr Gly Pro Val<br>                 1045                 1050                 1055 | 3168 |
| gct act gag gta gtt gac aaa gaa aag aac ttg tac cga gtt cac ttc<br>Ala Thr Glu Val Val Asp Lys Glu Lys Asn Leu Tyr Arg Val His Phe<br>1060                  1065                 1070 | 3216 |
| cct gta gct ggc tcc tac cgc tgg ccc aac acg ggt ctc tgc ttt gtg<br>Pro Val Ala Gly Ser Tyr Arg Trp Pro Asn Thr Gly Leu Cys Phe Val<br>1075                  1080                 1085 | 3264 |
| atg aga gaa gcg gtg acc gtt gag att gaa ttc tgt gtg tgg gac cag<br>Met Arg Glu Ala Val Thr Val Glu Ile Glu Phe Cys Val Trp Asp Gln<br>1090                  1095                 1100 | 3312 |
| ttc ctg ggt gag atc aac cca cag cac agc tgg atg gtg gca ggg cct<br>Phe Leu Gly Glu Ile Asn Pro Gln His Ser Trp Met Val Ala Gly Pro<br>1105                  1110                 1115                 1120 | 3360 |
| ctg ctg gac atc aag gct gag cct gga gct gtg gaa gct gtg cac ctc<br>Leu Leu Asp Ile Lys Ala Glu Pro Gly Ala Val Glu Ala Val His Leu<br>                 1125                 1130                 1135 | 3408 |
| cct cac ttt gtg gct ctc caa ggg ggc cat gtg gac aca tcc ctg ttc<br>Pro His Phe Val Ala Leu Gln Gly Gly His Val Asp Thr Ser Leu Phe<br>1140                  1145                 1150 | 3456 |
| caa atg gcc cac ttt aaa gag gag ggg atg ctc ctg gag aag cca gcc<br>Gln Met Ala His Phe Lys Glu Glu Gly Met Leu Leu Glu Lys Pro Ala<br>1155                  1160                 1165 | 3504 |
| agg gtg gag ctg cat cac ata gtt ctg gaa aac ccc agc ttc tcc ccc<br>Arg Val Glu Leu His His Ile Val Leu Glu Asn Pro Ser Phe Ser Pro<br>1170                  1175                 1180 | 3552 |
| ttg gga gtc ctc ctg aaa atg atc cat aat gcc ctg cgc ttc att ccc<br>Leu Gly Val Leu Leu Lys Met Ile His Asn Ala Leu Arg Phe Ile Pro<br>1185                  1190                 1195                 1200 | 3600 |
| gtc acc tct gtg gtg ttg ctt tac cac cgc gtc cat cct gag gaa gtc<br>Val Thr Ser Val Val Leu Leu Tyr His Arg Val His Pro Glu Glu Val<br>                 1205                 1210                 1215 | 3648 |
| acc ttc cac ctc tac ctg atc cca agt gac tgc tcc att cgg aag gaa<br>Thr Phe His Leu Tyr Leu Ile Pro Ser Asp Cys Ser Ile Arg Lys Glu<br>1220                  1225                 1230 | 3696 |
| ctg gag ctc tgc tat cga agc cct gga gaa gac cag ctg ttc tcg gag<br>Leu Glu Leu Cys Tyr Arg Ser Pro Gly Glu Asp Gln Leu Phe Ser Glu<br>1235                  1240                 1245 | 3744 |
| ttc tac gtt ggc cac ttg gga tca ggg atc agg ctg caa gtg aaa gac<br>Phe Tyr Val Gly His Leu Gly Ser Gly Ile Arg Leu Gln Val Lys Asp<br>1250                  1255                 1260 | 3792 |

-continued

```
aag aaa gat gag act ctg gtg tgg gag gcc ttg gtg aaa cca gga gat      3840
Lys Lys Asp Glu Thr Leu Val Trp Glu Ala Leu Val Lys Pro Gly Asp
1265                1270                1275                1280 ctc atg cct gca act act ctg atc cct cca gcc cgc ata gcc gta cct      3888
Leu Met Pro Ala Thr Thr Leu Ile Pro Pro Ala Arg Ile Ala Val Pro
            1285                1290                1295 tca cct ctg gat gcc ccg cag ttg ctg cac ttt gtg gac cag tat cga      3936
Ser Pro Leu Asp Ala Pro Gln Leu Leu His Phe Val Asp Gln Tyr Arg
        1300                1305                1310 gag cag ctg ata gcc cga gtg aca tcg gtg gag gtt gtc ttg gac aaa      3984
Glu Gln Leu Ile Ala Arg Val Thr Ser Val Glu Val Val Leu Asp Lys
    1315                1320                1325 ctg cat gga cag gtg ctg agc cag gag cag tac gag agg gtg ctg gct      4032
Leu His Gly Gln Val Leu Ser Gln Glu Gln Tyr Glu Arg Val Leu Ala
 1330                1335                1340 gag aac acg agg ccc agc cag atg cgg aag ctg ttc agc ttg agc cag      4080
Glu Asn Thr Arg Pro Ser Gln Met Arg Lys Leu Phe Ser Leu Ser Gln
1345                1350                1355                1360 tcc tgg gac cgg aag tgc aaa gat gga ctc tac caa gcc ctg aag gag      4128
Ser Trp Asp Arg Lys Cys Lys Asp Gly Leu Tyr Gln Ala Leu Lys Glu
            1365                1370                1375 acc cat cct cac ctc att atg gaa ctc tgg gag aag ggc agc aaa aag      4176
Thr His Pro His Leu Ile Met Glu Leu Trp Glu Lys Gly Ser Lys Lys
        1380                1385                1390 gga ctc ctg cca ctc agc agc tga                                      4200
Gly Leu Leu Pro Leu Ser Ser
    1395

<210> SEQ ID NO 4
<211> LENGTH: 1399
<212> TYPE: PRT
<213> ORGANISM: Homo sapiens

<400> SEQUENCE: 4

Met Ala Gly Gly Ala Trp Gly Arg Leu Ala Cys Tyr Leu Glu Phe Leu
 1               5                  10                  15

Lys Lys Glu Glu Leu Lys Glu Phe Gln Leu Leu Leu Ala Asn Lys Ala
                20                  25                  30

His Ser Arg Ser Ser Ser Gly Glu Thr Pro Ala Gln Pro Glu Lys Thr
            35                  40                  45

Ser Gly Met Glu Val Ala Ser Tyr Leu Val Ala Gln Tyr Gly Glu Gln
        50                  55                  60

Arg Ala Trp Asp Leu Ala Leu His Thr Trp Glu Gln Met Gly Leu Arg
    65                  70                  75                  80

Ser Leu Cys Ala Gln Ala Gln Glu Gly Ala Gly His Ser Pro Ser Phe
                85                  90                  95

Pro Tyr Ser Pro Ser Glu Pro His Leu Gly Ser Pro Ser Gln Pro Thr
                100                 105                 110

Ser Thr Ala Val Leu Met Pro Trp Ile His Glu Leu Pro Ala Gly Cys
            115                 120                 125

Thr Gln Gly Ser Glu Arg Arg Val Leu Arg Gln Leu Pro Asp Thr Ser
        130                 135                 140

Gly Arg Arg Trp Arg Glu Ile Ser Ala Ser Leu Leu Tyr Gln Ala Leu
    145                 150                 155                 160

Pro Ser Ser Pro Asp His Glu Ser Pro Ser Gln Glu Ser Pro Asn Ala
                165                 170                 175

Pro Thr Ser Thr Ala Val Leu Gly Ser Trp Gly Ser Pro Pro Gln Pro
```

-continued

```
                180                 185                 190
Ser Leu Ala Pro Arg Glu Gln Glu Ala Pro Gly Thr Gln Trp Pro Leu
            195                 200                 205

Asp Glu Thr Ser Gly Ile Tyr Tyr Thr Glu Ile Arg Glu Arg Glu Arg
210                 215                 220

Glu Lys Ser Glu Lys Gly Arg Pro Pro Trp Ala Ala Val Val Gly Thr
225                 230                 235                 240

Pro Pro Gln Ala His Thr Ser Leu Gln Pro His His Pro Trp Glu
                245                 250                 255

Pro Ser Val Arg Glu Ser Leu Cys Ser Thr Trp Pro Trp Lys Asn Glu
            260                 265                 270

Asp Phe Asn Gln Lys Phe Thr Gln Leu Leu Leu Gln Arg Pro His
            275                 280                 285

Pro Arg Ser Gln Asp Pro Leu Val Lys Arg Ser Trp Pro Asp Tyr Val
290                 295                 300

Glu Glu Asn Arg Gly His Leu Ile Glu Ile Arg Asp Leu Phe Gly Pro
305                 310                 315                 320

Gly Leu Asp Thr Gln Glu Pro Arg Ile Val Ile Leu Gln Gly Ala Ala
                325                 330                 335

Gly Ile Gly Lys Ser Thr Leu Ala Arg Gln Val Lys Glu Ala Trp Gly
                340                 345                 350

Arg Gly Gln Leu Tyr Gly Asp Arg Phe Gln His Val Phe Tyr Phe Ser
            355                 360                 365

Cys Arg Glu Leu Ala Gln Ser Lys Val Val Ser Leu Ala Glu Leu Ile
    370                 375                 380

Gly Lys Asp Gly Thr Ala Thr Pro Ala Pro Ile Arg Gln Ile Leu Ser
385                 390                 395                 400

Arg Pro Glu Arg Leu Leu Phe Ile Leu Asp Gly Val Asp Glu Pro Gly
                405                 410                 415

Trp Val Leu Gln Glu Pro Ser Ser Glu Leu Cys Leu His Trp Ser Gln
                420                 425                 430

Pro Gln Pro Ala Asp Ala Leu Leu Gly Ser Leu Leu Gly Lys Thr Ile
            435                 440                 445

Leu Pro Glu Ala Ser Phe Leu Ile Thr Ala Arg Thr Thr Ala Leu Gln
450                 455                 460

Asn Leu Ile Pro Ser Leu Glu Gln Ala Arg Trp Val Glu Val Leu Gly
465                 470                 475                 480

Phe Ser Glu Ser Ser Arg Lys Glu Tyr Phe Tyr Arg Tyr Phe Thr Asp
                485                 490                 495

Glu Arg Gln Ala Ile Arg Ala Phe Arg Leu Val Lys Ser Asn Lys Glu
                500                 505                 510

Leu Trp Ala Leu Cys Leu Val Pro Trp Val Ser Trp Leu Ala Cys Thr
            515                 520                 525

Cys Leu Met Gln Gln Met Lys Arg Lys Glu Lys Leu Thr Leu Thr Ser
            530                 535                 540

Lys Thr Thr Thr Thr Leu Cys Leu His Tyr Leu Ala Gln Ala Leu Gln
545                 550                 555                 560

Ala Gln Pro Leu Gly Pro Gln Leu Arg Asp Leu Cys Ser Leu Ala Ala
                565                 570                 575

Glu Gly Ile Trp Gln Lys Lys Thr Leu Phe Ser Pro Asp Asp Leu Arg
            580                 585                 590

Lys His Gly Leu Asp Gly Ala Ile Ile Ser Thr Phe Leu Lys Met Gly
            595                 600                 605
```

-continued

```
Ile Leu Gln Glu His Pro Ile Pro Leu Ser Tyr Ser Phe Ile His Leu
    610                 615                 620
Cys Phe Gln Glu Phe Phe Ala Ala Met Ser Tyr Val Leu Glu Asp Glu
625                 630                 635                 640
Lys Gly Arg Gly Lys His Ser Asn Cys Ile Ile Asp Leu Glu Lys Thr
                645                 650                 655
Leu Glu Ala Tyr Gly Ile His Gly Leu Phe Gly Ala Ser Thr Thr Arg
                660                 665                 670
Phe Leu Leu Gly Leu Leu Ser Asp Glu Gly Glu Arg Glu Met Glu Asn
            675                 680                 685
Ile Phe His Cys Arg Leu Ser Gln Gly Arg Asn Leu Met Gln Trp Val
            690                 695                 700
Pro Ser Leu Gln Leu Leu Leu Gln Pro His Ser Leu Glu Ser Leu His
705                 710                 715                 720
Cys Leu Tyr Glu Thr Arg Asn Lys Thr Phe Leu Thr Gln Val Met Ala
                725                 730                 735
His Phe Glu Glu Met Gly Met Cys Val Glu Thr Asp Met Glu Leu Leu
                740                 745                 750
Val Cys Thr Phe Cys Ile Lys Phe Ser Arg His Val Lys Lys Leu Gln
            755                 760                 765
Leu Ile Glu Gly Arg Gln His Arg Ser Thr Trp Ser Pro Thr Met Val
770                 775                 780
Val Leu Phe Arg Trp Val Pro Val Thr Asp Ala Tyr Trp Gln Ile Leu
785                 790                 795                 800
Phe Ser Val Leu Lys Val Thr Arg Asn Leu Lys Glu Leu Asp Leu Ser
                805                 810                 815
Gly Asn Ser Leu Ser His Ser Ala Val Lys Ser Leu Cys Lys Thr Leu
                820                 825                 830
Arg Arg Pro Arg Cys Leu Leu Glu Thr Leu Arg Leu Ala Gly Cys Gly
            835                 840                 845
Leu Thr Ala Glu Asp Cys Lys Asp Leu Ala Phe Gly Leu Arg Ala Asn
850                 855                 860
Gln Thr Leu Thr Glu Leu Asp Leu Ser Phe Asn Val Leu Thr Asp Ala
865                 870                 875                 880
Gly Ala Lys His Leu Cys Gln Arg Leu Arg Gln Pro Ser Cys Lys Leu
                885                 890                 895
Gln Arg Leu Gln Leu Val Ser Cys Gly Leu Thr Ser Asp Cys Cys Gln
            900                 905                 910
Asp Leu Ala Ser Val Leu Ser Ala Ser Pro Ser Leu Lys Glu Leu Asp
            915                 920                 925
Leu Gln Gln Asn Asn Leu Asp Asp Val Gly Val Arg Leu Leu Cys Glu
        930                 935                 940
Gly Leu Arg His Pro Ala Cys Lys Leu Ile Arg Leu Gly Lys Pro Ser
945                 950                 955                 960
Val Met Thr Pro Thr Glu Gly Leu Asp Thr Gly Glu Met Ser Asn Ser
                965                 970                 975
Thr Ser Ser Leu Lys Arg Gln Arg Leu Gly Ser Glu Arg Ala Ala Ser
            980                 985                 990
His Val Ala Gln Ala Asn Leu Lys Leu Leu Asp Val Ser Lys Ile Phe
        995                 1000                1005
Pro Ile Ala Glu Ile Ala Glu Glu Ser Ser Pro Glu Val Val Pro Val
    1010                1015                1020
```

-continued

Glu Leu Leu Cys Val Pro Ser Pro Ala Ser Gln Gly Asp Leu His Thr
1025                1030                1035                1040

Lys Pro Leu Gly Thr Asp Asp Phe Trp Gly Pro Thr Gly Pro Val
            1045                1050                1055

Ala Thr Glu Val Val Asp Lys Glu Lys Asn Leu Tyr Arg Val His Phe
                1060                1065                1070

Pro Val Ala Gly Ser Tyr Arg Trp Pro Asn Thr Gly Leu Cys Phe Val
    1075                1080                1085

Met Arg Glu Ala Val Thr Val Glu Ile Glu Phe Cys Val Trp Asp Gln
1090                1095                1100

Phe Leu Gly Glu Ile Asn Pro Gln His Ser Trp Met Val Ala Gly Pro
1105                1110                1115                1120

Leu Leu Asp Ile Lys Ala Glu Pro Gly Ala Val Glu Ala Val His Leu
            1125                1130                1135

Pro His Phe Val Ala Leu Gln Gly Gly His Val Asp Thr Ser Leu Phe
            1140                1145                1150

Gln Met Ala His Phe Lys Glu Glu Gly Met Leu Leu Glu Lys Pro Ala
        1155                1160                1165

Arg Val Glu Leu His His Ile Val Leu Glu Asn Pro Ser Phe Ser Pro
1170                1175                1180

Leu Gly Val Leu Leu Lys Met Ile His Asn Ala Leu Arg Phe Ile Pro
1185                1190                1195                1200

Val Thr Ser Val Val Leu Leu Tyr His Arg Val His Pro Glu Glu Val
                1205                1210                1215

Thr Phe His Leu Tyr Leu Ile Pro Ser Asp Cys Ser Ile Arg Lys Glu
            1220                1225                1230

Leu Glu Leu Cys Tyr Arg Ser Pro Gly Glu Asp Gln Leu Phe Ser Glu
        1235                1240                1245

Phe Tyr Val Gly His Leu Gly Ser Gly Ile Arg Leu Gln Val Lys Asp
1250                1255                1260

Lys Lys Asp Glu Thr Leu Val Trp Glu Ala Leu Val Lys Pro Gly Asp
1265                1270                1275                1280

Leu Met Pro Ala Thr Thr Leu Ile Pro Pro Ala Arg Ile Ala Val Pro
            1285                1290                1295

Ser Pro Leu Asp Ala Pro Gln Leu Leu His Phe Val Asp Gln Tyr Arg
            1300                1305                1310

Glu Gln Leu Ile Ala Arg Val Thr Ser Val Glu Val Val Leu Asp Lys
        1315                1320                1325

Leu His Gly Gln Val Leu Ser Gln Glu Gln Tyr Glu Arg Val Leu Ala
1330                1335                1340

Glu Asn Thr Arg Pro Ser Gln Met Arg Lys Leu Phe Ser Leu Ser Gln
1345                1350                1355                1360

Ser Trp Asp Arg Lys Cys Lys Asp Gly Leu Tyr Gln Ala Leu Lys Glu
            1365                1370                1375

Thr His Pro His Leu Ile Met Glu Leu Trp Glu Lys Gly Ser Lys Lys
            1380                1385                1390

Gly Leu Leu Pro Leu Ser Ser
        1395

<210> SEQ ID NO 5
<211> LENGTH: 4332
<212> TYPE: DNA
<213> ORGANISM: Homo sapiens
<220> FEATURE:
<221> NAME/KEY: CDS -continued

<210> LOCATION: (1)..(4332)

<400> SEQUENCE: 5

| | | |
|---|---|---|
| atg gct ggc gga gcc tgg ggc cgc ctg gcc tgt tac ttg gag ttc ctg<br>Met Ala Gly Gly Ala Trp Gly Arg Leu Ala Cys Tyr Leu Glu Phe Leu<br>1               5                  10                  15 | | 48 |
| aag aag gag gag ctg aag gag ttc cag ctt ctg ctc gcc aat aaa gcg<br>Lys Lys Glu Glu Leu Lys Glu Phe Gln Leu Leu Leu Ala Asn Lys Ala<br>            20                  25                  30 | | 96 |
| cac tcc agg agc tct tcg ggt gag aca ccc gct cag cca gag aag acg<br>His Ser Arg Ser Ser Ser Gly Glu Thr Pro Ala Gln Pro Glu Lys Thr<br>        35                  40                  45 | | 144 |
| agt ggc atg gag gtg gcc tcg tac ctg gtg gct cag tat ggg gag cag<br>Ser Gly Met Glu Val Ala Ser Tyr Leu Val Ala Gln Tyr Gly Glu Gln<br>    50                  55                  60 | | 192 |
| cgg gcc tgg gac cta gcc ctc cat acc tgg gag cag atg ggg ctg agg<br>Arg Ala Trp Asp Leu Ala Leu His Thr Trp Glu Gln Met Gly Leu Arg<br>65                  70                  75                  80 | | 240 |
| tca ctg tgc gcc caa gcc cag gaa ggg gca ggc cac tct ccc tca ttc<br>Ser Leu Cys Ala Gln Ala Gln Glu Gly Ala Gly His Ser Pro Ser Phe<br>                85                  90                  95 | | 288 |
| ccc tac agc cca agt gaa ccc cac ctg ggg tct ccc agc caa ccc acc<br>Pro Tyr Ser Pro Ser Glu Pro His Leu Gly Ser Pro Ser Gln Pro Thr<br>            100                 105                 110 | | 336 |
| tcc acc gca gtg cta atg ccc tgg atc cat gaa ttg ccg gcg ggg tgc<br>Ser Thr Ala Val Leu Met Pro Trp Ile His Glu Leu Pro Ala Gly Cys<br>        115                 120                 125 | | 384 |
| acc cag ggc tca gag aga agg gtt ttg aga cag ctg cct gac aca tct<br>Thr Gln Gly Ser Glu Arg Arg Val Leu Arg Gln Leu Pro Asp Thr Ser<br>    130                 135                 140 | | 432 |
| gga cgc cgc tgg aga gaa atc tct gcc tca ctc ctc tac caa gct ctt<br>Gly Arg Arg Trp Arg Glu Ile Ser Ala Ser Leu Leu Tyr Gln Ala Leu<br>145                 150                 155                 160 | | 480 |
| cca agc tcc cca gac cat gag tct cca agc cag gag tca ccc aac gcc<br>Pro Ser Ser Pro Asp His Glu Ser Pro Ser Gln Glu Ser Pro Asn Ala<br>                165                 170                 175 | | 528 |
| ccc aca tcc aca gca gtg ctg ggg agc tgg gga tcc cca cct cag ccc<br>Pro Thr Ser Thr Ala Val Leu Gly Ser Trp Gly Ser Pro Pro Gln Pro<br>            180                 185                 190 | | 576 |
| agc cta gca ccc aga gag cag gag gct cct ggg acc caa tgg cct ctg<br>Ser Leu Ala Pro Arg Glu Gln Glu Ala Pro Gly Thr Gln Trp Pro Leu<br>        195                 200                 205 | | 624 |
| gat gaa acg tca gga att tac tac aca gaa atc aga gaa aga gag aga<br>Asp Glu Thr Ser Gly Ile Tyr Tyr Thr Glu Ile Arg Glu Arg Glu Arg<br>    210                 215                 220 | | 672 |
| gag aaa tca gag aaa ggc agg ccc cca tgg gca gcg gtg gta gga acg<br>Glu Lys Ser Glu Lys Gly Arg Pro Pro Trp Ala Ala Val Val Gly Thr<br>225                 230                 235                 240 | | 720 |
| ccc cca cag gcg cac acc agc cta cag ccc cac cac cac cca tgg gag<br>Pro Pro Gln Ala His Thr Ser Leu Gln Pro His His His Pro Trp Glu<br>                245                 250                 255 | | 768 |
| cct tct gtg aga gag agc ctc tgt tcc aca tgg ccc tgg aaa aat gag<br>Pro Ser Val Arg Glu Ser Leu Cys Ser Thr Trp Pro Trp Lys Asn Glu<br>            260                 265                 270 | | 816 |
| gat ttt aac caa aaa ttc aca cag ctg cta ctt cta caa aga cct cac<br>Asp Phe Asn Gln Lys Phe Thr Gln Leu Leu Leu Leu Gln Arg Pro His<br>        275                 280                 285 | | 864 |
| ccc aga agc caa gat ccc ctg gtc aag aga agc tgg cct gat tat gtg<br>Pro Arg Ser Gln Asp Pro Leu Val Lys Arg Ser Trp Pro Asp Tyr Val<br>    290                 295                 300 | | 912 |

-continued

| | | |
|---|---|---|
| gag gag aat cga gga cat tta att gag atc aga gac tta ttt ggc cca<br>Glu Glu Asn Arg Gly His Leu Ile Glu Ile Arg Asp Leu Phe Gly Pro<br>305                      310                    315                    320 | 960 |
| ggc ctg gat acc caa gaa cct cgc ata gtc ata ctg cag ggg gct gct<br>Gly Leu Asp Thr Gln Glu Pro Arg Ile Val Ile Leu Gln Gly Ala Ala<br>                    325                    330                    335 | 1008 |
| gga att ggg aag tca aca ctg gcc agg cag gtg aag gaa gcc tgg ggg<br>Gly Ile Gly Lys Ser Thr Leu Ala Arg Gln Val Lys Glu Ala Trp Gly<br>          340                    345                    350 | 1056 |
| aga ggc cag ctg tat ggg gac cgc ttc cag cat gtc ttc tac ttc agc<br>Arg Gly Gln Leu Tyr Gly Asp Arg Phe Gln His Val Phe Tyr Phe Ser<br>355                      360                    365 | 1104 |
| tgc aga gag ctg gcc cag tcc aag gtg gtg agt ctc gct gag ctc atc<br>Cys Arg Glu Leu Ala Gln Ser Lys Val Val Ser Leu Ala Glu Leu Ile<br>370                      375                    380 | 1152 |
| gga aaa gat ggg aca gcc act ccg gct ccc att aga cag atc ctg tct<br>Gly Lys Asp Gly Thr Ala Thr Pro Ala Pro Ile Arg Gln Ile Leu Ser<br>385                      390                    395                    400 | 1200 |
| agg cca gag cgg ctg ctc ttc atc ctc gat ggt gta gat gag cca gga<br>Arg Pro Glu Arg Leu Leu Phe Ile Leu Asp Gly Val Asp Glu Pro Gly<br>                    405                    410                    415 | 1248 |
| tgg gtc ttg cag gag ccg agt tct gag ctc tgt ctg cac tgg agc cag<br>Trp Val Leu Gln Glu Pro Ser Ser Glu Leu Cys Leu His Trp Ser Gln<br>          420                    425                    430 | 1296 |
| cca cag ccg gcg gat gca ctg ctg ggc agt ttg ctg ggg aaa act ata<br>Pro Gln Pro Ala Asp Ala Leu Leu Gly Ser Leu Leu Gly Lys Thr Ile<br>435                      440                    445 | 1344 |
| ctt ccc gag gca tcc ttc ctg atc acg gct cgg acc aca gct ctg cag<br>Leu Pro Glu Ala Ser Phe Leu Ile Thr Ala Arg Thr Thr Ala Leu Gln<br>450                      455                    460 | 1392 |
| aac ctc att cct tct ttg gag cag gca cgt tgg gta gag gtc ctg ggg<br>Asn Leu Ile Pro Ser Leu Glu Gln Ala Arg Trp Val Glu Val Leu Gly<br>465                      470                    475                    480 | 1440 |
| ttc tct gag tcc agc agg aag gaa tat ttc tac aga tat ttc aca gat<br>Phe Ser Glu Ser Ser Arg Lys Glu Tyr Phe Tyr Arg Tyr Phe Thr Asp<br>                    485                    490                    495 | 1488 |
| gaa agg caa gca att aga gcc ttt agg ttg gtc aaa tca aac aaa gag<br>Glu Arg Gln Ala Ile Arg Ala Phe Arg Leu Val Lys Ser Asn Lys Glu<br>          500                    505                    510 | 1536 |
| ctc tgg gcc ctg tgt ctt gtg ccc tgg gtg tcc tgg ctg gcc tgc act<br>Leu Trp Ala Leu Cys Leu Val Pro Trp Val Ser Trp Leu Ala Cys Thr<br>515                      520                    525 | 1584 |
| tgc ctg atg cag cag atg aag cgg aag gaa aaa ctc aca ctg act tcc<br>Cys Leu Met Gln Gln Met Lys Arg Lys Glu Lys Leu Thr Leu Thr Ser<br>530                      535                    540 | 1632 |
| aag acc acc aca acc ctc tgt cta cat tac ctt gcc cag gct ctc caa<br>Lys Thr Thr Thr Thr Leu Cys Leu His Tyr Leu Ala Gln Ala Leu Gln<br>545                      550                    555                    560 | 1680 |
| gct cag cca ttg gga ccc cag ctc aga gac ctc tgc tct ctg gct gct<br>Ala Gln Pro Leu Gly Pro Gln Leu Arg Asp Leu Cys Ser Leu Ala Ala<br>                    565                    570                    575 | 1728 |
| gag ggc atc tgg caa aaa aag acc ctt ttc agt cca gat gac ctc agg<br>Glu Gly Ile Trp Gln Lys Lys Thr Leu Phe Ser Pro Asp Asp Leu Arg<br>          580                    585                    590 | 1776 |
| aag cat ggg tta gat ggg gcc atc atc tcc acc ttc ttg aag atg ggt<br>Lys His Gly Leu Asp Gly Ala Ile Ile Ser Thr Phe Leu Lys Met Gly<br>595                      600                    605 | 1824 |
| att ctt caa gag cac ccc atc cct ctg agc tac agc ttc att cac ctc<br>Ile Leu Gln Glu His Pro Ile Pro Leu Ser Tyr Ser Phe Ile His Leu | 1872 |

```
              610                 615                 620
tgt ttc caa gag ttc ttt gca gca atg tcc tat gtc ttg gag gat gag        1920
Cys Phe Gln Glu Phe Phe Ala Ala Met Ser Tyr Val Leu Glu Asp Glu
625                 630                 635                 640 aag ggg aga ggt aaa cat tct aat tgc atc ata gat ttg gaa aag acg        1968
Lys Gly Arg Gly Lys His Ser Asn Cys Ile Ile Asp Leu Glu Lys Thr
                    645                 650                 655 cta gaa gca tat gga ata cat ggc ctg ttt ggg gca tca acc aca cgt        2016
Leu Glu Ala Tyr Gly Ile His Gly Leu Phe Gly Ala Ser Thr Thr Arg
                660                 665                 670 ttc cta ttg ggc ctg tta agt gat gag ggg gag aga gag atg gag aac        2064
Phe Leu Leu Gly Leu Leu Ser Asp Glu Gly Glu Arg Glu Met Glu Asn
            675                 680                 685 atc ttt cac tgc cgg ctg tct cag ggg agg aac ctg atg cag tgg gtc        2112
Ile Phe His Cys Arg Leu Ser Gln Gly Arg Asn Leu Met Gln Trp Val
        690                 695                 700 ccg tcc ctg cag ctg ctg ctg cag cca cac tct ctg gag tcc ctc cac        2160
Pro Ser Leu Gln Leu Leu Leu Gln Pro His Ser Leu Glu Ser Leu His
705                 710                 715                 720 tgc ttg tac gag act cgg aac aaa acg ttc ctg aca caa gtg atg gcc        2208
Cys Leu Tyr Glu Thr Arg Asn Lys Thr Phe Leu Thr Gln Val Met Ala
                    725                 730                 735 cat ttc gaa gaa atg ggc atg tgt gta gaa aca gac atg gag ctc tta        2256
His Phe Glu Glu Met Gly Met Cys Val Glu Thr Asp Met Glu Leu Leu
                740                 745                 750 gtg tgc act ttc tgc att aaa ttc agc cgc cac gtg aag aag ctt cag        2304
Val Cys Thr Phe Cys Ile Lys Phe Ser Arg His Val Lys Lys Leu Gln
            755                 760                 765 ctg att gag ggc agg cag cac aga tca aca tgg agc ccc acc atg gta        2352
Leu Ile Glu Gly Arg Gln His Arg Ser Thr Trp Ser Pro Thr Met Val
        770                 775                 780 gtc ctg ttc agg tgg gtc cca gtc aca gat gcc tat tgg cag att ctc        2400
Val Leu Phe Arg Trp Val Pro Val Thr Asp Ala Tyr Trp Gln Ile Leu
785                 790                 795                 800 ttc tcc gtc ctc aag gtc acc aga aac ctg aag gag ctg gac cta agt        2448
Phe Ser Val Leu Lys Val Thr Arg Asn Leu Lys Glu Leu Asp Leu Ser
                    805                 810                 815 gga aac tcg ctg agc cac tct gca gtg aag agt ctt tgt aag acc ctg        2496
Gly Asn Ser Leu Ser His Ser Ala Val Lys Ser Leu Cys Lys Thr Leu
                820                 825                 830 aga cgc cct cgc tgc ctc ctg gag acc ctg cgg ttg gct ggc tgt ggc        2544
Arg Arg Pro Arg Cys Leu Leu Glu Thr Leu Arg Leu Ala Gly Cys Gly
            835                 840                 845 ctc aca gct gag gac tgc aag gac ctt gcc ttt ggg ctg aga gcc aac        2592
Leu Thr Ala Glu Asp Cys Lys Asp Leu Ala Phe Gly Leu Arg Ala Asn
850                 855                 860 cag acc ctg acc gag ctg gac ctg agc ttc aat gtg ctc acg gat gct        2640
Gln Thr Leu Thr Glu Leu Asp Leu Ser Phe Asn Val Leu Thr Asp Ala
865                 870                 875                 880 gga gcc aaa cac ctt tgc cag aga ctg aga cag ccg agc tgc aag cta        2688
Gly Ala Lys His Leu Cys Gln Arg Leu Arg Gln Pro Ser Cys Lys Leu
                    885                 890                 895 cag cga ctg cag ctg gtc agc tgt ggc ctc acg tct gac tgc tgc cag        2736
Gln Arg Leu Gln Leu Val Ser Cys Gly Leu Thr Ser Asp Cys Cys Gln
                900                 905                 910 gac ctg gcc tct gtg ctt agt gcc agc ccc agc ctg aag gag cta gac        2784
Asp Leu Ala Ser Val Leu Ser Ala Ser Pro Ser Leu Lys Glu Leu Asp
            915                 920                 925 ctg cag cag aac aac ctg gat gac gtt ggc gtg cga ctg ctc tgt gag        2832
```

-continued

```
        Leu Gln Gln Asn Asn Leu Asp Asp Val Gly Val Arg Leu Leu Cys Glu
            930                 935                 940 ggg ctc agg cat cct gcc tgc aaa ctc ata cgc ctg ggg aaa cca agt              2880
Gly Leu Arg His Pro Ala Cys Lys Leu Ile Arg Leu Gly Lys Pro Ser
945                 950                 955                 960 gtg atg acc cct act gag ggc ctg gat acg gga gag atg agt aat agc              2928
Val Met Thr Pro Thr Glu Gly Leu Asp Thr Gly Glu Met Ser Asn Ser
                965                 970                 975 aca tcc tca ctc aag cgg cag aga ctc gga tca gag agg gcg gct tcc              2976
Thr Ser Ser Leu Lys Arg Gln Arg Leu Gly Ser Glu Arg Ala Ala Ser
            980                 985                 990 cat gtt gct cag gct aat ctc aaa ctc ctg gac gtg agc aag atc ttc              3024
His Val Ala Gln Ala Asn Leu Lys Leu Leu Asp Val Ser Lys Ile Phe
        995                 1000                1005 cca att gct gag att gca gag gaa agc tcc cca gag gta gta ccg gtg              3072
Pro Ile Ala Glu Ile Ala Glu Glu Ser Ser Pro Glu Val Val Pro Val
    1010                1015                1020 gaa ctc ttg tgc gtg cct tct cct gcc tct caa ggg gac ctg cat acg              3120
Glu Leu Leu Cys Val Pro Ser Pro Ala Ser Gln Gly Asp Leu His Thr
1025                1030                1035                1040 aag cct ttg ggg act gac gat gac ttc tgg ggc ccc acg ggg cct gtg              3168
Lys Pro Leu Gly Thr Asp Asp Asp Phe Trp Gly Pro Thr Gly Pro Val
                1045                1050                1055 gct act gag gta gtt gac aaa gaa aag aac ttg tac cga gtt cac ttc              3216
Ala Thr Glu Val Val Asp Lys Glu Lys Asn Leu Tyr Arg Val His Phe
            1060                1065                1070 cct gta gct ggc tcc tac cgc tgg ccc aac acg ggt ctc tgc ttt gtg              3264
Pro Val Ala Gly Ser Tyr Arg Trp Pro Asn Thr Gly Leu Cys Phe Val
        1075                1080                1085 atg aga gaa gcg gtg acc gtt gag att gaa ttc tgt gtg tgg gac cag              3312
Met Arg Glu Ala Val Thr Val Glu Ile Glu Phe Cys Val Trp Asp Gln
    1090                1095                1100 ttc ctg ggt gag atc aac cca cag cac agc tgg atg gtg gca ggg cct              3360
Phe Leu Gly Glu Ile Asn Pro Gln His Ser Trp Met Val Ala Gly Pro
1105                1110                1115                1120 ctg ctg gac atc aag gct gag cct gga gct gtg gaa gct gtg cac ctc              3408
Leu Leu Asp Ile Lys Ala Glu Pro Gly Ala Val Glu Ala Val His Leu
                1125                1130                1135 cct cac ttt gtg gct ctc caa ggg ggc cat gtg gac aca tcc ctg ttc              3456
Pro His Phe Val Ala Leu Gln Gly Gly His Val Asp Thr Ser Leu Phe
            1140                1145                1150 caa atg gcc cac ttt aaa gag gag ggg atg ctc ctg gag aag cca gcc              3504
Gln Met Ala His Phe Lys Glu Glu Gly Met Leu Leu Glu Lys Pro Ala
        1155                1160                1165 agg gtg gag ctg cat cac ata gtt ctg gaa aac ccc agc ttc tcc ccc              3552
Arg Val Glu Leu His His Ile Val Leu Glu Asn Pro Ser Phe Ser Pro
    1170                1175                1180 ttg gga gtc ctc ctg aaa atg atc cat aat gcc ctg cgc ttc att ccc              3600
Leu Gly Val Leu Leu Lys Met Ile His Asn Ala Leu Arg Phe Ile Pro
1185                1190                1195                1200 gtc acc tct gtg gtg ttg ctt tac cac cgc gtc cat cct gag gaa gtc              3648
Val Thr Ser Val Val Leu Leu Tyr His Arg Val His Pro Glu Glu Val
                1205                1210                1215 acc ttc cac ctc tac ctg atc cca agt gac tgc tcc att cgg aag gcc              3696
Thr Phe His Leu Tyr Leu Ile Pro Ser Asp Cys Ser Ile Arg Lys Ala
            1220                1225                1230 ata gat gat cta gaa atg aaa ttc cag ttt gtg cga atc cac aag cca              3744
Ile Asp Asp Leu Glu Met Lys Phe Gln Phe Val Arg Ile His Lys Pro
        1235                1240                1245
```

-continued

```
ccc ccg ctg acc cca ctt tat atg ggc tgt cgt tac act gtg tct ggg       3792
Pro Pro Leu Thr Pro Leu Tyr Met Gly Cys Arg Tyr Thr Val Ser Gly
    1250                1255                1260 tct ggt tca ggg atg ctg gaa ata ctc ccc aag gaa ctg gag ctc tgc       3840
Ser Gly Ser Gly Met Leu Glu Ile Leu Pro Lys Glu Leu Glu Leu Cys
1265                1270                1275                1280 tat cga agc cct gga gaa gac cag ctg ttc tcg gag ttc tac gtt ggc       3888
Tyr Arg Ser Pro Gly Glu Asp Gln Leu Phe Ser Glu Phe Tyr Val Gly
                1285                1290                1295 cac ttg gga tca ggg atc agg ctg caa gtg aaa gac aag aaa gat gag       3936
His Leu Gly Ser Gly Ile Arg Leu Gln Val Lys Asp Lys Lys Asp Glu
            1300                1305                1310 act ctg gtg tgg gag gcc ttg gtg aaa cca gga gat ctc atg cct gca       3984
Thr Leu Val Trp Glu Ala Leu Val Lys Pro Gly Asp Leu Met Pro Ala
        1315                1320                1325 act act ctg atc cct cca gcc cgc ata gcc gta cct tca cct ctg gat       4032
Thr Thr Leu Ile Pro Pro Ala Arg Ile Ala Val Pro Ser Pro Leu Asp
    1330                1335                1340 gcc ccg cag ttg ctg cac ttt gtg gac cag tat cga gag cag ctg ata       4080
Ala Pro Gln Leu Leu His Phe Val Asp Gln Tyr Arg Glu Gln Leu Ile
1345                1350                1355                1360 gcc cga gtg aca tcg gtg gag gtt gtc ttg gac aaa ctg cat gga cag       4128
Ala Arg Val Thr Ser Val Glu Val Val Leu Asp Lys Leu His Gly Gln
                1365                1370                1375 gtg ctg agc cag gag cag tac gag agg gtg ctg gct gag aac acg agg       4176
Val Leu Ser Gln Glu Gln Tyr Glu Arg Val Leu Ala Glu Asn Thr Arg
            1380                1385                1390 ccc agc cag atg cgg aag ctg ttc agc ttg agc cag tcc tgg gac cgg       4224
Pro Ser Gln Met Arg Lys Leu Phe Ser Leu Ser Gln Ser Trp Asp Arg
        1395                1400                1405 aag tgc aaa gat gga ctc tac caa gcc ctg aag gag acc cat cct cac       4272
Lys Cys Lys Asp Gly Leu Tyr Gln Ala Leu Lys Glu Thr His Pro His
    1410                1415                1420 ctc att atg gaa ctc tgg gag aag ggc agc aaa aag gga ctc ctg cca       4320
Leu Ile Met Glu Leu Trp Glu Lys Gly Ser Lys Lys Gly Leu Leu Pro
1425                1430                1435                1440 ctc agc agc tga                                                       4332
Leu Ser Ser
```

<210> SEQ ID NO 6
<211> LENGTH: 1443
<212> TYPE: PRT
<213> ORGANISM: Homo sapiens

<400> SEQUENCE: 6

```
Met Ala Gly Gly Ala Trp Gly Arg Leu Ala Cys Tyr Leu Glu Phe Leu
  1               5                  10                  15

Lys Lys Glu Glu Leu Lys Glu Phe Gln Leu Leu Leu Ala Asn Lys Ala
             20                  25                  30

His Ser Arg Ser Ser Ser Gly Glu Thr Pro Ala Gln Pro Glu Lys Thr
         35                  40                  45

Ser Gly Met Glu Val Ala Ser Tyr Leu Val Ala Gln Tyr Gly Glu Gln
     50                  55                  60

Arg Ala Trp Asp Leu Ala Leu His Thr Trp Glu Gln Met Gly Leu Arg
 65                  70                  75                  80

Ser Leu Cys Ala Gln Ala Gln Glu Gly Ala Gly His Ser Pro Ser Phe
                 85                  90                  95

Pro Tyr Ser Pro Ser Glu Pro His Leu Gly Ser Pro Ser Gln Pro Thr
            100                 105                 110
```

```
Ser Thr Ala Val Leu Met Pro Trp Ile His Glu Leu Pro Ala Gly Cys
        115                 120                 125

Thr Gln Gly Ser Glu Arg Arg Val Leu Arg Gln Leu Pro Asp Thr Ser
130                 135                 140

Gly Arg Arg Trp Arg Glu Ile Ser Ala Ser Leu Leu Tyr Gln Ala Leu
145                 150                 155                 160

Pro Ser Ser Pro Asp His Glu Ser Pro Gln Glu Ser Pro Asn Ala
                165                 170                 175

Pro Thr Ser Thr Ala Val Leu Gly Ser Trp Gly Ser Pro Gln Pro
                180                 185                 190

Ser Leu Ala Pro Arg Glu Gln Glu Ala Pro Gly Thr Gln Trp Pro Leu
        195                 200                 205

Asp Glu Thr Ser Gly Ile Tyr Tyr Thr Glu Ile Arg Glu Arg Glu Arg
        210                 215                 220

Glu Lys Ser Glu Lys Gly Arg Pro Pro Trp Ala Ala Val Gly Thr
225                 230                 235                 240

Pro Pro Gln Ala His Thr Ser Leu Gln Pro His His Pro Trp Glu
                245                 250                 255

Pro Ser Val Arg Glu Ser Leu Cys Ser Thr Trp Pro Trp Lys Asn Glu
                260                 265                 270

Asp Phe Asn Gln Lys Phe Thr Gln Leu Leu Leu Gln Arg Pro His
                275                 280                 285

Pro Arg Ser Gln Asp Pro Leu Val Lys Arg Ser Trp Pro Asp Tyr Val
        290                 295                 300

Glu Glu Asn Arg Gly His Leu Ile Glu Ile Arg Asp Leu Phe Gly Pro
305                 310                 315                 320

Gly Leu Asp Thr Gln Glu Pro Arg Ile Val Ile Leu Gln Gly Ala Ala
                325                 330                 335

Gly Ile Gly Lys Ser Thr Leu Ala Arg Gln Val Lys Glu Ala Trp Gly
                340                 345                 350

Arg Gly Gln Leu Tyr Gly Asp Arg Phe Gln His Val Phe Tyr Phe Ser
        355                 360                 365

Cys Arg Glu Leu Ala Gln Ser Lys Val Val Ser Leu Ala Glu Leu Ile
        370                 375                 380

Gly Lys Asp Gly Thr Ala Thr Pro Ala Pro Ile Arg Gln Ile Leu Ser
385                 390                 395                 400

Arg Pro Glu Arg Leu Leu Phe Ile Leu Asp Gly Val Asp Glu Pro Gly
                405                 410                 415

Trp Val Leu Gln Glu Pro Ser Ser Glu Leu Cys Leu His Trp Ser Gln
                420                 425                 430

Pro Gln Pro Ala Asp Ala Leu Leu Gly Ser Leu Leu Gly Lys Thr Ile
        435                 440                 445

Leu Pro Glu Ala Ser Phe Leu Ile Thr Ala Arg Thr Thr Ala Leu Gln
        450                 455                 460

Asn Leu Ile Pro Ser Leu Glu Gln Ala Arg Trp Val Glu Val Leu Gly
465                 470                 475                 480

Phe Ser Glu Ser Ser Arg Lys Glu Tyr Phe Tyr Arg Tyr Phe Thr Asp
                485                 490                 495

Glu Arg Gln Ala Ile Arg Ala Phe Arg Leu Val Lys Ser Asn Lys Glu
                500                 505                 510

Leu Trp Ala Leu Cys Leu Val Pro Trp Val Ser Trp Leu Ala Cys Thr
        515                 520                 525
```

```
Cys Leu Met Gln Gln Met Lys Arg Lys Glu Lys Leu Thr Leu Thr Ser
    530                 535                 540

Lys Thr Thr Thr Thr Leu Cys Leu His Tyr Leu Ala Gln Ala Leu Gln
545                 550                 555                 560

Ala Gln Pro Leu Gly Pro Gln Leu Arg Asp Leu Cys Ser Leu Ala Ala
                565                 570                 575

Glu Gly Ile Trp Gln Lys Lys Thr Leu Phe Ser Pro Asp Asp Leu Arg
                580                 585                 590

Lys His Gly Leu Asp Gly Ala Ile Ile Ser Thr Phe Leu Lys Met Gly
                595                 600                 605

Ile Leu Gln Glu His Pro Ile Pro Leu Ser Tyr Ser Phe Ile His Leu
    610                 615                 620

Cys Phe Gln Glu Phe Phe Ala Ala Met Ser Tyr Val Leu Glu Asp Glu
625                 630                 635                 640

Lys Gly Arg Gly Lys His Ser Asn Cys Ile Ile Asp Leu Glu Lys Thr
                645                 650                 655

Leu Glu Ala Tyr Gly Ile His Gly Leu Phe Gly Ala Ser Thr Thr Arg
                660                 665                 670

Phe Leu Leu Gly Leu Leu Ser Asp Glu Gly Glu Arg Glu Met Glu Asn
    675                 680                 685

Ile Phe His Cys Arg Leu Ser Gln Gly Arg Asn Leu Met Gln Trp Val
    690                 695                 700

Pro Ser Leu Gln Leu Leu Leu Gln Pro His Ser Leu Glu Ser Leu His
705                 710                 715                 720

Cys Leu Tyr Glu Thr Arg Asn Lys Thr Phe Leu Thr Gln Val Met Ala
                725                 730                 735

His Phe Glu Glu Met Gly Met Cys Val Glu Thr Asp Met Glu Leu Leu
                740                 745                 750

Val Cys Thr Phe Cys Ile Lys Phe Ser Arg His Val Lys Lys Leu Gln
                755                 760                 765

Leu Ile Glu Gly Arg Gln His Arg Ser Thr Trp Ser Pro Thr Met Val
    770                 775                 780

Val Leu Phe Arg Trp Val Pro Val Thr Asp Ala Tyr Trp Gln Ile Leu
785                 790                 795                 800

Phe Ser Val Leu Lys Val Thr Arg Asn Leu Lys Glu Leu Asp Leu Ser
                805                 810                 815

Gly Asn Ser Leu Ser His Ser Ala Val Lys Ser Leu Cys Lys Thr Leu
                820                 825                 830

Arg Arg Pro Arg Cys Leu Leu Glu Thr Leu Arg Leu Ala Gly Cys Gly
                835                 840                 845

Leu Thr Ala Glu Asp Cys Lys Asp Leu Ala Phe Gly Leu Arg Ala Asn
    850                 855                 860

Gln Thr Leu Thr Glu Leu Asp Leu Ser Phe Asn Val Leu Thr Asp Ala
865                 870                 875                 880

Gly Ala Lys His Leu Cys Gln Arg Leu Arg Gln Pro Ser Cys Lys Leu
                885                 890                 895

Gln Arg Leu Gln Leu Val Ser Cys Gly Leu Thr Ser Asp Cys Cys Gln
                900                 905                 910

Asp Leu Ala Ser Val Leu Ser Ala Ser Pro Ser Leu Lys Glu Leu Asp
                915                 920                 925

Leu Gln Gln Asn Asn Leu Asp Asp Val Gly Val Arg Leu Leu Cys Glu
    930                 935                 940

Gly Leu Arg His Pro Ala Cys Lys Leu Ile Arg Leu Gly Lys Pro Ser
```

-continued

```
              945                 950                 955                 960
Val Met Thr Pro Thr Glu Gly Leu Asp Thr Gly Glu Met Ser Asn Ser
                    965                 970                 975
Thr Ser Ser Leu Lys Arg Gln Arg Leu Gly Ser Glu Arg Ala Ala Ser
                    980                 985                 990
His Val Ala Gln Ala Asn Leu Lys Leu Leu Asp Val Ser Lys Ile Phe
                    995                1000                1005
Pro Ile Ala Glu Ile Ala Glu Glu Ser Ser Pro Glu Val Val Pro Val
                   1010                1015                1020
Glu Leu Leu Cys Val Pro Ser Pro Ala Ser Gln Gly Asp Leu His Thr
1025                1030                1035                1040
Lys Pro Leu Gly Thr Asp Asp Asp Phe Trp Gly Pro Thr Gly Pro Val
                   1045                1050                1055
Ala Thr Glu Val Val Asp Lys Glu Lys Asn Leu Tyr Arg Val His Phe
                   1060                1065                1070
Pro Val Ala Gly Ser Tyr Arg Trp Pro Asn Thr Gly Leu Cys Phe Val
                   1075                1080                1085
Met Arg Glu Ala Val Thr Val Glu Ile Glu Phe Cys Val Trp Asp Gln
                   1090                1095                1100
Phe Leu Gly Glu Ile Asn Pro Gln His Ser Trp Met Val Ala Gly Pro
1105                1110                1115                1120
Leu Leu Asp Ile Lys Ala Glu Pro Gly Ala Val Glu Ala Val His Leu
                   1125                1130                1135
Pro His Phe Val Ala Leu Gln Gly Gly His Val Asp Thr Ser Leu Phe
                   1140                1145                1150
Gln Met Ala His Phe Lys Glu Glu Gly Met Leu Leu Glu Lys Pro Ala
                   1155                1160                1165
Arg Val Glu Leu His His Ile Val Leu Glu Asn Pro Ser Phe Ser Pro
                   1170                1175                1180
Leu Gly Val Leu Leu Lys Met Ile His Asn Ala Leu Arg Phe Ile Pro
1185                1190                1195                1200
Val Thr Ser Val Val Leu Leu Tyr His Arg Val His Pro Glu Glu Val
                   1205                1210                1215
Thr Phe His Leu Tyr Leu Ile Pro Ser Asp Cys Ser Ile Arg Lys Ala
                   1220                1225                1230
Ile Asp Asp Leu Glu Met Lys Phe Gln Phe Val Arg Ile His Lys Pro
                   1235                1240                1245
Pro Pro Leu Thr Pro Leu Tyr Met Gly Cys Arg Tyr Thr Val Ser Gly
                   1250                1255                1260
Ser Gly Ser Gly Met Leu Glu Ile Leu Pro Lys Glu Leu Glu Leu Cys
1265                1270                1275                1280
Tyr Arg Ser Pro Gly Glu Asp Gln Leu Phe Ser Glu Phe Tyr Val Gly
                   1285                1290                1295
His Leu Gly Ser Gly Ile Arg Leu Gln Val Lys Asp Lys Lys Asp Glu
                   1300                1305                1310
Thr Leu Val Trp Glu Ala Leu Val Lys Pro Gly Asp Leu Met Pro Ala
                   1315                1320                1325
Thr Thr Leu Ile Pro Pro Ala Arg Ile Ala Val Pro Ser Pro Leu Asp
                   1330                1335                1340
Ala Pro Gln Leu Leu His Phe Val Asp Gln Tyr Arg Glu Gln Leu Ile
1345                1350                1355                1360
Ala Arg Val Thr Ser Val Glu Val Val Leu Asp Lys Leu His Gly Gln
                   1365                1370                1375
```

```
Val Leu Ser Gln Glu Gln Tyr Glu Arg Val Leu Ala Glu Asn Thr Arg
            1380                1385                1390

Pro Ser Gln Met Arg Lys Leu Phe Ser Leu Ser Gln Ser Trp Asp Arg
        1395                1400                1405

Lys Cys Lys Asp Gly Leu Tyr Gln Ala Leu Lys Glu Thr His Pro His
    1410                1415                1420

Leu Ile Met Glu Leu Trp Glu Lys Gly Ser Lys Lys Gly Leu Leu Pro
1425                1430                1435                1440

Leu Ser Ser

<210> SEQ ID NO 7
<211> LENGTH: 1487
<212> TYPE: DNA
<213> ORGANISM: Homo sapiens
<220> FEATURE:
<221> NAME/KEY: CDS
<222> LOCATION: (1)..(1296)

<400> SEQUENCE: 7
```

| | | | | | | | | | | | | | | | | |
|---|---|---|---|---|---|---|---|---|---|---|---|---|---|---|---|---|
| atg atg aga cag agg cag agc cat tat tgt tcc gtg ctg ttc ctg agt | | | | | | | | | | | | | | | | 48 |
| Met Met Arg Gln Arg Gln Ser His Tyr Cys Ser Val Leu Phe Leu Ser | | | | | | | | | | | | | | | | |
| 1 | | | | 5 | | | | | 10 | | | | | 15 | | |
| gtc aac tat ctg ggg ggg aca ttc cca gga gac att tgc tca gaa gag | | | | | | | | | | | | | | | | 96 |
| Val Asn Tyr Leu Gly Gly Thr Phe Pro Gly Asp Ile Cys Ser Glu Glu | | | | | | | | | | | | | | | | |
| | | | | 20 | | | | | 25 | | | | | 30 | | |
| aat caa ata gtt tcc tct tat gct tct aaa gtc tgt ttt gag atc gaa | | | | | | | | | | | | | | | | 144 |
| Asn Gln Ile Val Ser Ser Tyr Ala Ser Lys Val Cys Phe Glu Ile Glu | | | | | | | | | | | | | | | | |
| | | | 35 | | | | | 40 | | | | | 45 | | | |
| gaa gat tat aaa aat cgt cag ttt ctg ggg cct gaa gga aat gtg gat | | | | | | | | | | | | | | | | 192 |
| Glu Asp Tyr Lys Asn Arg Gln Phe Leu Gly Pro Glu Gly Asn Val Asp | | | | | | | | | | | | | | | | |
| | | 50 | | | | | 55 | | | | | 60 | | | | |
| gtt gag ttg att gat aag agc aca aac aga tac agc gtt tgg ttc ccc | | | | | | | | | | | | | | | | 240 |
| Val Glu Leu Ile Asp Lys Ser Thr Asn Arg Tyr Ser Val Trp Phe Pro | | | | | | | | | | | | | | | | |
| 65 | | | | | 70 | | | | | 75 | | | | | 80 | |
| act gct ggc tgg tat ctg tgg tca gcc aca ggc ctc ggc ttc ctg gta | | | | | | | | | | | | | | | | 288 |
| Thr Ala Gly Trp Tyr Leu Trp Ser Ala Thr Gly Leu Gly Phe Leu Val | | | | | | | | | | | | | | | | |
| | | | | 85 | | | | | 90 | | | | | 95 | | |
| agg gat gag gtc aca gtg acg att gcg ttt ggt tcc tgg agt cag cac | | | | | | | | | | | | | | | | 336 |
| Arg Asp Glu Val Thr Val Thr Ile Ala Phe Gly Ser Trp Ser Gln His | | | | | | | | | | | | | | | | |
| | | | | 100 | | | | | 105 | | | | | 110 | | |
| ctg gcc ctg gac ctg cag cac cat gaa cag tgg ctg gtg ggc ggc ccc | | | | | | | | | | | | | | | | 384 |
| Leu Ala Leu Asp Leu Gln His His Glu Gln Trp Leu Val Gly Gly Pro | | | | | | | | | | | | | | | | |
| | | | 115 | | | | | 120 | | | | | 125 | | | |
| ttg ttt gat gtc act gca gag cca gag gag gct gtc gcc gaa atc cac | | | | | | | | | | | | | | | | 432 |
| Leu Phe Asp Val Thr Ala Glu Pro Glu Glu Ala Val Ala Glu Ile His | | | | | | | | | | | | | | | | |
| | | 130 | | | | | 135 | | | | | 140 | | | | |
| ctc ccc cac ttc atc tcc ctc caa ggt gag gtg gac gtc tcc tgg ttt | | | | | | | | | | | | | | | | 480 |
| Leu Pro His Phe Ile Ser Leu Gln Gly Glu Val Asp Val Ser Trp Phe | | | | | | | | | | | | | | | | |
| 145 | | | | | 150 | | | | | 155 | | | | | 160 | |
| ctc gtt gcc cat ttt aag aat gaa ggg atg gtc ctg gag cat cca gcc | | | | | | | | | | | | | | | | 528 |
| Leu Val Ala His Phe Lys Asn Glu Gly Met Val Leu Glu His Pro Ala | | | | | | | | | | | | | | | | |
| | | | | 165 | | | | | 170 | | | | | 175 | | |
| cgg gtg gag cct ttc tat gct gtc ctg gaa agc ccc agc ttc tct ctg | | | | | | | | | | | | | | | | 576 |
| Arg Val Glu Pro Phe Tyr Ala Val Leu Glu Ser Pro Ser Phe Ser Leu | | | | | | | | | | | | | | | | |
| | | | | 180 | | | | | 185 | | | | | 190 | | |
| atg ggc atc ctg ctg cgg atc gcc agt ggg act cgc ctc tcc atc ccc | | | | | | | | | | | | | | | | 624 |
| Met Gly Ile Leu Leu Arg Ile Ala Ser Gly Thr Arg Leu Ser Ile Pro | | | | | | | | | | | | | | | | |
| | | | 195 | | | | | 200 | | | | | 205 | | | |
| atc act tcc aac aca ttg atc tat tat cac ccc cac ccc gaa gat att | | | | | | | | | | | | | | | | 672 |

```
                Ile Thr Ser Asn Thr Leu Ile Tyr Tyr His Pro His Pro Glu Asp Ile
                    210                 215                 220 aag ttc cac ttg tac ctt gtc ccc agc gac gcc ttg cta aca aag gcg          720
Lys Phe His Leu Tyr Leu Val Pro Ser Asp Ala Leu Leu Thr Lys Ala
225                 230                 235                 240 ata gat gat gag gaa gat cgc ttc cat ggt gtg cgc ctg cag act tcg          768
Ile Asp Asp Glu Glu Asp Arg Phe His Gly Val Arg Leu Gln Thr Ser
                245                 250                 255 ccc cca atg gaa ccc ctg aac ttt ggt tcc agt tat att gtg tct aat          816
Pro Pro Met Glu Pro Leu Asn Phe Gly Ser Ser Tyr Ile Val Ser Asn
            260                 265                 270 tct gct aac ctg aaa gta atg ccc aag gag ttg aaa ttg tcc tac agg          864
Ser Ala Asn Leu Lys Val Met Pro Lys Glu Leu Lys Leu Ser Tyr Arg
        275                 280                 285 agc cct gga gaa att cag cac ttc tca aaa ttc tat gct ggg cag atg          912
Ser Pro Gly Glu Ile Gln His Phe Ser Lys Phe Tyr Ala Gly Gln Met
    290                 295                 300 aag gaa ccc att caa ctt gag att act gaa aaa aga cat ggg act ttg          960
Lys Glu Pro Ile Gln Leu Glu Ile Thr Glu Lys Arg His Gly Thr Leu
305                 310                 315                 320 gtg tgg gat act gag gtg aag cca gtg gat ctc cag ctt gta gct gca         1008
Val Trp Asp Thr Glu Val Lys Pro Val Asp Leu Gln Leu Val Ala Ala
                325                 330                 335 tca gcc cct cct cct ttc tca ggt gca gcc ttt gtg aag gag aac cac         1056
Ser Ala Pro Pro Pro Phe Ser Gly Ala Ala Phe Val Lys Glu Asn His
            340                 345                 350 cgg caa ctc caa gcc agg atg ggg gac ctg aaa ggg gtg ctc gat gat         1104
Arg Gln Leu Gln Ala Arg Met Gly Asp Leu Lys Gly Val Leu Asp Asp
        355                 360                 365 ctc cag gac aat gag gtt ctt act gag aat gag aag gag ctg gtg gag         1152
Leu Gln Asp Asn Glu Val Leu Thr Glu Asn Glu Lys Glu Leu Val Glu
    370                 375                 380 cag gaa aag aca cgg cag agc aag aat gag gcc ttg ctg agc atg gtg         1200
Gln Glu Lys Thr Arg Gln Ser Lys Asn Glu Ala Leu Leu Ser Met Val
385                 390                 395                 400 gag aag aaa ggg gac ctg gcc ctg gac gtg ctc ttc aga agc att agt         1248
Glu Lys Lys Gly Asp Leu Ala Leu Asp Val Leu Phe Arg Ser Ile Ser
                405                 410                 415 gaa agg gac cct tac ctc gtg tcc tat ctt aga cag cag aat ttg taa         1296
Glu Arg Asp Pro Tyr Leu Val Ser Tyr Leu Arg Gln Gln Asn Leu
            420                 425                 430 aatgagtcag ttaggtagtc tggaagagag aatccagcgt tctcattgga aatggataaa      1356
cagaaatgtg atcattgatt tcagtgttca agacagaaga agactgggta acatctatca      1416
cacaggcttt caggacagac ttgtaacctg gcatgtacct attgactgta tcctcatgca      1476
ttttcctcaa g                                                            1487

<210> SEQ ID NO 8
<211> LENGTH: 431
<212> TYPE: PRT
<213> ORGANISM: Homo sapiens

<400> SEQUENCE: 8

Met Met Arg Gln Arg Gln Ser His Tyr Cys Ser Val Leu Phe Leu Ser
1               5                   10                  15

Val Asn Tyr Leu Gly Gly Thr Phe Pro Gly Asp Ile Cys Ser Glu Glu
            20                  25                  30

Asn Gln Ile Val Ser Ser Tyr Ala Ser Lys Val Cys Phe Glu Ile Glu
        35                  40                  45
```

```
Glu Asp Tyr Lys Asn Arg Gln Phe Leu Gly Pro Glu Gly Asn Val Asp
 50                  55                  60

Val Glu Leu Ile Asp Lys Ser Thr Asn Arg Tyr Ser Val Trp Phe Pro
 65                  70                  75                  80

Thr Ala Gly Trp Tyr Leu Trp Ser Ala Thr Gly Leu Gly Phe Leu Val
                 85                  90                  95

Arg Asp Glu Val Thr Val Thr Ile Ala Phe Gly Ser Trp Ser Gln His
            100                 105                 110

Leu Ala Leu Asp Leu Gln His His Glu Gln Trp Leu Val Gly Gly Pro
        115                 120                 125

Leu Phe Asp Val Thr Ala Glu Pro Glu Glu Ala Val Ala Glu Ile His
    130                 135                 140

Leu Pro His Phe Ile Ser Leu Gln Gly Glu Val Asp Val Ser Trp Phe
145                 150                 155                 160

Leu Val Ala His Phe Lys Asn Glu Gly Met Val Leu Glu His Pro Ala
                165                 170                 175

Arg Val Glu Pro Phe Tyr Ala Val Leu Glu Ser Pro Ser Phe Ser Leu
            180                 185                 190

Met Gly Ile Leu Leu Arg Ile Ala Ser Gly Thr Arg Leu Ser Ile Pro
        195                 200                 205

Ile Thr Ser Asn Thr Leu Ile Tyr Tyr His Pro His Pro Glu Asp Ile
    210                 215                 220

Lys Phe His Leu Tyr Leu Val Pro Ser Asp Ala Leu Leu Thr Lys Ala
225                 230                 235                 240

Ile Asp Asp Glu Glu Asp Arg Phe His Gly Val Arg Leu Gln Thr Ser
                245                 250                 255

Pro Pro Met Glu Pro Leu Asn Phe Gly Ser Ser Tyr Ile Val Ser Asn
            260                 265                 270

Ser Ala Asn Leu Lys Val Met Pro Lys Glu Leu Lys Leu Ser Tyr Arg
        275                 280                 285

Ser Pro Gly Glu Ile Gln His Phe Ser Lys Phe Tyr Ala Gly Gln Met
    290                 295                 300

Lys Glu Pro Ile Gln Leu Glu Ile Thr Glu Lys Arg His Gly Thr Leu
305                 310                 315                 320

Val Trp Asp Thr Glu Val Lys Pro Val Asp Leu Gln Leu Val Ala Ala
                325                 330                 335

Ser Ala Pro Pro Phe Ser Gly Ala Ala Phe Val Lys Glu Asn His
            340                 345                 350

Arg Gln Leu Gln Ala Arg Met Gly Asp Leu Lys Gly Val Leu Asp Asp
        355                 360                 365

Leu Gln Asp Asn Glu Val Leu Thr Glu Asn Glu Lys Glu Leu Val Glu
    370                 375                 380

Gln Glu Lys Thr Arg Gln Ser Lys Asn Glu Ala Leu Leu Ser Met Val
385                 390                 395                 400

Glu Lys Lys Gly Asp Leu Ala Leu Asp Val Leu Phe Arg Ser Ile Ser
                405                 410                 415

Glu Arg Asp Pro Tyr Leu Val Ser Tyr Leu Arg Gln Gln Asn Leu
            420                 425                 430

<210> SEQ ID NO 9
<211> LENGTH: 4556
<212> TYPE: DNA
<213> ORGANISM: Artificial Sequence
<220> FEATURE:
```

<221> NAME/KEY: CDS
<222> LOCATION: (1)..(4365)
<220> FEATURE:
<223> OTHER INFORMATION: Description of Artificial Sequence: Synthetic Construct

<400> SEQUENCE: 9

| | | | | | | | | | | | | | | | | |
|---|---|---|---|---|---|---|---|---|---|---|---|---|---|---|---|---|
| atg | gct | ggc | gga | gcc | tgg | ggc | cgc | ctg | gcc | tgt | tac | ttg | gag | ttc | ctg | 48 |
| Met | Ala | Gly | Gly | Ala | Trp | Gly | Arg | Leu | Ala | Cys | Tyr | Leu | Glu | Phe | Leu | |
| 1 | | | | 5 | | | | | 10 | | | | | 15 | | |
| aag | aag | gag | gag | ctg | aag | gag | ttc | cag | ctt | ctg | ctc | gcc | aat | aaa | gcg | 96 |
| Lys | Lys | Glu | Glu | Leu | Lys | Glu | Phe | Gln | Leu | Leu | Leu | Ala | Asn | Lys | Ala | |
| | | | 20 | | | | | 25 | | | | | 30 | | | |
| cac | tcc | agg | agc | tct | tcg | ggt | gag | aca | ccc | gct | cag | cca | gag | aag | acg | 144 |
| His | Ser | Arg | Ser | Ser | Ser | Gly | Glu | Thr | Pro | Ala | Gln | Pro | Glu | Lys | Thr | |
| | | 35 | | | | | 40 | | | | | 45 | | | | |
| agt | ggc | atg | gag | gtg | gcc | tcg | tac | ctg | gtg | gct | cag | tat | ggg | gag | cag | 192 |
| Ser | Gly | Met | Glu | Val | Ala | Ser | Tyr | Leu | Val | Ala | Gln | Tyr | Gly | Glu | Gln | |
| | 50 | | | | | 55 | | | | | 60 | | | | | |
| cgg | gcc | tgg | gac | cta | gcc | ctc | cat | acc | tgg | gag | cag | atg | ggg | ctg | agg | 240 |
| Arg | Ala | Trp | Asp | Leu | Ala | Leu | His | Thr | Trp | Glu | Gln | Met | Gly | Leu | Arg | |
| 65 | | | | | 70 | | | | | 75 | | | | | 80 | |
| tca | ctg | tgc | gcc | caa | gcc | cag | gaa | ggg | gca | ggc | cac | tct | ccc | tca | ttc | 288 |
| Ser | Leu | Cys | Ala | Gln | Ala | Gln | Glu | Gly | Ala | Gly | His | Ser | Pro | Ser | Phe | |
| | | | | 85 | | | | | 90 | | | | | 95 | | |
| ccc | tac | agc | cca | agt | gaa | ccc | cac | ctg | ggg | tct | ccc | agc | caa | ccc | acc | 336 |
| Pro | Tyr | Ser | Pro | Ser | Glu | Pro | His | Leu | Gly | Ser | Pro | Ser | Gln | Pro | Thr | |
| | | | 100 | | | | | 105 | | | | | 110 | | | |
| tcc | acc | gca | gtg | cta | atg | ccc | tgg | atc | cat | gaa | ttg | ccg | gcg | ggg | tgc | 384 |
| Ser | Thr | Ala | Val | Leu | Met | Pro | Trp | Ile | His | Glu | Leu | Pro | Ala | Gly | Cys | |
| | | | 115 | | | | | 120 | | | | | 125 | | | |
| acc | cag | ggc | tca | gag | aga | agg | gtt | ttg | aga | cag | ctg | cct | gac | aca | tct | 432 |
| Thr | Gln | Gly | Ser | Glu | Arg | Arg | Val | Leu | Arg | Gln | Leu | Pro | Asp | Thr | Ser | |
| | | 130 | | | | | 135 | | | | | 140 | | | | |
| gga | cgc | cgc | tgg | aga | gaa | atc | tct | gcc | tca | ctc | ctc | tac | caa | gct | ctt | 480 |
| Gly | Arg | Arg | Trp | Arg | Glu | Ile | Ser | Ala | Ser | Leu | Leu | Tyr | Gln | Ala | Leu | |
| 145 | | | | | 150 | | | | | 155 | | | | | 160 | |
| cca | agc | tcc | cca | gac | cat | gag | tct | cca | agc | cag | gag | tca | ccc | aac | gcc | 528 |
| Pro | Ser | Ser | Pro | Asp | His | Glu | Ser | Pro | Ser | Gln | Glu | Ser | Pro | Asn | Ala | |
| | | | | 165 | | | | | 170 | | | | | 175 | | |
| ccc | aca | tcc | aca | gca | gtg | ctg | ggg | agc | tgg | gga | tcc | cca | cct | cag | ccc | 576 |
| Pro | Thr | Ser | Thr | Ala | Val | Leu | Gly | Ser | Trp | Gly | Ser | Pro | Pro | Gln | Pro | |
| | | | 180 | | | | | 185 | | | | | 190 | | | |
| agc | cta | gca | ccc | aga | gag | cag | gag | gct | cct | ggg | acc | caa | tgg | cct | ctg | 624 |
| Ser | Leu | Ala | Pro | Arg | Glu | Gln | Glu | Ala | Pro | Gly | Thr | Gln | Trp | Pro | Leu | |
| | | 195 | | | | | 200 | | | | | 205 | | | | |
| gat | gaa | acg | tca | gga | att | tac | tac | aca | gaa | atc | aga | gaa | aga | gag | aga | 672 |
| Asp | Glu | Thr | Ser | Gly | Ile | Tyr | Tyr | Thr | Glu | Ile | Arg | Glu | Arg | Glu | Arg | |
| 210 | | | | | 215 | | | | | 220 | | | | | | |
| gag | aaa | tca | gag | aaa | ggc | agg | ccc | cca | tgg | gca | gcg | gtg | gta | gga | acg | 720 |
| Glu | Lys | Ser | Glu | Lys | Gly | Arg | Pro | Pro | Trp | Ala | Ala | Val | Val | Gly | Thr | |
| 225 | | | | | 230 | | | | | 235 | | | | | 240 | |
| ccc | cca | cag | gcg | cac | acc | agc | cta | cag | ccc | cac | cac | cac | cca | tgg | gag | 768 |
| Pro | Pro | Gln | Ala | His | Thr | Ser | Leu | Gln | Pro | His | His | His | Pro | Trp | Glu | |
| | | | | 245 | | | | | 250 | | | | | 255 | | |
| cct | tct | gtg | aga | gag | agc | ctc | tgt | tcc | aca | tgg | ccc | tgg | aaa | aat | gag | 816 |
| Pro | Ser | Val | Arg | Glu | Ser | Leu | Cys | Ser | Thr | Trp | Pro | Trp | Lys | Asn | Glu | |
| | | | 260 | | | | | 265 | | | | | 270 | | | |
| gat | ttt | aac | caa | aaa | ttc | aca | cag | ctg | cta | ctt | cta | caa | aga | cct | cac | 864 |
| Asp | Phe | Asn | Gln | Lys | Phe | Thr | Gln | Leu | Leu | Leu | Leu | Gln | Arg | Pro | His | |
| | | 275 | | | | | 280 | | | | | 285 | | | | |

-continued

| | |
|---|---|
| ccc aga agc caa gat ccc ctg gtc aag aga agc tgg cct gat tat gtg<br>Pro Arg Ser Gln Asp Pro Leu Val Lys Arg Ser Trp Pro Asp Tyr Val<br>290                              295                             300 | 912 |
| gag gag aat cga gga cat tta att gag atc aga gac tta ttt ggc cca<br>Glu Glu Asn Arg Gly His Leu Ile Glu Ile Arg Asp Leu Phe Gly Pro<br>305                              310                             315                       320 | 960 |
| ggc ctg gat acc caa gaa cct cgc ata gtc ata ctg cag ggg gct gct<br>Gly Leu Asp Thr Gln Glu Pro Arg Ile Val Ile Leu Gln Gly Ala Ala<br>                       325                             330                             335 | 1008 |
| gga att ggg aag tca aca ctg gcc agg cag gtg aag gaa gcc tgg ggg<br>Gly Ile Gly Lys Ser Thr Leu Ala Arg Gln Val Lys Glu Ala Trp Gly<br>              340                            345                             350 | 1056 |
| aga ggc cag ctg tat ggg gac cgc ttc cag cat gtc ttc tac ttc agc<br>Arg Gly Gln Leu Tyr Gly Asp Arg Phe Gln His Val Phe Tyr Phe Ser<br>                       355                             360                             365 | 1104 |
| tgc aga gag ctg gcc cag tcc aag gtg gtg agt ctc gct gag ctc atc<br>Cys Arg Glu Leu Ala Gln Ser Lys Val Val Ser Leu Ala Glu Leu Ile<br>     370                             375                             380 | 1152 |
| gga aaa gat ggg aca gcc act ccg gct ccc att aga cag atc ctg tct<br>Gly Lys Asp Gly Thr Ala Thr Pro Ala Pro Ile Arg Gln Ile Leu Ser<br>385                              390                             395                       400 | 1200 |
| agg cca gag cgg ctg ctc ttc atc ctc gat ggt gta gat gag cca gga<br>Arg Pro Glu Arg Leu Leu Phe Ile Leu Asp Gly Val Asp Glu Pro Gly<br>                       405                             410                             415 | 1248 |
| tgg gtc ttg cag gag ccg agt tct gag ctc tgt ctg cac tgg agc cag<br>Trp Val Leu Gln Glu Pro Ser Ser Glu Leu Cys Leu His Trp Ser Gln<br>              420                            425                             430 | 1296 |
| cca cag ccg gcg gat gca ctg ctg ggc agt ttg ctg ggg aaa act ata<br>Pro Gln Pro Ala Asp Ala Leu Leu Gly Ser Leu Leu Gly Lys Thr Ile<br>                       435                             440                             445 | 1344 |
| ctt ccc gag gca tcc ttc ctg atc acg gct cgg acc aca gct ctg cag<br>Leu Pro Glu Ala Ser Phe Leu Ile Thr Ala Arg Thr Thr Ala Leu Gln<br>     450                             455                             460 | 1392 |
| aac ctc att cct tct ttg gag cag gca cgt tgg gta gag gtc ctg ggg<br>Asn Leu Ile Pro Ser Leu Glu Gln Ala Arg Trp Val Glu Val Leu Gly<br>465                              470                             475                       480 | 1440 |
| ttc tct gag tcc agc agg aag gaa tat ttc tac aga tat ttc aca gat<br>Phe Ser Glu Ser Ser Arg Lys Glu Tyr Phe Tyr Arg Tyr Phe Thr Asp<br>                       485                             490                             495 | 1488 |
| gaa agg caa gca att aga gcc ttt agg ttg gtc aaa tca aac aaa gag<br>Glu Arg Gln Ala Ile Arg Ala Phe Arg Leu Val Lys Ser Asn Lys Glu<br>                    500                            505                           510 | 1536 |
| ctc tgg gcc ctg tgt ctt gtg ccc tgg gtg tcc tgg ctg gcc tgc act<br>Leu Trp Ala Leu Cys Leu Val Pro Trp Val Ser Trp Leu Ala Cys Thr<br>         515                             520                             525 | 1584 |
| tgc ctg atg cag cag atg aag cgg aag gaa aaa ctc aca ctg act tcc<br>Cys Leu Met Gln Gln Met Lys Arg Lys Glu Lys Leu Thr Leu Thr Ser<br>530                              535                             540 | 1632 |
| aag acc acc aca acc ctc tgt cta cat tac ctt gcc cag gct ctc caa<br>Lys Thr Thr Thr Thr Leu Cys Leu His Tyr Leu Ala Gln Ala Leu Gln<br>545                              550                             555                       560 | 1680 |
| gct cag cca ttg gga ccc cag ctc aga gac ctc tgc tct ctg gct gct<br>Ala Gln Pro Leu Gly Pro Gln Leu Arg Asp Leu Cys Ser Leu Ala Ala<br>                    565                            570                           575 | 1728 |
| gag ggc atc tgg caa aaa aag acc ctt ttc agt cca gat gac ctc agg<br>Glu Gly Ile Trp Gln Lys Lys Thr Leu Phe Ser Pro Asp Asp Leu Arg<br>                       580                             585                             590 | 1776 |
| aag cat ggg tta gat ggg gcc atc atc tcc acc ttc ttg aag atg ggt<br>Lys His Gly Leu Asp Gly Ala Ile Ile Ser Thr Phe Leu Lys Met Gly | 1824 |

```
                  595                  600                   605
att ctt caa gag cac ccc atc cct ctg agc tac agc ttc att cac ctc        1872
Ile Leu Gln Glu His Pro Ile Pro Leu Ser Tyr Ser Phe Ile His Leu
        610                  615                   620 tgt ttc caa gag ttc ttt gca gca atg tcc tat gtc ttg gag gat gag        1920
Cys Phe Gln Glu Phe Phe Ala Ala Met Ser Tyr Val Leu Glu Asp Glu
625                  630                  635                  640 aag ggg aga ggt aaa cat tct aat tgc atc ata gat ttg gaa aag acg        1968
Lys Gly Arg Gly Lys His Ser Asn Cys Ile Ile Asp Leu Glu Lys Thr
                        645                  650                  655 cta gaa gca tat gga ata cat ggc ctg ttt ggg gca tca acc aca cgt        2016
Leu Glu Ala Tyr Gly Ile His Gly Leu Phe Gly Ala Ser Thr Thr Arg
                660                  665                  670 ttc cta ttg ggc ctg tta agt gat gag ggg gag aga gag atg gag aac        2064
Phe Leu Leu Gly Leu Leu Ser Asp Glu Gly Glu Arg Glu Met Glu Asn
            675                  680                  685 atc ttt cac tgc cgg ctg tct cag ggg agg aac ctg atg cag tgg gtc        2112
Ile Phe His Cys Arg Leu Ser Gln Gly Arg Asn Leu Met Gln Trp Val
        690                  695                  700 ccg tcc ctg cag ctg ctg cag cca cac tct ctg gag tcc ctc cac            2160
Pro Ser Leu Gln Leu Leu Leu Gln Pro His Ser Leu Glu Ser Leu His
705                  710                  715                  720 tgc ttg tac gag act cgg aac aaa acg ttc ctg aca caa gtg atg gcc        2208
Cys Leu Tyr Glu Thr Arg Asn Lys Thr Phe Leu Thr Gln Val Met Ala
                        725                  730                  735 cat ttc gaa gaa atg ggc atg tgt gta gaa aca gac atg gag ctc tta        2256
His Phe Glu Glu Met Gly Met Cys Val Glu Thr Asp Met Glu Leu Leu
                740                  745                  750 gtg tgc act ttc tgc att aaa ttc agc cgc cac gtg aag aag ctt cag        2304
Val Cys Thr Phe Cys Ile Lys Phe Ser Arg His Val Lys Lys Leu Gln
            755                  760                  765 ctg att gag ggc agg cag cac aga tca aca tgg agc ccc acc atg gta        2352
Leu Ile Glu Gly Arg Gln His Arg Ser Thr Trp Ser Pro Thr Met Val
        770                  775                  780 gtc ctg ttc agg tgg gtc cca gtc aca gat gcc tat tgg cag att ctc        2400
Val Leu Phe Arg Trp Val Pro Val Thr Asp Ala Tyr Trp Gln Ile Leu
785                  790                  795                  800 ttc tcc gtc ctc aag gtc acc aga aac ctg aag gag ctg gac cta agt        2448
Phe Ser Val Leu Lys Val Thr Arg Asn Leu Lys Glu Leu Asp Leu Ser
                        805                  810                  815 gga aac tcg ctg agc cac tct gca gtg aag agt ctt tgt aag acc ctg        2496
Gly Asn Ser Leu Ser His Ser Ala Val Lys Ser Leu Cys Lys Thr Leu
                820                  825                  830 aga cgc cct cgc tgc ctc ctg gag acc ctg cgg ttg gct ggc tgt ggc        2544
Arg Arg Pro Arg Cys Leu Leu Glu Thr Leu Arg Leu Ala Gly Cys Gly
            835                  840                  845 ctc aca gct gag gac tgc aag gac ctt gcc ttt ggg ctg aga gcc aac        2592
Leu Thr Ala Glu Asp Cys Lys Asp Leu Ala Phe Gly Leu Arg Ala Asn
850                  855                  860 cag acc ctg acc gag ctg gac ctg agc ttc aat gtg ctc acg gat gct        2640
Gln Thr Leu Thr Glu Leu Asp Leu Ser Phe Asn Val Leu Thr Asp Ala
865                  870                  875                  880 gga gcc aaa cac ctt tgc cag aga ctg aga cag ccg agc tgc aag cta        2688
Gly Ala Lys His Leu Cys Gln Arg Leu Arg Gln Pro Ser Cys Lys Leu
                        885                  890                  895 cag cga ctg cag ctg gtc agc tgt ggc ctc acg tct gac tgc tgc cag        2736
Gln Arg Leu Gln Leu Val Ser Cys Gly Leu Thr Ser Asp Cys Cys Gln
                900                  905                  910 gac ctg gcc tct gtg ctt agt gcc agc ccc agc ctg aag gag cta gac        2784
```

```
Asp Leu Ala Ser Val Leu Ser Ala Ser Pro Ser Leu Lys Glu Leu Asp
        915                 920                 925 ctg cag cag aac aac ctg gat gac gtt ggc gtg cga ctg ctc tgt gag         2832
Leu Gln Gln Asn Asn Leu Asp Asp Val Gly Val Arg Leu Leu Cys Glu
        930                 935                 940 ggg ctc agg cat cct gcc tgc aaa ctc ata cgc ctg ggg ctg gac cag         2880
Gly Leu Arg His Pro Ala Cys Lys Leu Ile Arg Leu Gly Leu Asp Gln
945                 950                 955                 960 aca act ctg agt gat gag atg agg cag gaa ctg agg gcc ctg gag cag         2928
Thr Thr Leu Ser Asp Glu Met Arg Gln Glu Leu Arg Ala Leu Glu Gln
                965                 970                 975 gag aaa cct cag ctg ctc atc ttc agc aga cgg aaa cca agt gtg atg         2976
Glu Lys Pro Gln Leu Leu Ile Phe Ser Arg Arg Lys Pro Ser Val Met
        980                 985                 990 acc cct act gag ggc ctg gat acg gga gag atg agt aat agc aca tcc         3024
Thr Pro Thr Glu Gly Leu Asp Thr Gly Glu Met Ser Asn Ser Thr Ser
        995                 1000                1005 tca ctc aag cgg cag aga ctc gga tca gag agg gcg gct tcc cat gtt         3072
Ser Leu Lys Arg Gln Arg Leu Gly Ser Glu Arg Ala Ala Ser His Val
        1010                1015                1020 gct cag gct aat ctc aaa ctc ctg gac gtg agc aag atc ttc cca att         3120
Ala Gln Ala Asn Leu Lys Leu Leu Asp Val Ser Lys Ile Phe Pro Ile
1025                1030                1035                1040 gct gag att gca gag gaa agc tcc cca gag gta gta ccg gtg gaa ctc         3168
Ala Glu Ile Ala Glu Glu Ser Ser Pro Glu Val Val Pro Val Glu Leu
                1045                1050                1055 ttg tgc gtg cct tct cct gcc tct caa ggg gac ctg cat acg aag cct         3216
Leu Cys Val Pro Ser Pro Ala Ser Gln Gly Asp Leu His Thr Lys Pro
        1060                1065                1070 ttg ggg act gac gat gac ttt ctg ggg cct gaa gga aat gtg gat gtt         3264
Leu Gly Thr Asp Asp Asp Phe Leu Gly Pro Glu Gly Asn Val Asp Val
        1075                1080                1085 gag ttg att gat aag agc aca aac aga tac agc gtt tgg ttc ccc act         3312
Glu Leu Ile Asp Lys Ser Thr Asn Arg Tyr Ser Val Trp Phe Pro Thr
        1090                1095                1100 gct ggc tgg tat ctg tgg tca gcc aca ggc ctc ggc ttc ctg gta agg         3360
Ala Gly Trp Tyr Leu Trp Ser Ala Thr Gly Leu Gly Phe Leu Val Arg
1105                1110                1115                1120 gat gag gtc aca gtg acg att gcg ttt ggt tcc tgg agt cag cac ctg         3408
Asp Glu Val Thr Val Thr Ile Ala Phe Gly Ser Trp Ser Gln His Leu
                1125                1130                1135 gcc ctg gac ctg cag cac cat gaa cag tgg ctg gtg ggc ggc ccc ttg         3456
Ala Leu Asp Leu Gln His His Glu Gln Trp Leu Val Gly Gly Pro Leu
        1140                1145                1150 ttt gat gtc act gca gag cca gag gag gct gtc gcc gaa atc cac ctc         3504
Phe Asp Val Thr Ala Glu Pro Glu Glu Ala Val Ala Glu Ile His Leu
        1155                1160                1165 ccc cac ttc atc tcc ctc caa ggt gag gtg gac gtc tcc tgg ttt ctc         3552
Pro His Phe Ile Ser Leu Gln Gly Glu Val Asp Val Ser Trp Phe Leu
        1170                1175                1180 gtt gcc cat ttt aag aat gaa ggg atg gtc ctg gag cat cca gcc cgg         3600
Val Ala His Phe Lys Asn Glu Gly Met Val Leu Glu His Pro Ala Arg
1185                1190                1195                1200 gtg gag cct ttc tat gct gtc ctg gaa agc ccc agc ttc tct ctg atg         3648
Val Glu Pro Phe Tyr Ala Val Leu Glu Ser Pro Ser Phe Ser Leu Met
                1205                1210                1215 ggc atc ctg ctg cgg atc gcc agt ggg act cgc ctc tcc atc ccc atc         3696
Gly Ile Leu Leu Arg Ile Ala Ser Gly Thr Arg Leu Ser Ile Pro Ile
        1220                1225                1230
```

| | | |
|---|---|---|
| act tcc aac aca ttg atc tat tat cac ccc cac ccc gaa gat att aag<br>Thr Ser Asn Thr Leu Ile Tyr Tyr His Pro His Pro Glu Asp Ile Lys<br>    1235                    1240                    1245 | | 3744 |
| ttc cac ttg tac ctt gtc ccc agc gac gcc ttg cta aca aag gcg ata<br>Phe His Leu Tyr Leu Val Pro Ser Asp Ala Leu Leu Thr Lys Ala Ile<br>    1250                    1255                    1260 | | 3792 |
| gat gat gag gaa gat cgc ttc cat ggt gtg cgc ctg cag act tcg ccc<br>Asp Asp Glu Glu Asp Arg Phe His Gly Val Arg Leu Gln Thr Ser Pro<br>1265                    1270                    1275                    1280 | | 3840 |
| cca atg gaa ccc ctg aac ttt ggt tcc agt tat att gtg tct aat tct<br>Pro Met Glu Pro Leu Asn Phe Gly Ser Ser Tyr Ile Val Ser Asn Ser<br>    1285                    1290                    1295 | | 3888 |
| gct aac ctg aaa gta atg ccc aag gag ttg aaa ttg tcc tac agg agc<br>Ala Asn Leu Lys Val Met Pro Lys Glu Leu Lys Leu Ser Tyr Arg Ser<br>    1300                    1305                    1310 | | 3936 |
| cct gga gaa att cag cac ttc tca aaa ttc tat gct ggg cag atg aag<br>Pro Gly Glu Ile Gln His Phe Ser Lys Phe Tyr Ala Gly Gln Met Lys<br>    1315                    1320                    1325 | | 3984 |
| gaa ccc att caa ctt gag att act gaa aaa aga cat ggg act ttg gtg<br>Glu Pro Ile Gln Leu Glu Ile Thr Glu Lys Arg His Gly Thr Leu Val<br>    1330                    1335                    1340 | | 4032 |
| tgg gat act gag gtg aag cca gtg gat ctc cag ctt gta gct gca tca<br>Trp Asp Thr Glu Val Lys Pro Val Asp Leu Gln Leu Val Ala Ala Ser<br>1345                    1350                    1355                    1360 | | 4080 |
| gcc cct cct cct ttc tca ggt gca gcc ttt gtg aag gag aac cac cgg<br>Ala Pro Pro Pro Phe Ser Gly Ala Ala Phe Val Lys Glu Asn His Arg<br>    1365                    1370                    1375 | | 4128 |
| caa ctc caa gcc agg atg ggg gac ctg aaa ggg gtg ctc gat gat ctc<br>Gln Leu Gln Ala Arg Met Gly Asp Leu Lys Gly Val Leu Asp Asp Leu<br>    1380                    1385                    1390 | | 4176 |
| cag gac aat gag gtt ctt act gag aat gag aag gag ctg gtg gag cag<br>Gln Asp Asn Glu Val Leu Thr Glu Asn Glu Lys Glu Leu Val Glu Gln<br>    1395                    1400                    1405 | | 4224 |
| gaa aag aca cgg cag agc aag aat gag gcc ttg ctg agc atg gtg gag<br>Glu Lys Thr Arg Gln Ser Lys Asn Glu Ala Leu Leu Ser Met Val Glu<br>    1410                    1415                    1420 | | 4272 |
| aag aaa ggg gac ctg gcc ctg gac gtg ctc ttc aga agc att agt gaa<br>Lys Lys Gly Asp Leu Ala Leu Asp Val Leu Phe Arg Ser Ile Ser Glu<br>1425                    1430                    1435                    1440 | | 4320 |
| agg gac cct tac ctc gtg tcc tat ctt aga cag cag aat ttg taa<br>Arg Asp Pro Tyr Leu Val Ser Tyr Leu Arg Gln Gln Asn Leu<br>            1445                    1450 | | 4365 |
| aatgagtcag ttaggtagtc tggaagagag aatccagcgt tctcattgga aatggataaa | | 4425 |
| cagaaatgtg atcattgatt tcagtgttca agacagaaga agactgggta acatctatca | | 4485 |
| cacaggcttt caggacagac ttgtaacctg gcatgtacct attgactgta tcctcatgca | | 4545 |
| ttttcctcaa g | | 4556 |

<210> SEQ ID NO 10
<211> LENGTH: 1454
<212> TYPE: PRT
<213> ORGANISM: Artificial Sequence
<220> FEATURE:
<223> OTHER INFORMATION: Description of Artificial Sequence: Synthetic
    Construct

<400> SEQUENCE: 10

Met Ala Gly Gly Ala Trp Gly Arg Leu Ala Cys Tyr Leu Glu Phe Leu
1                  5                    10                  15

Lys Lys Glu Glu Leu Lys Glu Phe Gln Leu Leu Leu Ala Asn Lys Ala

-continued

```
                 20                  25                  30
His Ser Arg Ser Ser Gly Glu Thr Pro Ala Gln Pro Glu Lys Thr
             35                  40                  45
Ser Gly Met Glu Val Ala Ser Tyr Leu Val Ala Gln Tyr Gly Glu Gln
 50                  55                  60
Arg Ala Trp Asp Leu Ala Leu His Thr Trp Glu Gln Met Gly Leu Arg
 65                  70                  75                  80
Ser Leu Cys Ala Gln Ala Gln Glu Gly Ala Gly His Ser Pro Ser Phe
                 85                  90                  95
Pro Tyr Ser Pro Ser Glu Pro His Leu Gly Ser Pro Ser Gln Pro Thr
             100                 105                 110
Ser Thr Ala Val Leu Met Pro Trp Ile His Glu Leu Pro Ala Gly Cys
             115                 120                 125
Thr Gln Gly Ser Glu Arg Arg Val Leu Arg Gln Leu Pro Asp Thr Ser
             130                 135                 140
Gly Arg Arg Trp Arg Glu Ile Ser Ala Ser Leu Leu Tyr Gln Ala Leu
145                 150                 155                 160
Pro Ser Ser Pro Asp His Glu Ser Pro Ser Gln Glu Ser Pro Asn Ala
                 165                 170                 175
Pro Thr Ser Thr Ala Val Leu Gly Ser Trp Gly Ser Pro Pro Gln Pro
             180                 185                 190
Ser Leu Ala Pro Arg Glu Gln Glu Ala Pro Gly Thr Gln Trp Pro Leu
             195                 200                 205
Asp Glu Thr Ser Gly Ile Tyr Tyr Thr Glu Ile Arg Glu Arg Glu Arg
 210                 215                 220
Glu Lys Ser Glu Lys Gly Arg Pro Pro Trp Ala Ala Val Gly Thr
225                 230                 235                 240
Pro Pro Gln Ala His Thr Ser Leu Gln Pro His His Pro Trp Glu
                 245                 250                 255
Pro Ser Val Arg Glu Ser Leu Cys Ser Thr Trp Pro Trp Lys Asn Glu
             260                 265                 270
Asp Phe Asn Gln Lys Phe Thr Gln Leu Leu Leu Gln Arg Pro His
             275                 280                 285
Pro Arg Ser Gln Asp Pro Leu Val Lys Arg Ser Trp Pro Asp Tyr Val
             290                 295                 300
Glu Glu Asn Arg Gly His Leu Ile Glu Ile Arg Asp Leu Phe Gly Pro
305                 310                 315                 320
Gly Leu Asp Thr Gln Pro Arg Ile Val Ile Leu Gln Gly Ala Ala
                 325                 330                 335
Gly Ile Gly Lys Ser Thr Leu Ala Arg Gln Val Lys Glu Ala Trp Gly
             340                 345                 350
Arg Gly Gln Leu Tyr Gly Asp Arg Phe Gln His Val Phe Tyr Phe Ser
             355                 360                 365
Cys Arg Glu Leu Ala Gln Ser Lys Val Val Ser Leu Ala Glu Leu Ile
             370                 375                 380
Gly Lys Asp Gly Thr Ala Thr Pro Ala Pro Ile Arg Gln Ile Leu Ser
385                 390                 395                 400
Arg Pro Glu Arg Leu Leu Phe Ile Leu Asp Gly Val Asp Glu Pro Gly
                 405                 410                 415
Trp Val Leu Gln Glu Pro Ser Ser Glu Leu Cys Leu His Trp Ser Gln
             420                 425                 430
Pro Gln Pro Ala Asp Ala Leu Leu Gly Ser Leu Leu Gly Lys Thr Ile
             435                 440                 445
```

-continued

Leu Pro Glu Ala Ser Phe Leu Ile Thr Ala Arg Thr Thr Ala Leu Gln
    450                 455                 460

Asn Leu Ile Pro Ser Leu Glu Gln Ala Arg Trp Val Glu Val Leu Gly
465                 470                 475                 480

Phe Ser Glu Ser Ser Arg Lys Glu Tyr Phe Tyr Arg Tyr Phe Thr Asp
                485                 490                 495

Glu Arg Gln Ala Ile Arg Ala Phe Arg Leu Val Lys Ser Asn Lys Glu
            500                 505                 510

Leu Trp Ala Leu Cys Leu Val Pro Trp Val Ser Trp Leu Ala Cys Thr
        515                 520                 525

Cys Leu Met Gln Gln Met Lys Arg Lys Glu Lys Leu Thr Leu Thr Ser
    530                 535                 540

Lys Thr Thr Thr Thr Leu Cys Leu His Tyr Leu Ala Gln Ala Leu Gln
545                 550                 555                 560

Ala Gln Pro Leu Gly Pro Gln Leu Arg Asp Leu Cys Ser Leu Ala Ala
                565                 570                 575

Glu Gly Ile Trp Gln Lys Lys Thr Leu Phe Ser Pro Asp Asp Leu Arg
            580                 585                 590

Lys His Gly Leu Asp Gly Ala Ile Ile Ser Thr Phe Leu Lys Met Gly
        595                 600                 605

Ile Leu Gln Glu His Pro Ile Pro Leu Ser Tyr Ser Phe Ile His Leu
    610                 615                 620

Cys Phe Gln Glu Phe Phe Ala Ala Met Ser Tyr Val Leu Glu Asp Glu
625                 630                 635                 640

Lys Gly Arg Gly Lys His Ser Asn Cys Ile Ile Asp Leu Glu Lys Thr
                645                 650                 655

Leu Glu Ala Tyr Gly Ile His Gly Leu Phe Gly Ala Ser Thr Thr Arg
            660                 665                 670

Phe Leu Leu Gly Leu Leu Ser Asp Glu Gly Glu Arg Glu Met Glu Asn
        675                 680                 685

Ile Phe His Cys Arg Leu Ser Gln Gly Arg Asn Leu Met Gln Trp Val
    690                 695                 700

Pro Ser Leu Gln Leu Leu Leu Gln Pro His Ser Leu Glu Ser Leu His
705                 710                 715                 720

Cys Leu Tyr Glu Thr Arg Asn Lys Thr Phe Leu Thr Gln Val Met Ala
                725                 730                 735

His Phe Glu Glu Met Gly Met Cys Val Glu Thr Asp Met Glu Leu Leu
            740                 745                 750

Val Cys Thr Phe Cys Ile Lys Phe Ser Arg His Val Lys Lys Leu Gln
        755                 760                 765

Leu Ile Glu Gly Arg Gln His Arg Ser Thr Trp Ser Pro Thr Met Val
    770                 775                 780

Val Leu Phe Arg Trp Val Pro Val Thr Asp Ala Tyr Trp Gln Ile Leu
785                 790                 795                 800

Phe Ser Val Leu Lys Val Thr Arg Asn Leu Lys Glu Leu Asp Leu Ser
                805                 810                 815

Gly Asn Ser Leu Ser His Ser Ala Val Lys Ser Leu Cys Lys Thr Leu
            820                 825                 830

Arg Arg Pro Arg Cys Leu Leu Glu Thr Leu Arg Leu Ala Gly Cys Gly
        835                 840                 845

Leu Thr Ala Glu Asp Cys Lys Asp Leu Ala Phe Gly Leu Arg Ala Asn
850                 855                 860

-continued

```
Gln Thr Leu Thr Glu Leu Asp Leu Ser Phe Asn Val Leu Thr Asp Ala
865                 870                 875                 880

Gly Ala Lys His Leu Cys Gln Arg Leu Arg Gln Pro Ser Cys Lys Leu
                885                 890                 895

Gln Arg Leu Gln Leu Val Ser Cys Gly Leu Thr Ser Asp Cys Cys Gln
            900                 905                 910

Asp Leu Ala Ser Val Leu Ser Ala Ser Pro Ser Leu Lys Glu Leu Asp
        915                 920                 925

Leu Gln Gln Asn Asn Leu Asp Asp Val Gly Val Arg Leu Leu Cys Glu
    930                 935                 940

Gly Leu Arg His Pro Ala Cys Lys Leu Ile Arg Leu Gly Leu Asp Gln
945                 950                 955                 960

Thr Thr Leu Ser Asp Glu Met Arg Gln Glu Leu Arg Ala Leu Glu Gln
                965                 970                 975

Glu Lys Pro Gln Leu Leu Ile Phe Ser Arg Arg Lys Pro Ser Val Met
            980                 985                 990

Thr Pro Thr Glu Gly Leu Asp Thr Gly Glu Met Ser Asn Ser Thr Ser
        995                 1000                1005

Ser Leu Lys Arg Gln Arg Leu Gly Ser Glu Arg Ala Ala Ser His Val
    1010                1015                1020

Ala Gln Ala Asn Leu Lys Leu Leu Asp Val Ser Lys Ile Phe Pro Ile
1025                1030                1035                1040

Ala Glu Ile Ala Glu Ser Ser Pro Glu Val Val Pro Val Glu Leu
                1045                1050                1055

Leu Cys Val Pro Ser Pro Ala Ser Gln Gly Asp Leu His Thr Lys Pro
            1060                1065                1070

Leu Gly Thr Asp Asp Asp Phe Leu Gly Pro Glu Gly Asn Val Asp Val
        1075                1080                1085

Glu Leu Ile Asp Lys Ser Thr Asn Arg Tyr Ser Val Trp Phe Pro Thr
    1090                1095                1100

Ala Gly Trp Tyr Leu Trp Ser Ala Thr Gly Leu Gly Phe Leu Val Arg
1105                1110                1115                1120

Asp Glu Val Thr Val Thr Ile Ala Phe Gly Ser Trp Ser Gln His Leu
                1125                1130                1135

Ala Leu Asp Leu Gln His His Glu Gln Trp Leu Val Gly Gly Pro Leu
            1140                1145                1150

Phe Asp Val Thr Ala Glu Pro Glu Glu Ala Val Ala Glu Ile His Leu
        1155                1160                1165

Pro His Phe Ile Ser Leu Gln Gly Glu Val Asp Val Ser Trp Phe Leu
    1170                1175                1180

Val Ala His Phe Lys Asn Glu Gly Met Val Leu Glu His Pro Ala Arg
1185                1190                1195                1200

Val Glu Pro Phe Tyr Ala Val Leu Glu Ser Pro Ser Phe Ser Leu Met
                1205                1210                1215

Gly Ile Leu Leu Arg Ile Ala Ser Gly Thr Arg Leu Ser Ile Pro Ile
            1220                1225                1230

Thr Ser Asn Thr Leu Ile Tyr Tyr His Pro His Pro Gly Asp Ile Lys
        1235                1240                1245

Phe His Leu Tyr Leu Val Pro Ser Asp Ala Leu Leu Thr Lys Ala Ile
    1250                1255                1260

Asp Asp Glu Glu Asp Arg Phe His Gly Val Arg Leu Gln Thr Ser Pro
1265                1270                1275                1280

Pro Met Glu Pro Leu Asn Phe Gly Ser Ser Tyr Ile Val Ser Asn Ser
```

```
                  1285                1290                1295
Ala Asn Leu Lys Val Met Pro Lys Glu Leu Lys Leu Ser Tyr Arg Ser
        1300                1305                1310

Pro Gly Glu Ile Gln His Phe Ser Lys Phe Tyr Ala Gly Gln Met Lys
        1315                1320                1325

Glu Pro Ile Gln Leu Glu Ile Thr Glu Lys Arg His Gly Thr Leu Val
        1330                1335                1340

Trp Asp Thr Glu Val Lys Pro Val Asp Leu Gln Leu Val Ala Ala Ser
1345                1350                1355                1360

Ala Pro Pro Phe Ser Gly Ala Ala Phe Val Lys Glu Asn His Arg
        1365                1370                1375

Gln Leu Gln Ala Arg Met Gly Asp Leu Lys Gly Val Leu Asp Asp Leu
        1380                1385                1390

Gln Asp Asn Glu Val Leu Thr Glu Asn Glu Lys Glu Leu Val Glu Gln
        1395                1400                1405

Glu Lys Thr Arg Gln Ser Lys Asn Glu Ala Leu Leu Ser Met Val Glu
        1410                1415                1420

Lys Lys Gly Asp Leu Ala Leu Asp Val Leu Phe Arg Ser Ile Ser Glu
1425                1430                1435                1440

Arg Asp Pro Tyr Leu Val Ser Tyr Leu Arg Gln Gln Asn Leu
                1445                1450

<210> SEQ ID NO 11
<211> LENGTH: 4466
<212> TYPE: DNA
<213> ORGANISM: Artificial Sequence
<220> FEATURE:
<221> NAME/KEY: CDS
<222> LOCATION: (1)..(4272)
<220> FEATURE:
<223> OTHER INFORMATION: Description of Artificial Sequence: Synthetic
      Construct

<400> SEQUENCE: 11 atg gct ggc gga gcc tgg ggc cgc ctg gcc tgt tac ttg gag ttc ctg        48
Met Ala Gly Gly Ala Trp Gly Arg Leu Ala Cys Tyr Leu Glu Phe Leu
  1               5                  10                  15 aag aag gag gag ctg aag gag ttc cag ctt ctg ctc gcc aat aaa gcg        96
Lys Lys Glu Glu Leu Lys Glu Phe Gln Leu Leu Leu Ala Asn Lys Ala
             20                  25                  30 cac tcc agg agc tct tcg ggt gag aca ccc gct cag cca gag aag acg       144
His Ser Arg Ser Ser Ser Gly Glu Thr Pro Ala Gln Pro Glu Lys Thr
         35                  40                  45 agt ggc atg gag gtg gcc tcg tac ctg gtg gct cag tat ggg gag cag       192
Ser Gly Met Glu Val Ala Ser Tyr Leu Val Ala Gln Tyr Gly Glu Gln
     50                  55                  60 cgg gcc tgg gac cta gcc ctc cat acc tgg gag cag atg ggg ctg agg       240
Arg Ala Trp Asp Leu Ala Leu His Thr Trp Glu Gln Met Gly Leu Arg
 65                  70                  75                  80 tca ctg tgc gcc caa gcc cag gaa ggg gca ggc cac tct ccc tca ttc       288
Ser Leu Cys Ala Gln Ala Gln Glu Gly Ala Gly His Ser Pro Ser Phe
                 85                  90                  95 ccc tac agc cca agt gaa ccc cac ctg ggg tct ccc agc caa ccc acc       336
Pro Tyr Ser Pro Ser Glu Pro His Leu Gly Ser Pro Ser Gln Pro Thr
            100                 105                 110 tcc acc gca gtg cta atg ccc tgg atc cat gaa ttg ccg gcg ggg tgc       384
Ser Thr Ala Val Leu Met Pro Trp Ile His Glu Leu Pro Ala Gly Cys
        115                 120                 125 acc cag ggc tca gag aga agg gtt ttg aga cag ctg cct gac aca tct       432
```

-continued

```
                Thr Gln Gly Ser Glu Arg Arg Val Leu Arg Gln Leu Pro Asp Thr Ser
                    130                 135                 140 gga cgc cgc tgg aga gaa atc tct gcc tca ctc ctc tac caa gct ctt         480
Gly Arg Arg Trp Arg Glu Ile Ser Ala Ser Leu Leu Tyr Gln Ala Leu
145                 150                 155                 160 cca agc tcc cca gac cat gag tct cca agc cag gag tca ccc aac gcc         528
Pro Ser Ser Pro Asp His Glu Ser Pro Ser Gln Glu Ser Pro Asn Ala
                165                 170                 175 ccc aca tcc aca gca gtg ctg ggg agc tgg gga tcc cca cct cag ccc         576
Pro Thr Ser Thr Ala Val Leu Gly Ser Trp Gly Ser Pro Pro Gln Pro
            180                 185                 190 agc cta gca ccc aga gag cag gag gct cct ggg acc caa tgg cct ctg         624
Ser Leu Ala Pro Arg Glu Gln Glu Ala Pro Gly Thr Gln Trp Pro Leu
        195                 200                 205 gat gaa acg tca gga att tac tac aca gaa atc aga gaa aga gag aga         672
Asp Glu Thr Ser Gly Ile Tyr Tyr Thr Glu Ile Arg Glu Arg Glu Arg
    210                 215                 220 gag aaa tca gag aaa ggc agg ccc cca tgg gca gcg gtg gta gga acg         720
Glu Lys Ser Glu Lys Gly Arg Pro Pro Trp Ala Ala Val Val Gly Thr
225                 230                 235                 240 ccc cca cag gcg cac acc agc cta cag ccc cac cac cac cca tgg gag         768
Pro Pro Gln Ala His Thr Ser Leu Gln Pro His His His Pro Trp Glu
                245                 250                 255 cct tct gtg aga gag agc ctc tgt tcc aca tgg ccc tgg aaa aat gag         816
Pro Ser Val Arg Glu Ser Leu Cys Ser Thr Trp Pro Trp Lys Asn Glu
            260                 265                 270 gat ttt aac caa aaa ttc aca cag ctg cta ctt cta caa aga cct cac         864
Asp Phe Asn Gln Lys Phe Thr Gln Leu Leu Leu Leu Gln Arg Pro His
        275                 280                 285 ccc aga agc caa gat ccc ctg gtc aag aga agc tgg cct gat tat gtg         912
Pro Arg Ser Gln Asp Pro Leu Val Lys Arg Ser Trp Pro Asp Tyr Val
    290                 295                 300 gag gag aat cga gga cat tta att gag atc aga gac tta ttt ggc cca         960
Glu Glu Asn Arg Gly His Leu Ile Glu Ile Arg Asp Leu Phe Gly Pro
305                 310                 315                 320 ggc ctg gat acc caa gaa cct cgc ata gtc ata ctg cag ggg gct gct        1008
Gly Leu Asp Thr Gln Glu Pro Arg Ile Val Ile Leu Gln Gly Ala Ala
                325                 330                 335 gga att ggg aag tca aca ctg gcc agg cag gtg aag gaa gcc tgg ggg        1056
Gly Ile Gly Lys Ser Thr Leu Ala Arg Gln Val Lys Glu Ala Trp Gly
            340                 345                 350 aga ggc cag ctg tat ggg gac cgc ttc cag cat gtc ttc tac ttc agc        1104
Arg Gly Gln Leu Tyr Gly Asp Arg Phe Gln His Val Phe Tyr Phe Ser
        355                 360                 365 tgc aga gag ctg gcc cag tcc aag gtg gtg agt ctc gct gag ctc atc        1152
Cys Arg Glu Leu Ala Gln Ser Lys Val Val Ser Leu Ala Glu Leu Ile
    370                 375                 380 gga aaa gat ggg aca gcc act ccg gct ccc att aga cag atc ctg tct        1200
Gly Lys Asp Gly Thr Ala Thr Pro Ala Pro Ile Arg Gln Ile Leu Ser
385                 390                 395                 400 agg cca gag cgg ctg ctc ttc atc ctc gat ggt gta gat gag cca gga        1248
Arg Pro Glu Arg Leu Leu Phe Ile Leu Asp Gly Val Asp Glu Pro Gly
                405                 410                 415 tgg gtc ttg cag gag ccg agt tct gag ctc tgt ctg cac tgg agc cag        1296
Trp Val Leu Gln Glu Pro Ser Ser Glu Leu Cys Leu His Trp Ser Gln
            420                 425                 430 cca cag ccg gcg gat gca ctg ctg ggc agt ttg ctg ggg aaa act ata        1344
Pro Gln Pro Ala Asp Ala Leu Leu Gly Ser Leu Leu Gly Lys Thr Ile
        435                 440                 445
```

-continued

| | |
|---|---|
| ctt ccc gag gca tcc ttc ctg atc acg gct cgg acc aca gct ctg cag<br>Leu Pro Glu Ala Ser Phe Leu Ile Thr Ala Arg Thr Thr Ala Leu Gln<br>450                         455                    460 | 1392 |
| aac ctc att cct tct ttg gag cag gca cgt tgg gta gag gtc ctg ggg<br>Asn Leu Ile Pro Ser Leu Glu Gln Ala Arg Trp Val Glu Val Leu Gly<br>465                         470                    475                  480 | 1440 |
| ttc tct gag tcc agc agg aag gaa tat ttc tac aga tat ttc aca gat<br>Phe Ser Glu Ser Ser Arg Lys Glu Tyr Phe Tyr Arg Tyr Phe Thr Asp<br>                      485                    490                    495 | 1488 |
| gaa agg caa gca att aga gcc ttt agg ttg gtc aaa tca aac aaa gag<br>Glu Arg Gln Ala Ile Arg Ala Phe Arg Leu Val Lys Ser Asn Lys Glu<br>            500                    505                    510 | 1536 |
| ctc tgg gcc ctg tgt ctt gtg ccc tgg gtg tcc tgg ctg gcc tgc act<br>Leu Trp Ala Leu Cys Leu Val Pro Trp Val Ser Trp Leu Ala Cys Thr<br>515                         520                    525 | 1584 |
| tgc ctg atg cag cag atg aag cgg aag gaa aaa ctc aca ctg act tcc<br>Cys Leu Met Gln Gln Met Lys Arg Lys Glu Lys Leu Thr Leu Thr Ser<br>530                         535                    540 | 1632 |
| aag acc acc aca acc ctc tgt cta cat tac ctt gcc cag gct ctc caa<br>Lys Thr Thr Thr Thr Leu Cys Leu His Tyr Leu Ala Gln Ala Leu Gln<br>545                         550                    555                  560 | 1680 |
| gct cag cca ttg gga ccc cag ctc aga gac ctc tgc tct ctg gct gct<br>Ala Gln Pro Leu Gly Pro Gln Leu Arg Asp Leu Cys Ser Leu Ala Ala<br>                      565                    570                    575 | 1728 |
| gag ggc atc tgg caa aaa aag acc ctt ttc agt cca gat gac ctc agg<br>Glu Gly Ile Trp Gln Lys Lys Thr Leu Phe Ser Pro Asp Asp Leu Arg<br>                    580                    585                    590 | 1776 |
| aag cat ggg tta gat ggg gcc atc atc tcc acc ttc ttg aag atg ggt<br>Lys His Gly Leu Asp Gly Ala Ile Ile Ser Thr Phe Leu Lys Met Gly<br>            595                    600                    605 | 1824 |
| att ctt caa gag cac ccc atc cct ctg agc tac agc ttc att cac ctc<br>Ile Leu Gln Glu His Pro Ile Pro Leu Ser Tyr Ser Phe Ile His Leu<br>610                         615                    620 | 1872 |
| tgt ttc caa gag ttc ttt gca gca atg tcc tat gtc ttg gag gat gag<br>Cys Phe Gln Glu Phe Phe Ala Ala Met Ser Tyr Val Leu Glu Asp Glu<br>625                         630                    635                  640 | 1920 |
| aag ggg aga ggt aaa cat tct aat tgc atc ata gat ttg gaa aag acg<br>Lys Gly Arg Gly Lys His Ser Asn Cys Ile Ile Asp Leu Glu Lys Thr<br>                      645                    650                    655 | 1968 |
| cta gaa gca tat gga ata cat ggc ctg ttt ggg gca tca acc aca cgt<br>Leu Glu Ala Tyr Gly Ile His Gly Leu Phe Gly Ala Ser Thr Thr Arg<br>            660                    665                    670 | 2016 |
| ttc cta ttg ggc ctg tta agt gat gag ggg gag aga gag atg gag aac<br>Phe Leu Leu Gly Leu Leu Ser Asp Glu Gly Glu Arg Glu Met Glu Asn<br>675                         680                    685 | 2064 |
| atc ttt cac tgc cgg ctg tct cag ggg agg aac ctg atg cag tgg gtc<br>Ile Phe His Cys Arg Leu Ser Gln Gly Arg Asn Leu Met Gln Trp Val<br>690                         695                    700 | 2112 |
| ccg tcc ctg cag ctg ctg ctg cag cca cac tct ctg gag tcc ctc cac<br>Pro Ser Leu Gln Leu Leu Leu Gln Pro His Ser Leu Glu Ser Leu His<br>705                         710                    715                  720 | 2160 |
| tgc ttg tac gag act cgg aac aaa acg ttc ctg aca caa gtg atg gcc<br>Cys Leu Tyr Glu Thr Arg Asn Lys Thr Phe Leu Thr Gln Val Met Ala<br>                      725                    730                    735 | 2208 |
| cat ttc gaa gaa atg ggc atg tgt gta gaa aca gac atg gag ctc tta<br>His Phe Glu Glu Met Gly Met Cys Val Glu Thr Asp Met Glu Leu Leu<br>                    740                    745                    750 | 2256 |
| gtg tgc act ttc tgc att aaa ttc agc cgc cac gtg aag aag ctt cag<br>Val Cys Thr Phe Cys Ile Lys Phe Ser Arg His Val Lys Lys Leu Gln<br>755                         760                    765 | 2304 |

-continued

| | |
|---|---|
| ctg att gag ggc agg cag cac aga tca aca tgg agc ccc acc atg gta<br>Leu Ile Glu Gly Arg Gln His Arg Ser Thr Trp Ser Pro Thr Met Val<br>770                                     775                         780 | 2352 |
| gtc ctg ttc agg tgg gtc cca gtc aca gat gcc tat tgg cag att ctc<br>Val Leu Phe Arg Trp Val Pro Val Thr Asp Ala Tyr Trp Gln Ile Leu<br>785                                     790                       795                    800 | 2400 |
| ttc tcc gtc ctc aag gtc acc aga aac ctg aag gag ctg gac cta agt<br>Phe Ser Val Leu Lys Val Thr Arg Asn Leu Lys Glu Leu Asp Leu Ser<br>                          805                       810                       815 | 2448 |
| gga aac tcg ctg agc cac tct gca gtg aag agt ctt tgt aag acc ctg<br>Gly Asn Ser Leu Ser His Ser Ala Val Lys Ser Leu Cys Lys Thr Leu<br>    820                       825                       830 | 2496 |
| aga cgc cct cgc tgc ctc ctg gag acc ctg cgg ttg gct ggc tgt ggc<br>Arg Arg Pro Arg Cys Leu Leu Glu Thr Leu Arg Leu Ala Gly Cys Gly<br>              835                       840                       845 | 2544 |
| ctc aca gct gag gac tgc aag gac ctt gcc ttt ggg ctg aga gcc aac<br>Leu Thr Ala Glu Asp Cys Lys Asp Leu Ala Phe Gly Leu Arg Ala Asn<br>850                                     855                       860 | 2592 |
| cag acc ctg acc gag ctg gac ctg agc ttc aat gtg ctc acg gat gct<br>Gln Thr Leu Thr Glu Leu Asp Leu Ser Phe Asn Val Leu Thr Asp Ala<br>865                               870                       875                    880 | 2640 |
| gga gcc aaa cac ctt tgc cag aga ctg aga cag ccg agc tgc aag cta<br>Gly Ala Lys His Leu Cys Gln Arg Leu Arg Gln Pro Ser Cys Lys Leu<br>                        885                       890                       895 | 2688 |
| cag cga ctg cag ctg gtc agc tgt ggc ctc acg tct gac tgc tgc cag<br>Gln Arg Leu Gln Leu Val Ser Cys Gly Leu Thr Ser Asp Cys Cys Gln<br>            900                       905                       910 | 2736 |
| gac ctg gcc tct gtg ctt agt gcc agc ccc agc ctg aag gag cta gac<br>Asp Leu Ala Ser Val Leu Ser Ala Ser Pro Ser Leu Lys Glu Leu Asp<br>              915                       920                       925 | 2784 |
| ctg cag cag aac aac ctg gat gac gtt ggc gtg cga ctg ctc tgt gag<br>Leu Gln Gln Asn Asn Leu Asp Asp Val Gly Val Arg Leu Leu Cys Glu<br>930                                   935                       940 | 2832 |
| ggg ctc agg cat cct gcc tgc aaa ctc ata cgc ctg ggg aaa cca agt<br>Gly Leu Arg His Pro Ala Cys Lys Leu Ile Arg Leu Gly Lys Pro Ser<br>945                                   950                       955                    960 | 2880 |
| gtg atg acc cct act gag ggc ctg gat acg gga gag atg agt aat agc<br>Val Met Thr Pro Thr Glu Gly Leu Asp Thr Gly Glu Met Ser Asn Ser<br>                        965                       970                       975 | 2928 |
| aca tcc tca ctc aag cgg cag aga ctc gga tca gag agg gcg gct tcc<br>Thr Ser Ser Leu Lys Arg Gln Arg Leu Gly Ser Glu Arg Ala Ala Ser<br>                        980                       985                       990 | 2976 |
| cat gtt gct cag gct aat ctc aaa ctc ctg gac gtg agc aag atc ttc<br>His Val Ala Gln Ala Asn Leu Lys Leu Leu Asp Val Ser Lys Ile Phe<br>              995                     1000                    1005 | 3024 |
| cca att gct gag att gca gag gaa agc tcc cca gag gta gta ccg gtg<br>Pro Ile Ala Glu Ile Ala Glu Glu Ser Ser Pro Glu Val Val Pro Val<br>1010                               1015                    1020 | 3072 |
| gaa ctc ttg tgc gtg cct tct cct gcc tct caa ggg gac ctg cat acg<br>Glu Leu Leu Cys Val Pro Ser Pro Ala Ser Gln Gly Asp Leu His Thr<br>1025                               1030                    1035                    1040 | 3120 |
| aag cct ttg ggg act gac gat gac ttt ctg ggg cct gaa gga aat gtg<br>Lys Pro Leu Gly Thr Asp Asp Asp Phe Leu Gly Pro Glu Gly Asn Val<br>                        1045                    1050                    1055 | 3168 |
| gat gtt gag ttg att gat aag agc aca aac aga tac agc gtt tgg ttc<br>Asp Val Glu Leu Ile Asp Lys Ser Thr Asn Arg Tyr Ser Val Trp Phe<br>           1060                    1065                    1070 | 3216 |
| ccc act gct ggc tgg tat ctg tgg tca gcc aca ggc ctc ggc ttc ctg<br>Pro Thr Ala Gly Trp Tyr Leu Trp Ser Ala Thr Gly Leu Gly Phe Leu | 3264 |

```
                                         -continued
         1075              1080              1085
gta agg gat gag gtc aca gtg acg att gcg ttt ggt tcc tgg agt cag        3312
Val Arg Asp Glu Val Thr Val Thr Ile Ala Phe Gly Ser Trp Ser Gln
    1090              1095              1100 cac ctg gcc ctg gac ctg cag cac cat gaa cag tgg ctg gtg ggc ggc        3360
His Leu Ala Leu Asp Leu Gln His His Glu Gln Trp Leu Val Gly Gly
1105              1110              1115              1120 ccc ttg ttt gat gtc act gca gag cca gag gag gct gtc gcc gaa atc        3408
Pro Leu Phe Asp Val Thr Ala Glu Pro Glu Glu Ala Val Ala Glu Ile
             1125              1130              1135 cac ctc ccc cac ttc atc tcc ctc caa ggt gag gtg gac gtc tcc tgg        3456
His Leu Pro His Phe Ile Ser Leu Gln Gly Glu Val Asp Val Ser Trp
         1140              1145              1150 ttt ctc gtt gcc cat ttt aag aat gaa ggg atg gtc ctg gag cat cca        3504
Phe Leu Val Ala His Phe Lys Asn Glu Gly Met Val Leu Glu His Pro
     1155              1160              1165 gcc cgg gtg gag cct ttc tat gct gtc ctg gaa agc ccc agc ttc tct        3552
Ala Arg Val Glu Pro Phe Tyr Ala Val Leu Glu Ser Pro Ser Phe Ser
 1170              1175              1180 ctg atg ggc atc ctg ctg cgg atc gcc agt ggg act cgc ctc tcc atc        3600
Leu Met Gly Ile Leu Leu Arg Ile Ala Ser Gly Thr Arg Leu Ser Ile
1185              1190              1195              1200 ccc atc act tcc aac aca ttg atc tat tat cac ccc cac ccc gaa gat        3648
Pro Ile Thr Ser Asn Thr Leu Ile Tyr Tyr His Pro His Pro Glu Asp
             1205              1210              1215 att aag ttc cac ttg tac ctt gtc ccc agc gac gcc ttg cta aca aag        3696
Ile Lys Phe His Leu Tyr Leu Val Pro Ser Asp Ala Leu Leu Thr Lys
         1220              1225              1230 gcg ata gat gat gag gaa gat cgc ttc cat ggt gtg cgc ctg cag act        3744
Ala Ile Asp Asp Glu Glu Asp Arg Phe His Gly Val Arg Leu Gln Thr
     1235              1240              1245 tcg ccc cca atg gaa ccc ctg aac ttt ggt tcc agt tat att gtg tct        3792
Ser Pro Pro Met Glu Pro Leu Asn Phe Gly Ser Ser Tyr Ile Val Ser
 1250              1255              1260 aat tct gct aac ctg aaa gta atg ccc aag gag ttg aaa ttg tcc tac        3840
Asn Ser Ala Asn Leu Lys Val Met Pro Lys Glu Leu Lys Leu Ser Tyr
1265              1270              1275              1280 agg agc cct gga gaa att cag cac ttc tca aaa ttc tat gct ggg cag        3888
Arg Ser Pro Gly Glu Ile Gln His Phe Ser Lys Phe Tyr Ala Gly Gln
             1285              1290              1295 atg aag gaa ccc att caa ctt gag att act gaa aaa aga cat ggg act        3936
Met Lys Glu Pro Ile Gln Leu Glu Ile Thr Glu Lys Arg His Gly Thr
         1300              1305              1310 ttg gtg tgg gat act gag gtg aag cca gtg gat ctc cag ctt gta gct        3984
Leu Val Trp Asp Thr Glu Val Lys Pro Val Asp Leu Gln Leu Val Ala
     1315              1320              1325 gca tca gcc cct cct cct ttc tca ggt gca gcc ttt gtg aag gag aac        4032
Ala Ser Ala Pro Pro Pro Phe Ser Gly Ala Ala Phe Val Lys Glu Asn
 1330              1335              1340 cac cgg caa ctc caa gcc agg atg ggg gac ctg aaa ggg gtg ctc gat        4080
His Arg Gln Leu Gln Ala Arg Met Gly Asp Leu Lys Gly Val Leu Asp
1345              1350              1355              1360 gat ctc cag gac aat gag gtt ctt act gag aat gag aag gag ctg gtg        4128
Asp Leu Gln Asp Asn Glu Val Leu Thr Glu Asn Glu Lys Glu Leu Val
             1365              1370              1375 gag cag gaa aag aca cgg cag agc aag aat gag gcc ttg ctg agc atg        4176
Glu Gln Glu Lys Thr Arg Gln Ser Lys Asn Glu Ala Leu Leu Ser Met
         1380              1385              1390 gtg gag aag aaa ggg gac ctg gcc ctg gac gtg ctc ttc aga agc att        4224
```

-continued

```
Val Glu Lys Lys Gly Asp Leu Ala Leu Asp Val Leu Phe Arg Ser Ile
    1395                1400                1405 agt gaa agg gac cct tac ctc gtg tcc tat ctt aga cag cag aat ttg      4272
Ser Glu Arg Asp Pro Tyr Leu Val Ser Tyr Leu Arg Gln Gln Asn Leu
    1410                1415                1420 taaaatgagt cagttaggta gtctggaaga gagaatccag cgttctcatt ggaaatggat    4332
aaacagaaat gtgatcattg atttcagtgt tcaagacaga agaagactgg gtaacatcta   4392
tcacacaggc tttcaggaca gacttgtaac ctggcatgta cctattgact gtatcctcat   4452
gcattttcct caag                                                      4466

<210> SEQ ID NO 12
<211> LENGTH: 1424
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 12

Met Ala Gly Gly Ala Trp Gly Arg Leu Ala Cys Tyr Leu Glu Phe Leu
1               5                   10                  15

Lys Lys Glu Glu Leu Lys Glu Phe Gln Leu Leu Leu Ala Asn Lys Ala
            20                  25                  30

His Ser Arg Ser Ser Ser Gly Glu Thr Pro Ala Gln Pro Glu Lys Thr
        35                  40                  45

Ser Gly Met Glu Val Ala Ser Tyr Leu Val Ala Gln Tyr Gly Glu Gln
    50                  55                  60

Arg Ala Trp Asp Leu Ala Leu His Thr Trp Glu Gln Met Gly Leu Arg
65                  70                  75                  80

Ser Leu Cys Ala Gln Ala Gln Glu Gly Ala Gly His Ser Pro Ser Phe
                85                  90                  95

Pro Tyr Ser Pro Ser Glu Pro His Leu Gly Ser Pro Ser Gln Pro Thr
            100                 105                 110

Ser Thr Ala Val Leu Met Pro Trp Ile His Glu Leu Pro Ala Gly Cys
        115                 120                 125

Thr Gln Gly Ser Glu Arg Arg Val Leu Arg Gln Leu Pro Asp Thr Ser
    130                 135                 140

Gly Arg Arg Trp Arg Glu Ile Ser Ala Ser Leu Leu Tyr Gln Ala Leu
145                 150                 155                 160

Pro Ser Ser Pro Asp His Glu Ser Pro Ser Gln Glu Ser Pro Asn Ala
                165                 170                 175

Pro Thr Ser Thr Ala Val Leu Gly Ser Trp Gly Ser Pro Pro Gln Pro
            180                 185                 190

Ser Leu Ala Pro Arg Glu Gln Glu Ala Pro Gly Thr Gln Trp Pro Leu
        195                 200                 205

Asp Glu Thr Ser Gly Ile Tyr Tyr Thr Glu Ile Arg Glu Arg Glu Arg
    210                 215                 220

Glu Lys Ser Glu Lys Gly Arg Pro Pro Trp Ala Ala Val Val Gly Thr
225                 230                 235                 240

Pro Pro Gln Ala His Thr Ser Leu Gln Pro His His Pro Trp Glu
                245                 250                 255

Pro Ser Val Arg Glu Ser Leu Cys Ser Thr Trp Pro Trp Lys Asn Glu
            260                 265                 270

Asp Phe Asn Gln Lys Phe Thr Gln Leu Leu Leu Leu Gln Arg Pro His
        275                 280                 285
```

-continued

```
Pro Arg Ser Gln Asp Pro Leu Val Lys Arg Ser Trp Pro Asp Tyr Val
290                 295                 300

Glu Glu Asn Arg Gly His Leu Ile Glu Ile Arg Asp Leu Phe Gly Pro
305                 310                 315                 320

Gly Leu Asp Thr Gln Glu Pro Arg Ile Val Ile Leu Gln Gly Ala Ala
                325                 330                 335

Gly Ile Gly Lys Ser Thr Leu Ala Arg Gln Val Lys Glu Ala Trp Gly
                340                 345                 350

Arg Gly Gln Leu Tyr Gly Asp Arg Phe Gln His Val Phe Tyr Phe Ser
                355                 360                 365

Cys Arg Glu Leu Ala Gln Ser Lys Val Val Ser Leu Ala Glu Leu Ile
        370                 375                 380

Gly Lys Asp Gly Thr Ala Thr Pro Ala Pro Ile Arg Gln Ile Leu Ser
385                 390                 395                 400

Arg Pro Glu Arg Leu Leu Phe Ile Leu Asp Gly Val Asp Glu Pro Gly
                405                 410                 415

Trp Val Leu Gln Glu Pro Ser Ser Glu Leu Cys Leu His Trp Ser Gln
                420                 425                 430

Pro Gln Pro Ala Asp Ala Leu Leu Gly Ser Leu Leu Gly Lys Thr Ile
                435                 440                 445

Leu Pro Glu Ala Ser Phe Leu Ile Thr Ala Arg Thr Thr Ala Leu Gln
450                 455                 460

Asn Leu Ile Pro Ser Leu Glu Gln Ala Arg Trp Val Glu Val Leu Gly
465                 470                 475                 480

Phe Ser Glu Ser Ser Arg Lys Glu Tyr Phe Tyr Arg Tyr Phe Thr Asp
                485                 490                 495

Glu Arg Gln Ala Ile Arg Ala Phe Arg Leu Val Lys Ser Asn Lys Glu
                500                 505                 510

Leu Trp Ala Leu Cys Leu Val Pro Trp Val Ser Trp Leu Ala Cys Thr
                515                 520                 525

Cys Leu Met Gln Gln Met Lys Arg Lys Glu Lys Leu Thr Leu Thr Ser
                530                 535                 540

Lys Thr Thr Thr Thr Leu Cys Leu His Tyr Leu Ala Gln Ala Leu Gln
545                 550                 555                 560

Ala Gln Pro Leu Gly Pro Gln Leu Arg Asp Leu Cys Ser Leu Ala Ala
                565                 570                 575

Glu Gly Ile Trp Gln Lys Lys Thr Leu Phe Ser Pro Asp Asp Leu Arg
                580                 585                 590

Lys His Gly Leu Asp Gly Ala Ile Ile Ser Thr Phe Leu Lys Met Gly
                595                 600                 605

Ile Leu Gln Glu His Pro Ile Pro Leu Ser Tyr Ser Phe Ile His Leu
        610                 615                 620

Cys Phe Gln Glu Phe Ala Ala Met Ser Tyr Val Leu Glu Asp Glu
625                 630                 635                 640

Lys Gly Arg Gly Lys His Ser Asn Cys Ile Ile Asp Leu Glu Lys Thr
                645                 650                 655

Leu Glu Ala Tyr Gly Ile His Gly Leu Phe Gly Ala Ser Thr Thr Arg
                660                 665                 670

Phe Leu Leu Gly Leu Leu Ser Asp Glu Gly Glu Arg Glu Met Glu Asn
                675                 680                 685

Ile Phe His Cys Arg Leu Ser Gln Gly Arg Asn Leu Met Gln Trp Val
690                 695                 700
```

-continued

```
Pro Ser Leu Gln Leu Leu Leu Gln Pro His Ser Leu Glu Ser Leu His
705                 710                 715                 720

Cys Leu Tyr Glu Thr Arg Asn Lys Thr Phe Leu Thr Gln Val Met Ala
            725                 730                 735

His Phe Glu Glu Met Gly Met Cys Val Glu Thr Asp Met Glu Leu Leu
        740                 745                 750

Val Cys Thr Phe Cys Ile Lys Phe Ser Arg His Val Lys Lys Leu Gln
    755                 760                 765

Leu Ile Glu Gly Arg Gln His Arg Ser Thr Trp Ser Pro Thr Met Val
770                 775                 780

Val Leu Phe Arg Trp Val Pro Val Thr Asp Ala Tyr Trp Gln Ile Leu
785                 790                 795                 800

Phe Ser Val Leu Lys Val Thr Arg Asn Leu Lys Glu Leu Asp Leu Ser
                805                 810                 815

Gly Asn Ser Leu Ser His Ser Ala Val Lys Ser Leu Cys Lys Thr Leu
            820                 825                 830

Arg Arg Pro Arg Cys Leu Leu Glu Thr Leu Arg Leu Ala Gly Cys Gly
        835                 840                 845

Leu Thr Ala Glu Asp Cys Lys Asp Leu Ala Phe Gly Leu Arg Ala Asn
    850                 855                 860

Gln Thr Leu Thr Glu Leu Asp Leu Ser Phe Asn Val Leu Thr Asp Ala
865                 870                 875                 880

Gly Ala Lys His Leu Cys Gln Arg Leu Arg Gln Pro Ser Cys Lys Leu
                885                 890                 895

Gln Arg Leu Gln Leu Val Ser Cys Gly Leu Thr Ser Asp Cys Cys Gln
            900                 905                 910

Asp Leu Ala Ser Val Leu Ser Ala Ser Pro Ser Leu Lys Glu Leu Asp
        915                 920                 925

Leu Gln Gln Asn Asn Leu Asp Asp Val Gly Val Arg Leu Leu Cys Glu
    930                 935                 940

Gly Leu Arg His Pro Ala Cys Lys Leu Ile Arg Leu Gly Lys Pro Ser
945                 950                 955                 960

Val Met Thr Pro Thr Glu Gly Leu Asp Thr Gly Glu Met Ser Asn Ser
                965                 970                 975

Thr Ser Ser Leu Lys Arg Gln Arg Leu Gly Ser Glu Arg Ala Ala Ser
            980                 985                 990

His Val Ala Gln Ala Asn Leu Lys Leu Leu Asp Val Ser Lys Ile Phe
        995                 1000                1005

Pro Ile Ala Glu Ile Ala Glu Glu Ser Ser Pro Glu Val Val Pro Val
    1010                1015                1020

Glu Leu Leu Cys Val Pro Ser Pro Ala Ser Gln Gly Asp Leu His Thr
1025                1030                1035                1040

Lys Pro Leu Gly Thr Asp Asp Phe Leu Gly Pro Glu Gly Asn Val
            1045                1050                1055

Asp Val Glu Leu Ile Asp Lys Ser Thr Asn Arg Tyr Ser Val Trp Phe
        1060                1065                1070

Pro Thr Ala Gly Trp Tyr Leu Trp Ser Ala Thr Gly Leu Gly Phe Leu
    1075                1080                1085

Val Arg Asp Glu Val Thr Val Thr Ile Ala Phe Gly Ser Trp Ser Gln
    1090                1095                1100

His Leu Ala Leu Asp Leu Gln His His Glu Gln Trp Leu Val Gly Gly
1105                1110                1115                1120

Pro Leu Phe Asp Val Thr Ala Glu Pro Glu Glu Ala Val Ala Glu Ile
```

-continued

```
                    1125                1130                1135

His Leu Pro His Phe Ile Ser Leu Gln Gly Glu Val Asp Val Ser Trp
        1140                1145                1150

Phe Leu Val Ala His Phe Lys Asn Glu Gly Met Val Leu Glu His Pro
    1155                1160                1165

Ala Arg Val Glu Pro Phe Tyr Ala Val Leu Glu Ser Pro Ser Phe Ser
    1170                1175                1180

Leu Met Gly Ile Leu Leu Arg Ile Ala Ser Gly Thr Arg Leu Ser Ile
1185                1190                1195                1200

Pro Ile Thr Ser Asn Thr Leu Ile Tyr Tyr His Pro His Pro Glu Asp
            1205                1210                1215

Ile Lys Phe His Leu Tyr Leu Val Pro Ser Asp Ala Leu Leu Thr Lys
        1220                1225                1230

Ala Ile Asp Asp Glu Glu Asp Arg Phe His Gly Val Arg Leu Gln Thr
    1235                1240                1245

Ser Pro Pro Met Glu Pro Leu Asn Phe Gly Ser Ser Tyr Ile Val Ser
    1250                1255                1260

Asn Ser Ala Asn Leu Lys Val Met Pro Lys Glu Leu Lys Leu Ser Tyr
1265                1270                1275                1280

Arg Ser Pro Gly Glu Ile Gln His Phe Ser Lys Phe Tyr Ala Gly Gln
            1285                1290                1295

Met Lys Glu Pro Ile Gln Leu Glu Ile Thr Glu Lys Arg His Gly Thr
        1300                1305                1310

Leu Val Trp Asp Thr Glu Val Lys Pro Val Asp Leu Gln Leu Val Ala
    1315                1320                1325

Ala Ser Ala Pro Pro Pro Phe Ser Gly Ala Ala Phe Val Lys Glu Asn
    1330                1335                1340

His Arg Gln Leu Gln Ala Arg Met Gly Asp Leu Lys Gly Val Leu Asp
1345                1350                1355                1360

Asp Leu Gln Asp Asn Glu Val Leu Thr Glu Asn Glu Lys Glu Leu Val
            1365                1370                1375

Glu Gln Glu Lys Thr Arg Gln Ser Lys Asn Glu Ala Leu Leu Ser Met
        1380                1385                1390

Val Glu Lys Lys Gly Asp Leu Ala Leu Asp Val Leu Phe Arg Ser Ile
    1395                1400                1405

Ser Glu Arg Asp Pro Tyr Leu Val Ser Tyr Leu Arg Gln Gln Asn Leu
    1410                1415                1420
```

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 13
ccgaattcac catggctggc ggagcctggg gc                               32

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 14
ccgctcgagt caacagaggg ttgtggtggt cttg                             34

```
<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 15
cccgaattcg aacctcgcat agtcatactg c                              31

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 16
gtcccacaac agaattcaat ctcaacggtc                                30

<210> SEQ ID NO 17
<211> LENGTH: 21
<212> TYPE: DNA
<213> ORGANISM: Homo sapiens

<400> SEQUENCE: 17
tgtgatgaga gaagcggtga c                                         21

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 18
ccgctcgagc aaagaagggt cagccaaagc                                30

<210> SEQ ID NO 19
<211> LENGTH: 209
<212> TYPE: PRT
<213> ORGANISM: Homo sapiens

<400> SEQUENCE: 19

Ile Val Ile Leu Gln Gly Ala Ala Gly Ile Gly Lys Ser Ile Leu Ala
  1               5                  10                  15

Arg Gln Val Lys Glu Ala Trp Gly Arg Gly Gln Leu Tyr Gly Asp Arg
                 20                  25                  30

Phe Gln His Val Phe Tyr Phe Ser Cys Arg Glu Leu Ala Gln Ser Lys
             35                  40                  45

Val Val Ser Leu Ala Glu Leu Ile Gly Lys Asp Gly Thr Ala Thr Pro
         50                  55                  60

Ala Pro Ile Arg Gln Ile Leu Ser Arg Pro Glu Arg Leu Leu Phe Ile
 65                  70                  75                  80

Leu Asp Gly Val Asp Glu Pro Gly Trp Val Leu Gln Glu Pro Ser Ser
                 85                  90                  95

Glu Leu Cys Leu His Trp Ser Gln Pro Gln Pro Ala Asp Ala Leu Leu
            100                 105                 110

Gly Ser Leu Leu Gly Lys Thr Ile Leu Pro Glu Ala Ser Phe Leu Ile
        115                 120                 125
```

```
Thr Ala Arg Thr Thr Ala Leu Gln Asn Leu Ile Pro Ser Leu Glu Gln
    130                 135                 140

Ala Arg Trp Val Glu Val Leu Gly Phe Ser Glu Ser Arg Lys Glu
145                 150                 155                 160

Tyr Phe Tyr Arg Tyr Phe Thr Asp Glu Arg Gln Ala Ile Arg Ala Phe
                165                 170                 175

Arg Leu Val Lys Ser Asn Lys Glu Leu Trp Ala Leu Cys Leu Val Pro
                180                 185                 190

Trp Val Ser Trp Leu Ala Cys Thr Cys Leu Met Gln Gln Met Lys Arg
            195                 200                 205

Lys

<210> SEQ ID NO 20
<211> LENGTH: 212
<212> TYPE: PRT
<213> ORGANISM: Homo sapiens

<400> SEQUENCE: 20

Thr Ile Phe Ile Leu Gly Asp Ala Gly Val Gly Lys Ser Met Leu Leu
  1               5                  10                  15

Gln Arg Leu Gln Ser Leu Trp Ala Thr Gly Arg Leu Asp Ala Gly Val
                 20                  25                  30

Lys Phe Phe Phe His Phe Arg Cys Arg Met Phe Ser Cys Phe Lys Glu
             35                  40                  45

Ser Asp Arg Leu Cys Leu Gln Asp Leu Leu Phe Lys His Tyr Cys Tyr
 50                  55                  60

Pro Glu Arg Asp Pro Glu Val Phe Ala Phe Leu Arg Phe Pro
65                   70                  75                  80

His Val Ala Leu Phe Thr Phe Asp Gly Leu Asp Glu Leu His Ser Asp
                 85                  90                  95

Leu Asp Leu Ser Arg Val Pro Asp Ser Ser Cys Pro Trp Glu Pro Ala
                100                 105                 110

His Pro Leu Val Leu Leu Ala Asn Leu Leu Ser Gly Lys Leu Leu Lys
            115                 120                 125

Gly Ala Ser Lys Leu Leu Thr Ala Arg Thr Gly Ile Glu Val Pro Arg
130                 135                 140

Gln Phe Leu Arg Lys Lys Val Leu Leu Arg Gly Phe Ser Pro Ser His
145                 150                 155                 160

Leu Arg Ala Tyr Ala Arg Arg Met Phe Pro Glu Arg Ala Leu Gln Asp
                165                 170                 175

Arg Leu Leu Ser Gln Leu Glu Ala Asn Pro Asn Leu Cys Ser Leu Cys
                180                 185                 190

Ser Val Pro Leu Phe Cys Trp Ile Ile Phe Arg Cys Phe Gln His Phe
            195                 200                 205

Arg Ala Ala Phe
    210

<210> SEQ ID NO 21
<211> LENGTH: 219
<212> TYPE: PRT
<213> ORGANISM: Homo sapiens

<400> SEQUENCE: 21

Trp Val Thr Ile His Gly Met Ala Gly Cys Gly Lys Ser Val Leu Ala
  1               5                  10                  15

Ala Glu Ala Val Arg Asp His Ser Leu Leu Glu Gly Cys Phe Pro Gly
```

```
                    20                      25                      30
Gly Val His Trp Val Ser Val Gly Lys Gln Asp Lys Ser Gly Leu Leu
            35                      40                      45

Met Lys Leu Gln Asn Leu Cys Thr Arg Leu Asp Gln Asp Glu Ser Phe
 50                      55                      60

Ser Gln Arg Leu Pro Leu Asn Ile Glu Glu Ala Lys Asp Arg Leu Arg
 65                      70                      75                      80

Ile Leu Met Leu Arg Lys His Pro Arg Ser Leu Leu Ile Leu Asp Asp
                    85                      90                      95

Val Trp Asp Ser Trp Val Leu Lys Ala Phe Asp Ser Gln Cys Gln Ile
                100                     105                     110

Leu Leu Thr Thr Arg Asp Lys Ser Val Thr Asp Ser Val Met Gly Pro
            115                     120                     125

Lys Tyr Val Val Pro Val Glu Ser Ser Leu Gly Lys Glu Lys Gly Leu
        130                     135                     140

Glu Ile Leu Ser Leu Phe Val Asn Met Lys Lys Ala Asp Leu Pro Glu
145                     150                     155                     160

Gln Ala His Ser Ile Ile Lys Glu Cys Lys Gly Ser Pro Leu Val Val
                165                     170                     175

Ser Leu Ile Gly Ala Leu Leu Arg Asp Phe Pro Asn Arg Trp Glu Tyr
            180                     185                     190

Tyr Leu Lys Gln Leu Gln Asn Lys Gln Phe Lys Arg Ile Arg Lys Ser
        195                     200                     205

Ser Ser Tyr Asp Tyr Glu Ala Leu Asp Glu Ala
        210                     215

<210> SEQ ID NO 22
<211> LENGTH: 221
<212> TYPE: PRT
<213> ORGANISM: Caenorhabditis elegans

<400> SEQUENCE: 22

Phe Leu Phe Leu His Gly Arg Ala Gly Ser Gly Lys Ser Val Ile Ala
  1               5                      10                      15

Ser Gln Ala Leu Ser Lys Ser Asp Gln Leu Ile Gly Ile Asn Tyr Asp
                 20                      25                      30

Ser Ile Val Trp Leu Lys Asp Ser Gly Thr Ala Pro Lys Ser Thr Phe
            35                      40                      45

Asp Leu Phe Thr Asp Ile Leu Leu Met Leu Lys Ser Glu Asp Asp Leu
 50                      55                      60

Leu Asn Phe Pro Ser Val Glu His Val Thr Ser Val Val Leu Lys Arg
 65                      70                      75                      80

Met Ile Cys Asn Ala Leu Ile Asp Arg Pro Asn Thr Leu Phe Val Phe
                    85                      90                      95

Asp Gln Val Val Gln Glu Glu Thr Ile Arg Trp Ala Gln Glu Leu Arg
                100                     105                     110

Leu Arg Cys Leu Val Thr Thr Arg Asp Val Glu Ile Ser Asn Ala Ala
            115                     120                     125

Ser Gln Thr Cys Glu Phe Ile Glu Val Thr Ser Leu Glu Ile Asp Glu
        130                     135                     140

Cys Tyr Asp Phe Leu Glu Ala Tyr Gly Met Pro Met Pro Val Gly Glu
145                     150                     155                     160

Lys Glu Glu Asp Val Leu Asn Lys Thr Ile Glu Leu Ser Ser Gly Asn
                165                     170                     175
```

```
Pro Ala Thr Leu Met Met Phe Lys Ser Cys Glu Pro Lys Thr Phe
            180                 185                 190

Glu Lys Met Ala Gln Leu Asn Asn Lys Leu Glu Ser Arg Gly Leu Asx
            195                 200                 205

Gly Asx Glu Cys Ile Thr Pro Tyr Ser Tyr Lys Ser Leu
    210                 215                 220

<210> SEQ ID NO 23
<211> LENGTH: 91
<212> TYPE: PRT
<213> ORGANISM: Homo sapiens

<400> SEQUENCE: 23

Leu Asp Ala Pro Gln Leu Leu His Phe Val Asp Gln Tyr Arg Glu Gln
  1               5                  10                  15

Leu Ile Ala Arg Val Thr Ser Val Glu Val Leu Asp Lys Leu His
             20                  25                  30

Gly Gln Val Leu Ser Gln Glu Gln Tyr Glu Arg Val Leu Ala Glu Asn
             35                  40                  45

Thr Arg Pro Ser Gln Met Arg Lys Leu Phe Ser Leu Ser Gln Ser Trp
     50                  55                  60

Asp Arg Lys Cys Lys Asp Gly Leu Tyr Gln Ala Leu Lys Glu Thr His
 65                  70                  75                  80

Leu Ile Met Glu Leu Trp Glu Lys Gly Ser Lys
             85                  90

<210> SEQ ID NO 24
<211> LENGTH: 91
<212> TYPE: PRT
<213> ORGANISM: Homo sapiens

<400> SEQUENCE: 24

Met Asp Ala Lys Ala Arg Asn Cys Leu Leu Gln His Arg Glu Ala Leu
  1               5                  10                  15

Glu Lys Asp Ile Lys Thr Ser Tyr Ile Met Asp His Met Ile Ser Asp
             20                  25                  30

Gly Phe Leu Thr Ile Ser Glu Glu Glu Lys Val Arg Asn Glu Pro Thr
             35                  40                  45

Gln Gln Gln Arg Ala Ala Met Leu Ile Lys Met Ile Leu Lys Lys Asp
     50                  55                  60

Asn Asp Ser Tyr Val Ser Phe Tyr Asn Ala Leu Leu His Glu Gly Tyr
 65                  70                  75                  80

Lys Asp Leu Ala Ala Leu Leu His Asp Gly Ile
             85                  90

<210> SEQ ID NO 25
<211> LENGTH: 90
<212> TYPE: PRT
<213> ORGANISM: Caenorhabditis elegans

<400> SEQUENCE: 25

Glu Ser His Pro His Ile Gln Leu Leu Lys Ser Asn Arg Glu Leu Leu
  1               5                  10                  15

Val Thr His Ile Arg Asn Thr Gln Cys Leu Val Asp Asn Leu Leu Lys
             20                  25                  30

Asn Asp Tyr Phe Ser Ala Glu Asp Ala Glu Ile Val Cys Ala Cys Pro
             35                  40                  45

Thr Gln Pro Asp Lys Tyr Arg Lys Ile Leu Asp Leu Val Gln Ser Lys
```

```
            50                  55                  60
Gly Glu Glu Val Ser Glu Phe Phe Leu Tyr Leu Leu Gln Gln Leu Ala
 65                  70                  75                  80

Asp Ala Tyr Val Asp Leu Arg Pro Trp Leu
                 85                  90

<210> SEQ ID NO 26
<211> LENGTH: 88
<212> TYPE: PRT
<213> ORGANISM: Caenorhabditis elegans

<400> SEQUENCE: 26

Leu Cys Glu Ile Glu Cys Arg Ala Leu Ser Thr His Thr Arg Leu Ile
 1               5                  10                  15

His Asp Phe Glu Pro Arg Asp Ala Leu Thr Tyr Leu Glu Gly Lys Asn
             20                  25                  30

Ile Phe Thr Glu His Ser Glu Leu Ile Ser Lys Met Ser Thr Arg Leu
         35                  40                  45

Glu Arg Ile Ala Asn Phe Leu Arg Ile Tyr Arg Arg Gln Ala Ser Glu
     50                  55                  60

Leu Gly Pro Leu Ile Asp Phe Phe Asn Tyr Asn Asn Gln Ser His Leu
 65                  70                  75                  80

Ala Asp Phe Leu Glu Gln Tyr Ile
                 85

<210> SEQ ID NO 27
<211> LENGTH: 91
<212> TYPE: PRT
<213> ORGANISM: Caenorhabditis elegans

<400> SEQUENCE: 27

Met Arg Gln Asp Arg Arg Ser Leu Leu Glu Arg Asn Ile Met Met Phe
 1               5                  10                  15

Ser Ser His Leu Lys Val Asp Glu Ile Leu Glu Val Leu Ile Ala Lys
             20                  25                  30

Gln Val Leu Asn Ser Asp Asn Gly Asp Met Ile Asn Ser Cys Gly Thr
         35                  40                  45

Val Arg Glu Lys Arg Arg Glu Ile Val Lys Ala Val Gln Arg Arg Gly
     50                  55                  60

Asp Val Ala Phe Asp Ala Phe Tyr Asp Ala Leu Arg Ser Thr Gly His
 65                  70                  75                  80

Glu Gly Leu Ala Glu Val Leu Glu Pro Leu Ala
                 85                  90

<210> SEQ ID NO 28
<211> LENGTH: 95
<212> TYPE: PRT
<213> ORGANISM: Homo sapiens

<400> SEQUENCE: 28

Met Glu Ala Arg Asp Lys Gln Val Leu Arg Ser Leu Arg Leu Glu Leu
 1               5                  10                  15

Gly Ala Glu Val Leu Val Glu Gly Leu Val Leu Gln Tyr Leu Gln Tyr
             20                  25                  30

Gln Glu Gly Ile Leu Thr Glu Asn His Ile Gln Glu Ile Asn Ala Gln
         35                  40                  45

Thr Thr Gly Leu Arg Lys Thr Met Leu Leu Leu Asp Ile Leu Pro Ser
     50                  55                  60
```

```
Arg Gly Pro Lys Ala Phe Asp Ile Phe Leu Asp Ser Leu Gln Glu Phe
 65                  70                  75                  80

Pro Trp Val Arg Glu Lys Leu Lys Lys Ala Arg Glu Glu Ala Met
                 85                  90                  95

<210> SEQ ID NO 29
<211> LENGTH: 91
<212> TYPE: PRT
<213> ORGANISM: Homo sapiens

<400> SEQUENCE: 29

Met His Pro His His Gln Glu Thr Leu Lys Lys Asn Arg Val Val Leu
  1               5                  10                  15

Ala Lys Gln Leu Leu Leu Ser Glu Leu Leu Glu His Leu Leu Glu Lys
                 20                  25                  30

Gln Ile Ile Thr Leu Glu Met Arg Glu Leu Ile Gln Ala Lys Val Gly
             35                  40                  45

Ser Phe Ser Gln Asn Val Glu Leu Leu Asn Leu Leu Pro Lys Arg Gly
         50                  55                  60

Pro Gln Ala Phe Asp Ala Phe Cys Glu Ala Leu Arg Glu Thr Lys Gln
 65                  70                  75                  80

Gly His Leu Arg Asp Met Leu Leu Thr Thr Leu
                 85                  90

<210> SEQ ID NO 30
<211> LENGTH: 93
<212> TYPE: PRT
<213> ORGANISM: Homo sapiens

<400> SEQUENCE: 30

Met Asp Glu Ala Asp Arg Arg Leu Leu Arg Arg Cys Arg Leu Arg Leu
  1               5                  10                  15

Val Glu Glu Leu Gln Val Gln Gln Leu Trp Asp Val Leu Leu Ser Arg
                 20                  25                  30

Glu Leu Phe Arg Pro His Met Ile Glu Asp Ile Gln Arg Ala Gly Ser
             35                  40                  45

Gly Ser Arg Arg Asp Gln Ala Arg Gln Leu Asp Ile Asp Leu Glu Thr
         50                  55                  60

Arg Gly Ser Gln Ala Leu Pro Leu Phe Ile Ser Cys Leu Glu Asp Thr
 65                  70                  75                  80

Gly Gln Asp Met Leu Ala Ser Phe Leu Arg Thr Asn Arg
                 85                  90
```

CARD PROTEINS INVOLVED IN CELL DEATH REGULATION

BACKGROUND OF THE INVENTION

1. Field of the Invention

This invention relates generally to the fields of molecular biology and molecular medicine and more specifically to the identification of proteins involved in programmed cell death and associations of these proteins.

2. Background Information

Programmed cell death is a physiologic process that ensures homeostasis is maintained between cell production and cell turnover in essentially all self-renewing tissues. In many cases, characteristic morphological changes, termed "apoptosis," occur in a dying cell. Since similar changes occur in different types of dying cells, cell death appears to proceed through a common pathway in different cell types.

In addition to maintaining tissue homeostasis, apoptosis also occurs in response to a variety of external stimuli, including growth factor deprivation, alterations in calcium levels, free-radicals, cytotoxic lymphokines, infection by some viruses, radiation and most chemotherapeutic agents. Thus, apoptosis is an inducible event that likely is subject to similar mechanisms of regulation as occur, for example, in a metabolic pathway. In this regard, dysregulation of apoptosis also can occur and is observed, for example, in some types of cancer cells, which survive for a longer time than corresponding normal cells, and in neurodegenerative diseases where neurons die prematurely. In viral infections, induction of apoptosis can figure prominently in the pathophysiology of the disease process, because immune-based eradication of viral infections depends on elimination of virus-producing host cells by immune cell attack resulting in apoptosis.

Some of the proteins involved in programmed cell death have been identified and associations among some of these proteins have been described. However, additional apoptosis regulating proteins remain to be found and the mechanisms by which these proteins mediate their activity remains to be elucidated. The identification of the proteins involved in cell death and an understanding of the associations between these proteins can provide a means for manipulating the process of apoptosis in a cell and, therefore, selectively regulating the relative lifespan of a cell or its relative resistance to cell death stimuli.

The principal effectors of apoptosis are a family of intracellular proteases known as Caspases, representing an abbreviation for Cysteine Aspartyl Proteases. Caspases are found as inactive zymogens in essentially all animal cells. During apoptosis, the caspases are activated by proteolytic processing at specific aspartic acid residues, resulting in the production of subunits that assemble into an active protease typically consisting of a heterotetramer containing two large and two small subunits (Thornberry and Lazebnik, *Science* 281:1312–1316 (1998)). The phenomenon of apoptosis is produced directly or indirectly by the activation of caspases in cells, resulting in the proteolytic cleavage of specific substrate proteins. Moreover, in many cases, caspases can cleave and activate themselves and each other, creating cascades of protease activation and mechanisms for "auto"-activation.

Among the substrates of caspases are the intracellular proforms of cytokines such as pro-Interleukin-1β (pro-IL-1β) and pro-IL-18. When cleaved by caspases, these pro- proteins are converted to the biologically active cytokines which are then liberated from cells, circulating in the body and eliciting inflammatory immune reactions. Thus, caspases can be involved, in some instances, in cytokine activation and responses to infectious agents, as well as inflammatory and autoimmune diseases. Caspases also participate in signal transduction pathways activated by some cytokine receptors, particularly members of the Tumor Necrosis Factor (TNF) family of cytokine receptors which are capable of activating certain caspase zymogens.

Thus, knowledge about the proteins having domains that interact with and regulate caspases is important for devising strategies for manipulating cell life and death in therapeutically useful ways. The identification of such proteins that contain caspase-interacting domains and the elucidation of the proteins with which they interact, therefore, can form the basis for strategies designed to modulate apoptosis, cytokine production, cytokine receptor signaling, and other cellular processes. Thus a need exists to identify proteins that interact with caspases and other apoptosis related proteins. The present invention satisfies this need and provides additional advantages as well.

SUMMARY OF THE INVENTION

In accordance with the present invention, there are provided novel "NB-ARC and CARD"-containing proteins, designated NAC, as well as several isoforms of NAC produced by alternative mRNA splicing. The invention also provides nucleic acid molecules encoding NAC and its isoforms, vectors containing these nucleic acid molecules and host cells containing the vectors. The invention also provides antibodies that can specifically bind to NAC proteins, including alternative isoforms thereof.

The present invention also provides a screening assay useful for identifying agents that can effectively alter the association of NAC with itself or with other proteins. By altering the self-association of NAC or by altering their interactions with other proteins, an effective agent may increase or decrease the level of caspase proteolytic activity or apoptosis in a cell, or it may increase or decrease the levels of NF-κB, cytokine production, or other events.

The invention also provides methods of altering the activity of NAC in a cell, wherein such increased or decreased activity of NAC can modulate the level of apoptosis or other cellular responses. For example, the activity of NAC in a cell can be increased by introducing into the cell and expressing a nucleic acid sequence encoding these proteins. In addition, the activity of NAC in a cell can be decreased by introducing into the cell and expressing a fragment of NAC, or an antisense nucleotide sequence that is complementary to a portion of a nucleic acid molecule encoding the NAC proteins.

The invention also provides methods for using an agent that can specifically bind NAC or a nucleotide sequence that can bind to a nucleic acid molecule encoding NAC to diagnose a pathology that is characterized by an altered level of apoptosis due to an increased or decreased level of NAC in a cell.

BRIEF DESCRIPTION OF THE FIGURES

FIG. 1C shows the cDNA and amino acid sequence of the longest NAC isoform (also set for in SEQ ID NOs:1 and 2). The nucleotide sequences of the two alternatively spliced exons (nucleotides 2870–2959, and 3784–3915, respectively, and amino acids 957–987 and 1262–1305) are underlined. The positions for the P-loop (Walker A) and Walker B of NB-ARC domain are indicated. The LRR repeats are in bold letters (amino acids 808–948), and the CARD domain is in bold underlined letters (amino acids 1373–1473).

FIG. 1D shows a sequence analysis of NAC: NB-ARC homology. Alignment of the NB-ARC domains of human NAC (amino acids 329–547), CARD4 (amino acids 197–408), and Apaf-1 (amino acids 138–352), and *Caenorhabditis elegans* CED4 (amino acids 154–374) SEQ ID NOs: 19–22 respectively. Alignment was conducted using Clustal method (Thompson et al., *Nuc. Acids Res.* 22:4673–4680 (1994)). Identical and similar residues are shown in black and gray, respectively.

FIG. 1E shows alignment of CARD domain of NAC and other CARD-containing proteins SEQ ID NOs: 23–30 respectively. Alignment was conducted using Clustal method. Identical and similar residues are shown in black and gray, respectively.

FIG. 3 shows homophilic interactions of CARD domains detected by yeast two-hybrid method. Yeast cells were co-transformed with plasmids encoding the indicated proteins fused to LexA DNA binding domain (LexA) and proteins fused to B42 transactivation domain (B42). Transformants were replica-plated on leucine-supplemented plates (Leu+) and leucine-deficient plates (Leu−) to assess protein interactions. β-galactosidase activity (LacZ) was measured for each transformant, and were scaled as: absent (−), weak (+/−), detectable (+), strong (++), very strong (+++), and strongest (++++)

FIGS. 5(A+B) shows that NAC forms complexes with Apaf-1 and CED4. (A) Complex formation with human Apaf-1. 293T cells were transiently transfected with an expression plasmid encoding HA-tagged human Apaf-1 lacking the C-terminal WD repeats [HA-Apaf-1 (ΔWD)] in the presence (lanes 2 and 3) or absence (lane 1) of a plasmid encoding myc-tagged full-length NAC (myc-NAC). Transfected cells were lysed and subjected to immunoprecipitation (IP) with either a mouse monoclonal antibody to myc (lanes 1 and 3) or a control mouse IgG (lane 2). Proteins from the immune complexes were resolved by SDS-PAGE, transferred to nitrocellulose, and subjected to immunoblot analysis (WB) using anti-HA antibodies (bottom panel) followed by anti-myc antibodies (top panel). One tenth of the total cell lysates derived from each transfection were loaded directly in the gel as a control (Lysate). (B) Complex formation with *C. elegans* CED4 protein. Identical procedures and conditions described for Apaf-1 in (A) were employed for CED4 interaction studies with NAC.

DETAILED DESCRIPTION OF THE INVENTION

Figure 1A:
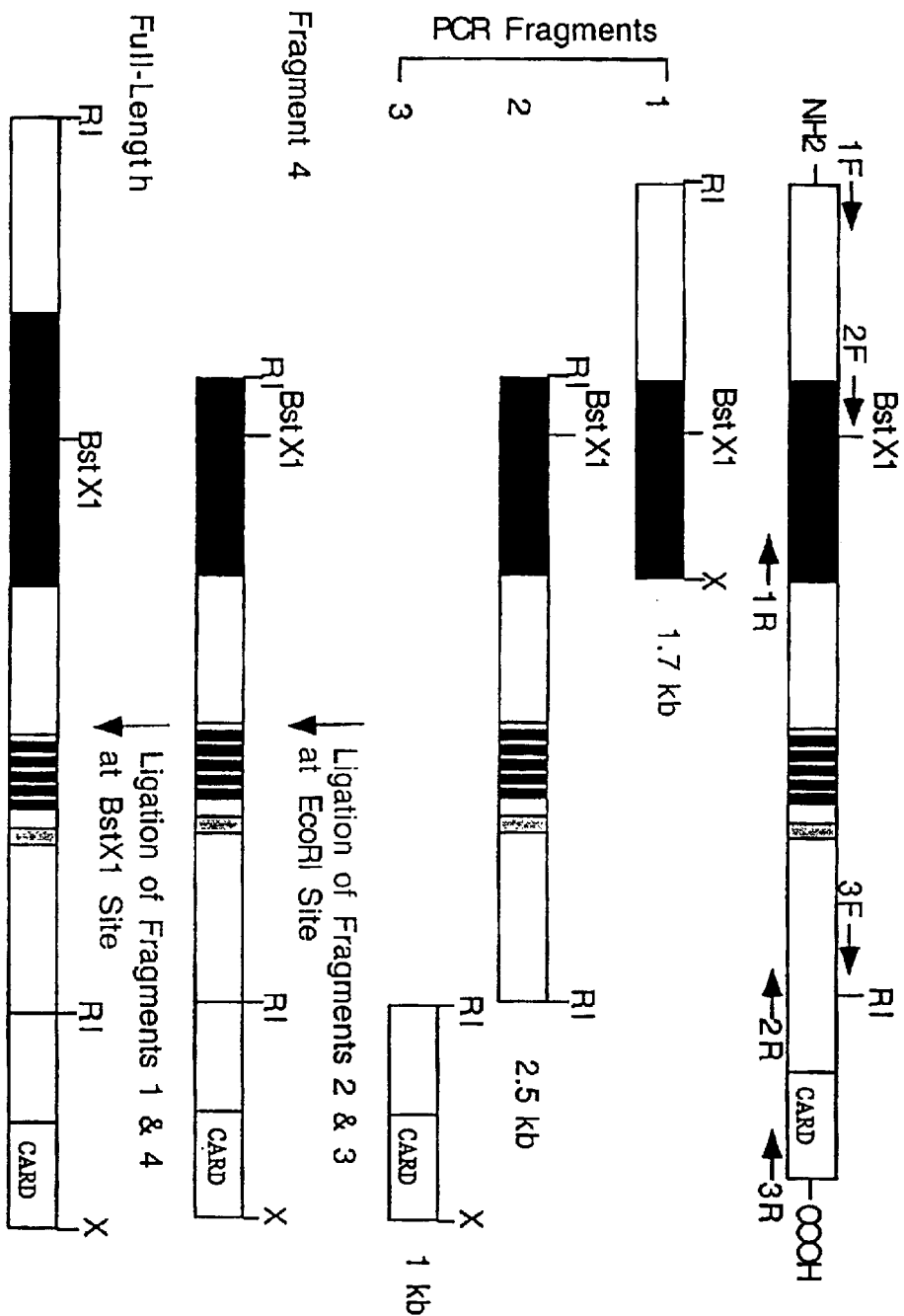
FIG. 1A shows the cloning strategy for NAC and Isoforms of NAC. The NB-ARC domain (filled box), leucine-rich repeats (LRR, filled bars), and the CARD domain (labeled box) are depicted. Relevant restriction sites (RI for EcoRI, X for Xho I) are indicated. Positions for forward PCR primers (1F, 2F, and 3F) and reverse primers (1R, 2R, and 3R) which were used for Reverse Transcriptase-Polymerase Chain Reaction cloning of NAC and NAC-isoforms are shown.

In accordance with the present invention, there are provided "substantially pure" mammalian CARD-containing proteins, designated NAC and CARD-X. As used herein, the term "NAC" refers to a protein that contains both an NB-ARC domain and a CARD domain (NAC). The invention NAC proteins represent novel members of the "CARD domain" family of proteins, which family includes CED-4 and Apaf-1. An invention NAC comprises a NB-ARC domain and a CARD domain, and optionally further comprises a leucine-rich repeat domain and/or a TIM-Barrel-like domain.

As used herein, the term "CARD domain" refers to a Caspase Recruitment Domain (Hofmann et al., *Trends Biochem. Sci.* 22:155–156 (1997)). CARD domains have been found in some members of the Caspase family of cell death proteases. Caspases-1, 2, 4, 5, 9, and 11 contain CARD domains near their $NH_2$-termini. These CARD domains mediate interactions of the zymogen inactive forms of caspases with other proteins which can either activate or inhibit the activation of these enzymes. For example, the CARD domain of pro-caspase-9 binds to the CARD domain of a caspase-activating protein called Apaf-1 (Apoptosis Protease Activating Factor-1). Similarly, the CARD domain of pro-caspase-1 permits interactions with another CARD protein known as Cardiac (also referred to as RIP2 and RICK), which results in activation of the caspase-1 protease (Thome et al., *Curr. Biol.* 16:885–888 (1998)). And, pro-caspase-2 binds to the CARD protein Raidd (also know as Cradd), which permits recruitment of pro-caspase-2 to Tumor Necrosis Factor (TNF) Receptor complexes and which results in activation of the caspase-2 protease (Ahmad et al., *Cancer Res.* 57:615–619 (1997)). CARD domains can also participate in homotypic interactions with themselves, resulting in self-association of proteins that contain these protein-interaction domains and producing dimeric or possibly even oligomeric complexes.

CARD domains can be found in association with other types of functional domains within a single polypeptide, thus providing a mechanism for bringing a functional domain into close proximity or contact with a target protein via CARD:CARD associations involving two CARD-containing proteins. For example, the *Caenorhabiditis elegans* cell death gene ced-4 encodes a protein that contains a CARD domain and a ATP-binding oligomerization domain called an NB-ARC domain (van der Biezen and Jones *Curr Biol* 8:R226–R227). The CARD domain of the CED-4 protein interacts with the CARD domain of a pro-caspase called CED-3. The NB-ARC domain allows CED-4 to self-associate, thereby forming an oligomeric complex which brings associated pro-CED-3 molecules into close proximity to each other. Because most pro-caspases possess at least a small amount of protease activity even in their unprocessed form, the assembly of a complex that brings the proforms of caspase into juxtaposition can result in trans-processing of zymogens, producing the proteolytically processed and active caspase. Thus, CED-4 employs a CARD domain for binding a pro-caspase and an NB-ARC domain for self-oligomerization, resulting in caspase clustering, proteolytic processing and activation.

Numerous CED-4-related proteins have recently been identified. These proteins belong to the CED-4 family of proteins, and include CED-4 (Yuan and Horvitz, *Development* 116:309–320 (1992)), Apaf-1, (Zou et al., *Cell* 90:405–413 (1997)), Dark (Rodriguez et al., Nature Cell Biol. 1:272–279 (1999)), and CARD4/Nod1 (Bertin et al., *J. Biol. Chem.* 274:12955–12958 (1999) and Inohara et al., *J. Biol. Chem.* 274:14560–14567 (1999)). As used herein, a CED-4 family member is a protein that comprises a NB-ARC domain and a CARD domain.

The CED-4 homolog in humans and rodents, referred to as Apaf-1, has been found to function similarly. The Apaf-1 protein contains a (i) CARD domain, (ii) NB-ARC domain, and (iii) multiple copies of a WD-repeat domain. In contrast to CED-4 which can spontaneously oligomerize, the mammalian Apaf-1 protein is an inactive monomer until induced to oligomerize by binding of a co-factor protein, cytochrome c (Li et al., *Cell* 91:479–489 (1997)). In Apaf-1, the WD repeat domains prevent oligomerization of the Apaf-1 protein, until coming into contact with cytochrome c. Thus, the WD-repeats function as a negative-regulatory domain that maintains Apaf-1 in a latent state until cytochrome c release from damaged mitochondria triggers the assembly of an oligomeric Apaf-1 complex (Saleh, *J. Biol. Chem.* 274:17941–17945 (1999)). By binding pro-caspase-9 through its CARD domain, Apaf-1 oligomeric complexes are thought to bring the zymogen forms of caspase-9 into close proximity, permitting them to cleave each other and produce the proteolytic processed and active caspase-9 protease (Zou et al., *J. Biol. Chem.* 274:11549–11556 (1999)).

In addition to their role in caspase-activation, CARD domains have been implicated in other cellular processes. Some CARD-containing proteins, for example, induce activation of the transcription factor NF-κB. NF-κB activation is induced by many cytokines and plays an important role in cytokine receptor signal transduction mechanisms (DiDonato et al., *Nature* 388:548–554 (1997)). Moreover, CARD domains are found in some proteins that inhibit rather than activate caspases, such as the IAP (Inhibitor of Apoptosis Protein) family members, cIAP1 and cIAP2 (Rothe et al., *Cell* 83:1243–1252 (1995)) and oncogenic mutants of the Bcl-10 protein (Willis et al., *Cell* 96:35–45 (1999)). Also, though caspase activation resulting from CARD domain interactions is often involved in inducing apoptosis, other caspases are primarily involved in proteolytic processing and activation of inflammatory cytokines (such as pro-IL-1β and pro-IL-18). Thus, CARD-containing proteins can also be involved in cytokine production, thus regulating immune and inflammatory responses.

In view of the function of the CARD domain within invention NAC proteins, invention NAC proteins or CARD-domain containing fragments thereof, are contemplated herein for use in methods to modulate apoptosis, cytokine production, cytokine receptor signaling, and other cellular processes. Invention NAC proteins or CARD-domain containing fragments thereof are also contemplated in methods to identify CARD-binding agents that modulate apoptosis, cytokine production, cytokine receptor signaling, and other cellular processes.

In one embodiment, a CARD domain of an invention NAC comprises a sequence with at least 50% identity to the CARD domain of NAC (see, e.g., residues 1373–1473 of SEQ ID NO:2). More preferably, a CARD domain of the invention comprises a sequence with at least 60% identity to the CARD domain of NAC. Most preferably, a CARD domain of the invention comprises a sequence with at least 75% identity to the CARD domain of NAC. Typically, a CARD domain of the invention comprises a sequence with at least 95% identity to the CARD domain of NAC.

As described herein, invention NAC or CARD-X proteins can associate with other CARD-containing proteins. In particular, the association of the CARD domain of invention NAC proteins with another CARD-containing protein, such as Apaf-1, CED-4, caspases-1, 2, 9, 11, cIAPs-1 and 2, CARDIAK, Raidd, Dark, CARD4, and other NAC or CARD-X, and the like, is sufficiently specific such that the bound complex can form in vivo in a cell or in vitro under suitable conditions. Similarly therefore, an invention NAC protein can associate with another NAC protein by CARD:CARD association.

A NAC protein of the invention further can associate with pro-caspases, caspases or with caspase-associated proteins, thereby modulating caspase proteolytic activity. Caspase proteolytic activity is associated with apoptosis of cells, and additionally with cytokine production. Therefore, an invention NAC can modulate apoptosis or cytokine production by modulating caspase proteolytic activity. As used herein a "caspase" is any member of the cysteine aspartyl proteases that associates with a NAC protein of the invention or with a NAC associated protein. Similarly, a "pro-caspase" is an inactive or less-active precursor form of a caspase, which is typically converted to the more active caspase form by a proteolytic event.

CARD-containing proteins are also known to induce activation of the transcription factor NF-κB. Thus, an invention NAC can also modulate transcription by modulation of NF-κB activity.

A NAC protein of the invention also comprises a NB-ARC domain. As described herein, a NB-ARC domain of the invention NAC protein comprises a sequence wherein the identity of residues in either the P-Loop (Walker A) or Walker B regions is at least 60% relative to the residues of NAC (see, e.g., residues 329–343 and 407–412 of SEQ ID NO:2; see FIG. 1C). Preferably, an NB-ARC domain of the invention NAC comprises a sequence wherein the overall identity of residues in the P-Loop (Walker A) and Walker B regions is at least 60% relative to the residues of NAC. More preferably, an NB-ARC domain of the invention comprises a sequence with at least 60% identity to the entire NB-ARC domain of NAC (see, e.g., residues 329–547 of SEQ ID NO:2). Most preferably, an NB-ARC domain of the invention comprises a sequence with at least 80% identity to the entire NB-ARC domain of NAC.

The NB-ARC domain of the invention NAC proteins associates with other proteins, particularly with proteins comprising NB-ARC domains. Thus, a functional NB-ARC domain associates with NB-ARC domain-containing proteins by way of NB-ARC:NB-ARC association. As used herein, the term "associate" or "association" means that NAC can bind to a protein relatively specifically and, therefore, can form a bound complex. In particular, the association of the NB-ARC domain of NAC with another NB-ARC domain-containing proteins is sufficiently specific such that the bound complex can form in vivo in a cell or in vitro under suitable condition. Further, a NB-ARC domain demonstrates both nucleotide-binding (e.g., ATP-binding) and hydrolysis activities, which is typically required for its ability to associate with NB-ARC domain-containing proteins. Thus, an NB-ARC domain of the invention NAC comprises one or more nucleotide binding sites. As used herein, a nucleotide binding site is a portion of a protein that specifically binds a nucleotide such as, e.g., ATP, and the like. Typically, the nucleotide binding site of NB-ARC will comprise a P-loop, a kinase 2 motif, or a kinase 3a motif of the invention NAC (these motifs are defined, for example, in van der Biezen and Jones, supra). Preferably, the nucleotide binding site of NB-ARC comprises a P-loop of the invention NAC.

An invention NAC, therefore, is capable of CARD:CARD association and/or NB-ARC:NB-ARC association, resulting in a multifunctional protein capable of one or more specific associations with other proteins. An invention NAC can modulate cell processes such as apoptosis, cytokine production, and the like. For example, it is contemplated herein that an invention NAC protein can increase the level of apoptosis in a cell. It is also contemplated herein that an invention NAC can decrease the level of apoptosis in a cell. For example, a NAC which does not induce apoptosis may form hetero-oligomers with a NAC which is apoptotic, thus interfering with the apoptosis-inducing activity of NAC.

In another embodiment of the invention the NAC protein of the invention also contains Leucine-Rich Repeats (LRR) domain, similar to a LRR described in another CARD protein known as CARD4 (also known as Nod1) (Inohara et al., *J. Biol. Chem.* 274:14560–14567 (1999)). Unlike CARD-4 (Nod1), however, the CARD domain of NAC is located at the Carboxyl end of the protein whereas the CARD domain of CARD-4 (Nod1) is found at the $NH_2$-end of the protein. The function of the LRR domain is to mediate specific interactions with other proteins.

As used herein, leucine-rich repeat (LRR) domain of the invention NAC comprises a sequence with at least 50% identity to the LRR domain of NAC (see, e.g., residues 808–948 of SEQ ID NO:2). Preferably, a LRR domain of the invention NAC comprises a sequence with at least 60% identity to the LRR domain of NAC. More preferably, a LRR region of the invention NAC comprises a sequence with at least 75% identity to the LRR domain of NAC. Most preferably, a LRR region of the invention NAC comprises a sequence with at least 95% identity to the LRR domain of NAC.

It is further contemplated herein that a shortened LRR of the invention NAC may be used. A shortened LRR of the invention comprises a sequence with at least 90% identity to the splice variant form of the LRR (see, e.g., residues 808–917 of SEQ ID NO:2), and does not contain more than 90% of the residues in the splice region (see, e.g., residues 918–947 of SEQ ID NO:2). Preferably, the shortened LRR does not contain more than 70% of the residues in the splice region. More preferably, the shortened LRR does not contain more than 50% of the residues in the splice region. The shortened LRR will be of particular utility when the protein:protein interaction activity of a NAC comprising a shortened LRR differs from that observed for a NAC comprising the full-length LRR. Activity of a NAC with a shortened LRR will be determined by one or more of the assays disclosed herein, and shall be considered to differ from that of a NAC comprising the full-length LRR if any protein:protein interactions are altered by 10% or more, or if caspase activity or apoptotic activity is altered by 10% or more.

In a further embodiment of the invention, invention NAC proteins contain a TIM-Barrel-like domain with similarity to TIM-barrel proteins. TIM-Barrel domains are well known in the art and typically consist of eight alternating α-helices and β-strands forming a barrel-like structure, but may contain 7 α-helices and/or β-strands in some instances. TIM-barrels have been found in some enzymes, such as aldolase, but also mediate protein interactions in some instances.

As used herein, a TIM-Barrel-like domain of an invention NAC comprises a sequence with at least 50% identity to the TIM-Barrel-like domain of NAC (residues 1079–1320 of SEQ ID NO:2). Preferably, a TIM-barrel-like domain of the invention NAC comprises a sequence with at least 60% identity to the TIM-Barrel-like domain of NAC. More preferably, a TIM-barrel domain of the invention NAC comprises a sequence with at least 70% identity to the TIM-barrel-like domain of NAC. Most preferably, a TIM-barrel-like domain of the invention NAC comprises a sequence with at least 80% identity to the TIM-barrel-like domain of NAC.

Presently preferred NAC proteins of the invention include proteins that comprise substantially the same amino acid sequences as the protein sequence set forth in SEQ ID NOs:2, 4, and 6, as well as biologically active, functional fragments thereof.

Those of skill in the art will recognize that numerous residues of the above-described sequences can be substituted with other, chemically, sterically and/or electronically similar residues without substantially altering the biological activity of the resulting NAC protein species. In addition, larger polypeptide sequences containing substantially the same sequence as amino acids set forth in SEQ ID NOs:2, 4, and 6, therein are contemplated.

As employed herein, the term "substantially the same amino acid sequence" refers to amino acid sequences having at least about 70% identity with respect to the reference amino acid sequence, and retaining comparable functional and biological activity characteristic of the protein defined by the reference amino acid sequence. Preferably, proteins having "substantially the same amino acid sequence" will have at least about 80%, more preferably 90% amino acid identity with respect to the reference amino acid sequence; with greater than about 95% amino acid sequence identity being especially preferred. It is recognized, however, that polypeptides (or nucleic acids referred to hereinbefore) containing less than the described levels of sequence identity arising as splice variants or that are modified by conservative amino acid substitutions, or by substitution of degenerate codons are also encompassed within the scope of the present invention.

The term "biologically active" or "functional", when used herein as a modifier of invention NACs, or polypeptide fragments thereof, refers to a polypeptide that exhibits functional characteristics similar to a NAC. Biological activities of NAC are, for example, the ability to bind, preferably in vivo, to a CARD-containing protein or a NB-ARC-containing protein, or to homo-oligomerize, or to modulate protease activation, particularly caspase activation, or to modulate NF-κB activity, or to modulate apoptosis, as described herein. Such NAC binding activity can be assayed, for example, using the methods described herein. Another biological activity of NAC is the ability to act as an immunogen for the production of polyclonal and monoclonal antibodies that bind specifically to an invention NAC. Thus, an invention nucleic acid encoding NAC will encode a polypeptide specifically recognized by an antibody that also specifically recognizes a NAC protein (preferably human) including the amino acid set forth in SEQ ID NOs:2, 4, 6, 10 or 12. Such immunologic activity may be assayed by any method known to those of skill in the art. For example, a test-polypeptide encoded by a NAC cDNA can be used to produce antibodies, which are then assayed for their ability to bind to an invention NAC protein including the sequence set forth in SEQ ID NOs:2, 4, 6, 10 or 12. If the antibody binds to the test-polypeptide and the protein including the sequence encoded by SEQ ID NOs:2, 4, 6, 10 or 12 with substantially the same affinity, then the polypeptide possesses the requisite immunologic biological activity.

As used herein, the term "substantially purified" means a protein that is in a form that is relatively free from contaminating lipids, proteins, nucleic acids or other cellular material normally associated with a protein in a cell. A substantially purified NAC can be obtained by a variety of methods well-known in the art, e.g., recombinant expression systems described herein, precipitation, gel filtration, ion-exchange, reverse-phase and affinity chromatography, and the like. Other well-known methods are described in Deutscher et al., *Guide to Protein Purification: Methods in Enzymology Vol. 182*, (Academic Press, (1990)), which is incorporated herein by reference. Alternatively, the isolated polypeptides of the present invention can be obtained using well-known recombinant methods as described, for example, in Sambrook et al., supra., (1989).

In addition to the ability of invention NAC proteins, or fragments thereof, to interact with other, heterologous proteins (i.e., NB-ARC and CARD-containing proteins), invention NAC and CARD-X proteins have the ability to self-associate. This self-association is possible through interactions between CARD domains, and also through interactions between NB-ARC domains. Further, self-association can take place as a result of interactions between LRR and TIM-Barrel-like domains.

In accordance with the invention, there are also provided mutations and fragments of NAC which have activity different than a wild type NAC activity. As used herein, a "mutation" can be any deletion, insertion, or change of one or more amino acids in the wild type protein sequence, and a "fragment" is any truncated form, either carboxy-terminal, amino-terminal, or both, of the wild type protein. Preferably, the different activity of the mutation or fragment is a result of the mutant protein or fragment maintaining some but not all of the activities of wild type NAC. For example, a fragment of NAC can contain a CARD domain and LRR and TIM-Barrel-like domains, but lack a functional NB-ARC domain. Such a fragment will maintain a portion of the wild type NAC activity (e.g., CARD domain functionality), but not all wild type activities (e.g., lacking an active NB-ARC domain). The resultant fragment will therefore have activity different than wild type NAC activity. In one embodiment, the activity of the fragment will be "dominant negative." A dominant negative activity will allow the fragment to reduce or inactivate the activity of one or more isoforms of wild type NAC.

Isoforms of the NAC proteins are also provided which arise from alternative mRNA splicing and may alter or modify the interactions of the NAC protein with other proteins. For example, three novel isoforms of NAC are provided herein and designated: NACβ, NACγ and NACδ (set forth as SEQ ID Nos:1, 3 and 5, respectively). The amino acid sequence and the portion of cDNA encoding the amino acid sequence of NACβ is shown in FIG. 1C, and the NACβ cDNA and amino acid sequences are listed as SEQ ID NOs: 1 and 2, respectively. NACβ represents the NAC splice variant in which both splice regions are present in the translated polypeptide, thereby including the nucleic acids 1–4422 of the NAC cDNA sequence and amino acids 1–1473 of the NAC protein sequence of FIG. 1C. NACγ represents the NAC splice variant in which neither splice region is present in the translated polypeptide, thereby including the nucleic acids 1–2869, 2960–3783, and 3916–4422 of the NAC cDNA sequence and amino acids 1–956, 988–1261, and 1306–1473 of the NAC protein sequence of FIG. 1C. The NACγ cDNA and amino acid sequences are listed as SEQ ID NOs:3 and 4, respectively. NACδ represents the NAC splice variant in which only the more carboxy-terminal splice region is present in the translated polypeptide, thereby including the nucleic acids 1–2869, and 2960–4422 of the NAC cDNA sequence and amino acids 1–956, and 988–1473 of the NAC protein sequence of FIG. 1C. The NACδ cDNA and amino acid sequences are listed as SEQ ID NOs:5 and 6, respectively.

In another embodiment of the invention, chimeric proteins are provided comprising NAC, or a functional fragment thereof, fused with another protein or functional fragment thereof. Functional fragments of NAC include, for example, NB-ARC, CARD, LRR and TIM-Barrel-like domains, as defined herein. Proteins with which the NAC or functional fragment thereof are fused will include, for example, glutathione-S-transferase, an antibody, or other proteins or functional fragments thereof which facilitate recovery of the chimera. Further proteins with which the NAC or functional fragment thereof are fused will include, for example, luciferase, green fluorescent protein, an antibody, or other proteins or functional fragments thereof which facilitate identification of the chimera. Still further proteins with which the NAC or functional fragment thereof are fused will include, for example, the LexA DNA binding domain, ricin, α-sarcin, an antibody, or other proteins which have therapeutic properties or other biological activity.

Further invention chimeric proteins contemplated herein are chimeric proteins wherein a domain of the NAC is replaced by a similar such domain from a heterologous protein. For example, the NB-ARC domain of NAC, as described above, can be replaced by the NB-ARC domain of Apaf-1, and the like. Another example of such a chimera is a protein wherein the CARD domain of NAC is replaced by the CARD domain from CED-4, and the like.

The CARD-X protein contains a CARD domain and a region with similarity to TIM-Barrel-like domains, but otherwise is distinct from NAC. The cDNA sequence encoding CARD-X (SEQ ID NO:7) reveals that it arises from a separate gene from NAC. The predicted CARD-X amino acid sequence (SEQ ID NO:8), in particular, does not contain an NB-ARC domain.

A CARD domain of the CARD-X protein comprises a sequence with at least 50% identity to the CARD domain of CARD-X (residues 343–431 of SEQ ID NO:8). More preferably, a CARD domain of the invention comprises a sequence with at least 60% identity to the CARD domain of CARD-X. Most preferably, a CARD domain of the invention comprises a sequence with at least 75% identity to the CARD domain of CARD-X. Typically, a CARD domain of the invention comprises a sequence with at least 95% identity to the CARD domain of CARD-X.

A TIM-Barrel-like domain of CARD-X comprises a sequence with at least 50% identity to the TIM-Barrel domain of CARD-X (residues 56–331 of SEQ ID NO:8). Preferably, a TIM-barrel domain of the invention NAC comprises a sequence with at least 60% identity to the TIM-Barrel domain of CARD-X. More preferably, a TIM-barrel domain of the invention CARD-X comprises a sequence with at least 70% identity to the TIM-barrel domain of CARD-X. Most preferably, a TIM-barrel domain of the CARD-X comprises a sequence with at least 80% identity to the TIM-barrel domain of CARD-X.

In one embodiment, invention chimeric CARD-containing proteins provided herein are designated NAC-X. Nucleic acids that encode NAC-X are also provided herein. Alternative isoforms of the NAC-X proteins and the corresponding nucleic acids that encode the alternative isoforms are also provided. As used herein, the term "NAC-X" refers to chimeric proteins comprising portions of a NAC and portions of CARD-X. For example, one type of NAC-X protein is a NACδ-X, wherein a portion of NACδ, for example, the TIM-Barrel-like domain of NACδ, is replaced by a portion of CARD-X, for example, the TIM-Barrel-like domain of CARD-X. It is within the scope of this invention that a protein comprising portions of a domain common to both NAC and CARD-X, particularly the CARD and TIM-Barrel-like domains, can comprise a chimera of NAC and CARD-X. For example, a NACβ-X protein can have residues 1–1397 from SEQ ID NO:2 immediately followed by residues 364–402 from SEQ ID NO:8, which are in turn immediately followed by residues 1436–1473 from SEQ ID NO:2, thus forming a chimeric CARD domain.

In one embodiment, a NAC-X protein will comprise an NB-ARC domain of NAC, as previously described, and the CARD domain of CARD-X. In another embodiment, a NAC-X protein will comprise the NB-ARC domain and LRR domain of NAC, the CARD domain of CARD-X, and the TIM-Barrel-like domain from either NAC or CARD-X or a chimera from both. In yet another embodiment, NAC-X will comprise the NB-ARC and LRR domains of NAC and the CARD and TIM-Barrel-like domains of CARD-X. For example, invention chimeric proteins can include residues between 1–947 and 1–1078 of NACβ (SEQ ID NO:2) or between 1–918 and 1–1048 of NACγ or NACδ (SEQ ID NOs:4 and 6, respectively) in chimera with residues between 1–431 and 56–431 of CARD-X (SEQ ID NO:8). A particular invention chimera is termed NAC-X1 a protein, and comprises the following sequences: NACβ-X1, residues 1–1078 of NACβ and residues 56–431 of CARD-X, having the resultant amino acid sequence listed in SEQ ID NO:10; NACγ/δ-X1 residues 1–1048 of NACγ or NACδ and residues 56–431 of CARD-X, having the resultant amino acid sequence listed in SEQ ID NO:12. The cDNA encoding NACβ-X1 comprises cDNA residues 1–3234 of NACβ and 166–1293 of CARD-X, having the resultant sequence listed in SEQ ID NO:9; and the cDNA encoding NACγ/δ-X1 proteins comprise cDNA residues 1–3144 of NACγ or NACδ and 166–1293 of CARD-X, having the resultant sequence listed in SEQ ID NO:11.

Another embodiment of the invention provides NAC, or a functional fragment thereof, fused with a moiety to form a conjugate. As used herein, a "moiety" can be a physical, chemical or biological entity which contributes functionality to NAC or a functional fragment thereof. Functionalities contributed by a moiety include therapeutic or other biological activity, or the ability to facilitate identification or recovery of NAC. Therefore, a moiety will include molecules known in the art to be useful for detection of the conjugate by, for example, by fluorescence, magnetic imaging, detection of radioactive emission. A moiety may also be useful for recovery of the conjugate, for example a His tag or other known tags used for protein isolation/purification, or a physical substance such as a bead. A moiety can be a therapeutic compound, for example, a cytotoxic drug which can be useful to effect a biological change in cells to which the conjugate localizes.

An example of the means for preparing the invention polypeptide(s) is to express nucleic acids encoding the NAC in a suitable host cell, such as a bacterial cell, a yeast cell, an amphibian cell (i.e., oocyte), or a mammalian cell, using methods well known in the art, and recovering the expressed polypeptide, again using well-known methods. Invention polypeptides can be isolated directly from cells that have been transformed with expression vectors as described below herein. The invention polypeptide, biologically functional fragments, and functional equivalents thereof can also be produced by chemical synthesis. For example, synthetic polypeptides can be produced using Applied Biosystems, Inc. Model 430A or 431A automatic peptide synthesizer (Foster City, Calif.) employing the chemistry provided by the manufacturer.

Also encompassed by the term NAC are functional fragments or polypeptide analogs thereof. The term "functional fragment" refers to a peptide fragment that is a portion of a full length NAC protein, provided that the portion has one or more biological activities, as defined above, that is characteristic of the corresponding full length NAC. For example, a functional fragment of an invention NAC protein can have one or more of the protein:protein binding activities prevalent in NAC. In addition, the characteristic of a functional fragment of invention NAC proteins to elicit an immune response is useful for obtaining an anti-NAC antibodies. Thus, the invention also provides functional fragments of invention NAC proteins, which can be identified using the binding and routine methods, such as bioassays described herein.

The term "polypeptide analog" includes any polypeptide having an amino acid residue sequence substantially the same as a sequence specifically shown herein in which one or more residues have been conservatively substituted with a functionally similar residue and which displays the ability to functionally mimic an NAC as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The amino acid length of functional fragments or polypeptide analogs of the present invention can range from about 5 amino acids up to the full-length protein sequence of an invention NAC. In certain embodiments, the amino acid lengths include, for example, at least about 10 amino acids, at least about 20, at least about 30, at least about 40, at least about 50, at least about 75, at least about 100, at least about 150, at least about 200, at least about 250 or more amino acids in length up to the full-length NAC protein sequence.

As used herein the phrase "conservative substitution" also includes the use of a chemically derivatized residue in place of a non-derivatized residue, provided that such polypeptide displays the required binding activity. The phrase "chemical derivative" refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions of residues, relative to the sequence of a polypeptide whose sequence is shown herein, so long as the required activity is maintained.

The present invention also provides compositions containing an acceptable carrier and any of an isolated, purified NAC mature protein or functional polypeptide fragments thereof, alone or in combination with each other. These polypeptides or proteins can be recombinantly derived, chemically synthesized or purified from native sources. As used herein, the term "acceptable carrier" encompasses any of the standard pharmaceutical carriers, such as phosphate buffered saline solution, water and emulsions such as an oil/water or water/oil emulsion, and various types of wetting agents. The NAC compositions described herein can be used, for example, in methods described hereinafter.

In accordance with another embodiment of the invention, substantially pure nucleic acid molecules, and functional fragments thereof, are provided, which encode invention NACs. Exemplary invention nucleic acid molecules are those comprising substantially the same nucleotide sequence encoding NACβ (SEQ ID NO: 1), NACγ (SEQ ID NO: 3), and NACβ (SEQ ID NO: 5).

The nucleic acid molecules described herein are useful for producing invention proteins, when such nucleic acids are incorporated into a variety of protein expression systems known to those of skill in the art. In addition, such nucleic acid molecules or fragments thereof can be labeled with a readily detectable substituent and used as hybridization probes for assaying for the presence and/or amount of an invention NAC gene or mRNA transcript in a given sample. The nucleic acid molecules described herein, and fragments thereof, are also useful as primers and/or templates in a PCR reaction for amplifying genes encoding invention proteins described herein.

The term "nucleic acid" (also referred to as polynucleotides) encompasses ribonucleic acid (RNA) or deoxyribonucleic acid (DNA), probes, oligonucleotides, and primers. DNA can be either complementary DNA (cDNA) or genomic DNA, e.g. a gene encoding a NAC. One means of isolating a nucleic acid encoding an NAC polypeptide is to probe a mammalian genomic library with a natural or artificially designed DNA probe using methods well known in the art. DNA probes derived from the NAC gene are particularly useful for this purpose. DNA and cDNA molecules that encode NAC polypeptides can be used to obtain complementary genomic DNA, cDNA or RNA from mammalian (e.g., human, mouse, rat, rabbit, pig, and the like), or other animal sources, or to isolate related cDNA or genomic clones by the screening of cDNA or genomic libraries, by methods described in more detail below. Such nucleic acids may include, but are not limited to, nucleic acids comprising substantially the same nucleotide sequence as set forth in SEQ ID NOs:1 (NACβ), 3 (NACγ), and 5 (NACδ).

Use of the terms "isolated" and/or "purified" and/or "substantially purified" in the present specification and claims as a modifier of DNA, RNA, polypeptides or proteins means that the DNA, RNA, polypeptides or proteins so designated have been produced in such form by the hand of man, and thus are separated from their native in vivo cellular environment, and are substantially free of any other species of nucleic acid or protein. As a result of this human intervention, the recombinant DNAs, RNAs, polypeptides and proteins of the invention are useful in ways described herein that the DNAs, RNAs, polypeptides or proteins as they naturally occur are not.

Invention NAC proteins and nucleic acids encoding such, can be obtained from any species of organism, such as prokaryotes, eukaryotes, plants, fungi, vertebrates, invertebrates, and the like. A particular species can be mammalian, As used herein, "mammalian" refers to a subset of species from which an invention NAC is derived, e.g., human, rat, mouse, rabbit, monkey, baboon, bovine, porcine, ovine, canine, feline, and the like. A preferred NAC herein, is human NAC.

In one embodiment of the present invention, cDNAs encoding the invention NACs disclosed herein comprise substantially the same nucleotide sequence as the coding region set forth in any of SEQ ID NOs.1, 3 and 5. Preferred cDNA molecules encoding the invention proteins comprise the same nucleotide sequence as the coding region set forth in any of SEQ ID NOs:1, 3 and 5.

As employed herein, the term "substantially the same nucleotide sequence" refers to DNA having sufficient identity to the reference polynucleotide, such that it will hybridize to the reference nucleotide under moderately stringent hybridization conditions. In one embodiment, DNA having substantially the same nucleotide sequence as the reference nucleotide sequence encodes substantially the same amino acid sequence as that set forth in any of SEQ ID NOs:2, 4, 6, 10 or 12. In another embodiment, DNA having "substantially the same nucleotide sequence" as the reference nucleotide sequence has at least 60% identity with respect to the reference nucleotide sequence. DNA having at least 70%, more preferably at least 90%, yet more preferably at least 95%, identity to the reference nucleotide sequence is preferred.

This invention also encompasses nucleic acids which differ from the nucleic acids shown in SEQ ID NOs:1, 3 and 5, but which have the same phenotype. Phenotypically similar nucleic acids are also referred to as "functionally equivalent nucleic acids". As used herein, the phrase "functionally equivalent nucleic acids" encompasses nucleic acids characterized by slight and non-consequential sequence variations that will function in substantially the same manner to produce the same protein product(s) as the nucleic acids disclosed herein. In particular, functionally equivalent nucleic acids encode polypeptides that are the same as those encoded by the nucleic acids disclosed herein or that have conservative amino acid variations. For example, conservative variations include substitution of a non-polar residue with another non-polar residue, or substitution of a charged residue with a similarly charged residue. These variations include those recognized by skilled artisans as those that do not substantially alter the tertiary structure of the protein.

Further provided are nucleic acids encoding NAC polypeptides that, by virtue of the degeneracy of the genetic code, do not necessarily hybridize to the invention nucleic acids under specified hybridization conditions. Preferred nucleic acids encoding the invention NACs are comprised of nucleotides that encode substantially the same amino acid sequence as set forth in SEQ ID NOs:2, 4, 6, 10 or 12.

Thus, an exemplary nucleic acid encoding an invention NAC may be selected from:
(a) DNA encoding the amino acid sequence set forth in SEQ ID NOs:2, 4, 6, 10 or 12,
(b) DNA that hybridizes to the DNA of (a) under moderately stringent conditions, wherein said DNA encodes biologically active NAC, or
(c) DNA degenerate with respect to (b) wherein said DNA encodes biologically active NAC.

Hybridization refers to the binding of complementary strands of nucleic acid (i.e., sense:antisense strands or probe:target-DNA) to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature ($T_m$) of the hybrids. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-DNA to bind a complementary nucleic acid that has about 60% identity, preferably about 75% identity, more preferably about 85% identity to the target DNA; with greater than about 90% identity to target-DNA being especially preferred. Preferably, moderately stringent conditions are conditions equivalent to hybridization in 50% formamide, 5× Denhart's solution, 5×SSPE, 0.2% SDS at 42° C., followed by washing in 0.2×SSPE, 0.2% SDS, at 65° C.

The phrase "high stringency hybridization" refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5× Denhart's solution, 5×SSPE, 0.2% SDS at 42° C., followed by washing in 0.1×SSPE, and 0.1% SDS at 65° C.

The phrase "low stringency hybridization" refers to conditions equivalent to hybridization in 10% formamide, 5× Denhart's solution, 6×SSPE, 0.2% SDS at 42° C., followed by washing in 1×SSPE, 0.2% SDS, at 50° C. Denhart's solution and SSPE (see, e.g., Sambrook et al., *Molecular Cloning, A Laboratory Manual*, Cold Spring Harbor Laboratory Press, (1989)) are well known to those of skill in the art as are other suitable hybridization buffers.

As used herein, the term "degenerate" refers to codons that differ in at least one nucleotide from a reference nucleic acid, e.g., SEQ ID NOs:1, 3 and 5, but encode the same amino acids as the reference nucleic acid. For example, codons specified by the triplets "UCU", "UCC", "UCA", and "UCG" are degenerate with respect to each other since all four of these codons encode the amino acid serine.

Preferred nucleic acids encoding the invention polypeptide(s) hybridize under moderately stringent, preferably high stringency, conditions to substantially the entire sequence, or substantial portions (i.e., typically at least 15–30 nucleotides) of the nucleic acid sequence set forth in SEQ ID NOs:1, 3 and 5.

The invention nucleic acids can be produced by a variety of methods well-known in the art, e.g., the methods described herein, employing PCR amplification using oligonucleotide primers from various regions of SEQ ID NOs:1, 3 and 5, and the like.

In accordance with a further embodiment of the present invention, optionally labeled NAC-encoding cDNAs, or fragments thereof, can be employed to probe library(ies) (e.g., cDNA, genomic, and the like) for additional nucleic acid sequences encoding novel NACs. Construction of suitable mammalian cDNA libraries, including mammalian cDNA libraries, is well-known in the art. Screening of such a cDNA library is initially carried out under low-stringency conditions, which comprise a temperature of less than about 42° C., a formamide concentration of less than about 50%, and a moderate to low salt concentration.

Presently preferred probe-based screening conditions comprise a temperature of about 37° C., a formamide concentration of about 20%, and a salt concentration of about 5× standard saline citrate (SSC; 20×SSC contains 3M sodium chloride, 0.3M sodium citrate, pH 7.0). Such conditions will allow the identification of sequences which have a substantial degree of similarity with the probe sequence, without requiring perfect homology. The phrase "substantial similarity" refers to sequences which share at least 50% homology. Preferably, hybridization conditions will be selected which allow the identification of sequences having at least 70% homology with the probe, while discriminating against sequences which have a lower degree of homology with the probe. As a result, nucleic acids having substantially the same nucleotide sequence as SEQ ID NOs:1, 3 and 5 are obtained.

As used herein, a nucleic acid "probe" is single-stranded DNA or RNA, or analogs thereof, that has a sequence of nucleotides that includes at least 15, at least 20, at least 50, at least 100, at least 200, at least 300, at least 400, or at least 500 contiguous bases that are the same as (or the complement of) any contiguous bases set forth in any of SEQ ID NOs:1, 3 and 5. Preferred regions from which to construct probes include 5' and/or 3' coding regions of SEQ ID NOs:1, 3 and 5. In addition, the entire cDNA encoding region of an invention NAC, or the entire sequence corresponding to SEQ ID NOs:1, 3 and 5, may be used as a probe. Probes may be labeled by methods well-known in the art, as described hereinafter, and used in various diagnostic kits.

As used herein, the terms "label" and "indicating means" in their various grammatical forms refer to single atoms and molecules that are either directly or indirectly involved in the production of a detectable signal. Any label or indicating means can be linked to invention nucleic acid probes, expressed proteins, polypeptide fragments, or antibody molecules. These atoms or molecules can be used alone or in conjunction with additional reagents. Such labels are themselves well-known in clinical diagnostic chemistry.

The labeling means can be a fluorescent labeling agent that chemically binds to antibodies or antigens without denaturation to form a fluorochrome (dye) that is a useful immunofluorescent tracer. A description of immunofluorescent analytic techniques is found in DeLuca, "Immunofluorescence Analysis", in *Antibody As a Tool*, Marchalonis et al., eds., John Wiley & Sons, Ltd., pp. 189–231 (1982), which is incorporated herein by reference.

In one embodiment, the indicating group is an enzyme, such as horseradish peroxidase (HRP), glucose oxidase, and the like. In another embodiment, radioactive elements are employed labeling agents. The linking of a label to a substrate, i.e., labeling of nucleic acid probes, antibodies, polypeptides, and proteins, is well known in the art. For instance, an invention antibody can be labeled by metabolic incorporation of radiolabeled amino acids provided in the culture medium. See, for example, Galfre et al., *Meth. Enzymol.*, 73:3–46 (1981). Conventional means of protein conjugation or coupling by activated functional groups are particularly applicable. See, for example, Aurameas et al., *Scand. J. Immunol.*, Vol. 8, Suppl. 7:7–23 (1978), Rodwell et al., *Biotech.*, 3:889–894 (1984), and U.S. Pat. No. 4,493,795.

Also provided are antisense-nucleic acids having a sequence capable of binding specifically with full-length or any portion of an mRNA that encodes NAC polypeptides so as to prevent translation of the mRNA. The antisense-nucleic acid may have a sequence capable of binding specifically with any portion of the sequence of the cDNA encoding NAC polypeptides. As used herein, the phrase "binding specifically" encompasses the ability of a nucleic acid sequence to recognize a complementary nucleic acid sequence and to form double-helical segments therewith via the formation of hydrogen bonds between the complementary base pairs. An example of an antisense-nucleic acid is an antisense-nucleic acid comprising chemical analogs of nucleotides.

Compositions comprising an amount of the antisense-nucleic acid, described above, effective to reduce expression of NAC polypeptides by passing through a cell membrane and binding specifically with mRNA encoding NAC polypeptides so as to prevent translation and an acceptable hydrophobic carrier capable of passing through a cell membrane are also provided herein. Suitable hydrophobic carriers are described, for example, in U.S. Pat. Nos. 5,334,761; 4,889,953; 4,897,355, and the like. The acceptable hydrophobic carrier capable of passing through cell membranes may also comprise a structure which binds to a receptor specific for a selected cell type and is thereby taken up by cells of the selected cell type. The structure may be part of a protein known to bind to a cell-type specific receptor.

Antisense-nucleic acid compositions are useful to inhibit translation of mRNA encoding invention polypeptides. Synthetic oligonucleotides, or other antisense chemical structures are designed to bind to mRNA encoding NAC polypeptides and inhibit translation of mRNA and are useful as compositions to inhibit expression of NAC associated genes in a tissue sample or in a subject.

In accordance with another embodiment of the invention, kits are provided for detecting mutations, duplications, deletions, rearrangements and aneuploidies in NAC genes comprising at least one invention probe or antisense nucleotide.

The present invention provides means to modulate levels of expression of NAC polypeptides by employing synthetic antisense-nucleic acid compositions (hereinafter SANC) which inhibit translation of mRNA encoding these polypeptides. Synthetic oligonucleotides, or other antisense-nucleic acid chemical structures designed to recognize and selectively bind to mRNA, are constructed to be complementary to full-length or portions of an NAC coding strand, including nucleotide sequences set forth in SEQ ID NOs:1, 3 and 5. The SANC is designed to be stable in the blood stream for administration to a subject by injection, or in laboratory cell culture conditions. The SANC is designed to be capable of passing through the cell membrane in order to enter the cytoplasm of the cell by virtue of physical and chemical properties of the SANC which render it capable of passing through cell membranes, for example, by designing small, hydrophobic SANC chemical structures, or by virtue of specific transport systems in the cell which recognize and transport the SANC into the cell. In addition, the SANC can be designed for administration only to certain selected cell populations by targeting the SANC to be recognized by specific cellular uptake mechanisms which bind and take up the SANC only within select cell populations. In a particular embodiment the SANC is an antisense oligonucleotide.

For example, the SANC may be designed to bind to a receptor found only in a certain cell type, as discussed supra. The SANC is also designed to recognize and selectively bind to target mRNA sequence, which may correspond to a sequence contained within the sequences shown in SEQ ID NOs:1, 3 and 5. The SANC is designed to inactivate target mRNA sequence by either binding thereto and inducing degradation of the mRNA by, for example, RNase I digestion, or inhibiting translation of mRNA target sequence by interfering with the binding of translation-regulating factors or ribosomes, or inclusion of other chemical structures, such as ribozyme sequences or reactive chemical groups which either degrade or chemically modify the target mRNA. SANCs have been shown to be capable of such properties when directed against mRNA targets (see Cohen et al., *TIPS*, 10:435 (1989) and Weintraub, *Sci. American*, January (1990), pp.40; both incorporated herein by reference).

In accordance with yet another embodiment of the present invention, there is provided a method for the recombinant production of invention NAC by expressing the above-described nucleic acid sequences in suitable host cells. Recombinant DNA expression systems that are suitable to produce NAC described herein are well-known in the art. For example, the above-described nucleotide sequences can be incorporated into vectors for further manipulation. As used herein, vector (or plasmid) refers to discrete elements that are used to introduce heterologous DNA into cells for either expression or replication thereof.

Suitable expression vectors are well-known in the art, and include vectors capable of expressing DNA operatively linked to a regulatory sequence, such as a promoter region that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors are well known to those of skill in the art and include those that are replicable in eukaryotic cells and/or prokaryotic cells and those that remain episomal or those which integrate into the host cell genome.

Prokaryotic transformation vectors are well-known in the art and include pBlueskript and phage Lambda ZAP vectors (Stratagene, La Jolla, Calif.), and the like. Other suitable vectors and promoters are disclosed in detail in U.S. Pat. No. 4,798,885, issued Jan. 17, 1989, the disclosure of which is incorporated herein by reference in its entirety.

Other suitable vectors for transformation of E. coli cells include the pET expression vectors (Novagen, see U.S. Pat. No. 4,952,496), e.g., pET11a, which contains the T7 promoter, T7 terminator, the inducible E. coil lac operator, and the lac repressor gene; and pET 12a-c, which contain the T7 promoter, T7 terminator, and the E. coli ompT secretion signal. Another suitable vector is the pIN-IIIompA2 (see Duffaud et al., Meth. in Enzymology, 153:492–507, 1987), which contains the lpp promoter, the lacUV5 promoter operator, the ompA secretion signal, and the lac repressor gene.

In accordance with another embodiment of the present invention, there are provided "recombinant cells" containing the nucleic acid molecules (i.e., DNA or mRNA) of the present invention. Methods of transforming suitable host cells, preferably bacterial cells, and more preferably E. coli cells, as well as methods applicable for culturing said cells containing a gene encoding a heterologous protein, are generally known in the art. See, for example, Sambrook et al., Molecular Cloning: A Laboratory Manual (2 ed.), Cold Spring Harbor Laboratory Press, Cold Spring Harbor, N.Y., USA (1989).

Exemplary methods of transformation include, e.g., transformation employing plasmids, viral, or bacterial phage vectors, transfection, electroporation, lipofection, and the like. The heterologous DNA can optionally include sequences which allow for its extrachromosomal maintenance, or said heterologous DNA can be caused to integrate into the genome of the host (as an alternative means to ensure stable maintenance in the host).

Host organisms contemplated for use in the practice of the present invention include those organisms in which recombinant production of heterologous proteins has been carried out. Examples of such host organisms include bacteria (e.g., E. coli), yeast (e.g., Saccharomyces cerevisiae, Candida tropicalis, Hansenula polymorpha and P. pastoris; see, e.g., U.S. Pat. Nos. 4,882,279, 4,837,148, 4,929,555 and 4,855,231), mammalian cells (e.g., HEK293, CHO and Ltk⁻ cells), insect cells, and the like. Presently preferred host organisms are bacteria. The most preferred bacteria is E. coli.

In one embodiment, nucleic acids encoding the invention NAC can be delivered into mammalian cells, either in vivo or in vitro using suitable viral vectors well-known in the art. Suitable retroviral vectors, designed specifically for "gene therapy" methods, are described, for example, in WIPO publications WO 9205266 and WO 9214829, which provide a description of methods for efficiently introducing nucleic acids into human cells. In addition, where it is desirable to limit or reduce the in vivo expression of the invention NAC, the introduction of the antisense strand of the invention nucleic acid is contemplated.

For example, in one embodiment of the present invention, adenovirus-transferrin/polylysine-DNA (TfAdpl-DNA) vector complexes (Wagner et al., Proc. Natl. Acad. Sci., USA, 89:6099–6103 (1992); Curiel et al., Hum. Gene Ther., 3:147–154 (1992); Gao et al., Hum. Gene Ther., 4:14–24 (1993)) are employed to transduce mammalian cells with heterologous NAC nucleic acid. Any of the plasmid expression vectors described herein may be employed in a TfAdpl-DNA complex.

In accordance with yet another embodiment of the present invention, there are provided anti-NAC antibodies having specific reactivity with an NAC polypeptides of the present invention. The present invention also provides anti-NACβ, anti-NACγ, anti-NACδ, anti-NACβ-X1, or anti-NACγ/δ-X1 antibodies. It should be recognized that an antibody of the invention can be specific for an epitope that is present only in a particular type of NAC or can be specific for an epitope that is common to more than one type of NAC. For example, an anti-NACδ antibody can be specific for only NACδ or for more than one member of the NAC family. As used herein, the term "antibody" is used in its broadest sense to include polyclonal and monoclonal antibodies, as well as polypeptide fragments of antibodies that retain a specific binding activity for a specific antigen of at least about 1×10⁵ M-1. One skilled in the art would know that, for example, anti-NACβ antibody fragments or anti-NACγ antibody fragments such as Fab, F(ab')2, Fv and Fd fragments can retain specific binding activity for a NACβ or a NACγ, respectively, and, thus, are included within the definition of an antibody. In addition, the term "antibody" as used herein includes naturally occurring antibodies as well as non-naturally occurring antibodies and fragments of antibodies that retain binding activity. Such non-naturally occurring antibodies can be constructed using solid phase peptide synthesis, can be produced recombinantly or can be obtained, for example, by screening combinatorial libraries consisting of variable heavy chains and variable light chains as described by Huse et al., Science 246:1275–1281 (1989), which is incorporated herein by reference.

Invention antibodies can be produced by methods known in the art using invention polypeptides, proteins or portions thereof as antigens. For example, polyclonal and monoclonal antibodies can be produced by methods well known in the art, as described, for example, in Harlow and Lane, Antibodies: A Laboratory Manual (Cold Spring Harbor Laboratory (1988)), which is incorporated herein by reference. Invention polypeptides can be used as immunogens in generating such antibodies. Alternatively, synthetic peptides can be prepared (using commercially available synthesizers) and used as immunogens. Amino acid sequences can be analyzed by methods well known in the art to determine whether they encode hydrophobic or hydrophilic domains of the corresponding polypeptide. Altered antibodies such as chimeric, humanized, CDR-grafted or bifunctional antibodies can also be produced by methods well known in the art. Such antibodies can also be produced by hybridoma, chemical synthesis or recombinant methods described, for example, in Sambrook et al., supra., and Harlow and Lane, supra. Both anti-peptide and anti-fusion protein antibodies can be used. (see, for example, Bahouth et al., Trends Pharmacol. Sci. 12:338 (1991); Ausubel et al., Current Protocols in Molecular Biology (John Wiley and Sons, NY (1989) which are incorporated herein by reference).

In the case of monoclonal antibodies specific to NAC, it is also contemplated herein that the invention includes hybridomas and any other type of cell line which produces a monoclonal antibody. Methods of preparing hybridomas are described for example, in Sambrook et al., supra., and Harlow and Lane, supra; and preparation of any nonhybridoma cell line producing a monoclonal antibody specific to NAC can be carried out in accordance with the methods known in the art and methods described herein for protein expression in cells such as bacterial cells, yeast cells, amphibian cells, mammalian cells, and the like.

Antibody so produced can be used, inter alia, in diagnostic methods and systems to detect the level of NAC present in a mammalian, preferably human, body sample, such as tissue or vascular fluid. Such antibodies can also be used for the immunoaffinity or affinity chromatography purification of the invention NAC. In addition, methods are contemplated herein for detecting the presence of an invention NAC protein in a tissue or cell, comprising contacting the cell with an antibody that specifically binds to NAC polypeptides, under conditions permitting binding of the antibody to the NAC polypeptides, detecting the presence of the antibody bound to the NAC polypeptide, and thereby detecting the presence of invention polypeptides. With respect to the detection of such polypeptides, the antibodies can be used for in vitro diagnostic or in vivo imaging methods.

Immunological procedures useful for in vitro detection of target NAC polypeptides in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionucleotides, enzymes, fluorogens, chromogens and chemiluminescent labels.

Invention anti-NAC antibodies are contemplated for use herein to modulate the activity of the NAC polypeptide in living animals, in humans, or in biological tissues or fluids isolated therefrom. The term "modulate" refers to a compound's ability to increase (e.g., via an agonist) or inhibit (e.g., via an antagonist) the biological activity of an invention NAC protein, such as the capablity of binding CARD-containing proteins, NB-ARC-containing proteins, to modulate the activity of proteases such as caspases, to modulate the activity of NF-κB, and to modulate apoptosis. Accordingly, compositions comprising a carrier and an amount of an antibody having specificity for NAC polypeptides effective to inhibit naturally occurring ligands or NAPs from binding to invention NAC polypeptides are contemplated herein. For example, a monoclonal antibody directed to an epitope of an invention NAC polypeptide including an amino acid sequence set forth in SEQ ID NOs:2, 4, 6, 10 or 12, can be useful for this purpose.

The present invention further provides transgenic non-human mammals that are capable of expressing exogenous nucleic acids encoding NAC polypeptides. As employed herein, the phrase "exogenous nucleic acid" refers to nucleic acid sequence which is not native to the host, or which is present in the host in other than its native environment (e.g., as part of a genetically engineered DNA construct). In addition to naturally occurring levels of NAC, invention NAC can either be overexpressed or underexpressed (such as in the well-known knock-out transgenics) in transgenic mammals.

Also provided are transgenic non-human mammals capable of expressing nucleic acids encoding NAC polypeptides so mutated as to be incapable of normal activity, i.e., do not express native NAC. The present invention also provides transgenic non-human mammals having a genome comprising antisense nucleic acids complementary to nucleic acids encoding NAC polypeptides, placed so as to be transcribed into antisense mRNA complementary to mRNA encoding NAC polypeptides, which hybridizes to the mRNA and, thereby, reduces the translation thereof. The nucleic acid may additionally comprise an inducible promoter and/or tissue specific regulatory elements, so that expression can be induced, or restricted to specific cell types. Examples of nucleic acids are DNA or cDNA having a coding sequence substantially the same as the coding sequence shown in SEQ ID NOs:1, 3 or 5. An example of a non-human transgenic mammal is a transgenic mouse. Examples of tissue specificity-determining elements are the metallothionein promoter and the L7 promoter.

Animal model systems which elucidate the physiological and behavioral roles of NAC polypeptides are also provided, and are produced by creating transgenic animals in which the expression of the NAC polypeptide is altered using a variety of techniques. Examples of such techniques include the insertion of normal or mutant versions of nucleic acids encoding an NAC polypeptide by microinjection, retroviral infection or other means well known to those skilled in the art, into appropriate fertilized embryos to produce a transgenic animal. (See, for example, Hogan et al., *Manipulating the Mouse Embryo: A Laboratory Manual* (Cold Spring Harbor Laboratory, (1986)).

Also contemplated herein, is the use of homologous recombination of mutant or normal versions of NAC genes with the native gene locus in transgenic animals, to alter the regulation of expression or the structure of NAC polypeptides (see, Capecchi et al., *Science* 244:1288 (1989); Zimmer et al., *Nature* 338:150 (1989); which are incorporated herein by reference). Homologous recombination techniques are well known in the art. Homologous recombination replaces the native (endogenous) gene with a recombinant or mutated gene to produce an animal that cannot express native (endogenous) protein but can express, for example, a mutated protein which results in altered expression of NAC polypeptides.

In contrast to homologous recombination, microinjection adds genes to the host genome, without removing host genes. Microinjection can produce a transgenic animal that is capable of expressing both endogenous and exogenous NAC. Inducible promoters can be linked to the coding region of nucleic acids to provide a means to regulate expression of the transgene. Tissue specific regulatory elements can be linked to the coding region to permit tissue-specific expression of the transgene. Transgenic animal model systems are useful for in vivo screening of compounds for identification of specific ligands, i.e., agonists and antagonists, which activate or inhibit NAC protein responses.

A further embodiment of the invention provides a method to identify agents that can effectively alter NAC activity, for example the ability of NAC to association with one or more heterologous proteins. Thus, the present invention provides a screening assay useful for identifying an effective agent, which can alter the association of a NAC with a NAC associated protein, such as a CARD-containing protein and/or an NB-ARC-containing protein. Since CARD-containing proteins and NB-ARC-containing proteins are involved in apoptosis, the identification of such effective agents can be useful for modulating the level of apoptosis in a cell in a subject having a pathology characterized by an increased or decreased level of apoptosis.

Further, since invention NAC proteins comprise CARD domains, effective agents can be useful for modulation of any other CARD domain activity. These additional CARD domain activities include, for example, NF-κB activity modulation, cytokine receptor signal transduction, and caspase activation/inhibition, regardless of whether the effected caspase is involved in apoptosis or some alternative cellular process such as proteolytic processing and activation of inflammatory cytokines.

As used herein, the term "agent" means a chemical or biological molecule such as a simple or complex organic molecule, a peptide, a peptido-mimetic, a protein or an oligonucleotide that has the potential for altering the association of NAC with a heterologous protein or altering the ability of NAC to self-associate or altering the nucleotide binding and/or hydrolysis activity of NAC. In addition, the term "effective agent" is used herein to mean an agent that can, in fact, alter the association of NAC with a heterologous protein or altering the ability of NAC to self-associate or altering the nucleotide binding and/or hydrolysis activity of NAC. For example, an effective agent may be an anti-NAC antibody or a NAC-associated-protein.

As used herein, the term "alter the association" means that the association between two specifically interacting proteins either is increased or is decreased due to the presence of an effective agent. As a result of an altered association of NAC with another protein in a cell, the activity of the NAC or the NAC associated protein can be increased or decreased, thereby modulating a biological process, for example, the level of apoptosis in the cell. As used herein, the term "alter the activity" means that the agent can increase or decrease the activity of a NAC in a cell, thereby modulating a biological process in a cell, for example, the level of apoptosis in the cell. For example, an effective agent can increase or decrease the NB-ARC:NB-ARC-associating activity of a NAC, without affecting the association of the NAC with a CARD-containing protein. Modulation of the ATP hydrolysis activity can modulate the ability of NAC proteins to associate with other NB-ARC-containing proteins, such as Apaf-1, thereby modulating any process effected by such association between NAC and an NB-ARC-containing protein. Similarly, the term "alters the association" of NAC with another protein refers to increasing or decreasing, or otherwise changing the association between a NAC and a protein that specifically binds to NAC (i.e., a NAC associated protein).

An effective agent can act by interfering with the ability of a NAC to associate with another protein, or can act by causing the dissociation of NAC from a complex with a NAC-associated protein, wherein the ratio of bound NAC to free NAC is related to the level of a biological process, for example, apoptosis, in a cell. For example, binding of a ligand to a NAC-associated protein can allow the NAC-associated protein, in turn, to bind a NAC. The association, for example, of a CARD-containing protein and a NAC can result in activation or inhibition of the NB-ARC:NB-ARC-associating activity of NAC. In the presence of an effective agent, the association of a NAC and a CARD-containing protein can be altered, which can thereby alter the activation of caspases in the cell. As a result of the altered caspase activation, the level of apoptosis in a cell can be increased or decreased. Thus, the identification of an effective agent that alters the association of NAC with another protein can allow for the use of the effective agent to increase or decrease the level of apoptosis in a cell.

An effective agent can be useful, for example, to increase the level of apoptosis in a cell such as a cancer cell, which is characterized by having a decreased level of apoptosis as compared to its normal cell counterpart. An effective agent also can be useful, for example, to decrease the level of apoptosis in a cell such as a T lymphocyte in a subject having a viral disease such as acquired immunodeficiency syndrome, which is characterized by an increased level of apoptosis in an infected T cell as compared to a normal T cell. Thus, an effective agent can be useful as a medicament for altering the level of apoptosis in a subject having a pathology characterized by increased or decreased apoptosis. In addition, an effective agent can be used, for example, to decrease the level of apoptosis and, therefore, increase the survival time of a cell such as a hybridoma cell in culture. The use of an effective agent to prolong the survival of a cell in vitro can significantly improve bioproduction yields in industrial tissue culture applications.

A NAC that lacks the ability to bind the NB-ARC domain of another protein but retains the ability to self-associate via its CARD domain or to bind to other CARD-containing proteins is an example of an effective agent, since the expression of a non-NB-ARC-associating NAC in a cell can alter the association of a the endogenous NAC protein with itself or with NAC associated proteins.

Thus, it should be recognized that a mutation of a NAC can be an effective agent, depending, for example, on the normal level of NAC/NAC-associated protein that occurs in a particular cell type. In addition, an active fragment of a NAC can be an effective agent, provided the active fragment can alter the association of NAC and another protein in a cell. Such active fragments, which can be peptides as small as about five amino acids, can be identified, for example, by screening a peptide library (see, for example, Ladner et al., U.S. Pat. No. 5,223,409, which is incorporated herein by reference) to identify peptides that can bind a NAC-associated protein.

Similarly, a peptide or polypeptide portion of a NAC-associated protein also can be an effective agent. A peptide such as the C-terminal peptide of NAC-associated protein can be useful, for example, for decreasing the association of NAC with a CARD-containing protein or a NB-ARC-containing protein in a cell by competing for binding to the NAC. A non-naturally occurring peptido-mimetic also can be useful as an effective agent. Such a peptido-mimetic can include, for example, a peptoid, which is peptide-like sequence containing N-substituted glycines, or an oligocarbamate. A peptido-mimetic can be particularly useful as an effective agent due, for example, to having an increased stability to enzymatic degradation in vivo.

A screening assay to identify an effective agent can be performed in vivo using the two hybrid system or can be performed in vitro as disclosed herein. The yeast two hybrid system, for example, can be used to screen a panel of agents to identify effective agents that alter the association of NAC with another protein. An effective agent can be identified by detecting an altered level of transcription of a reporter gene. For example, the level of transcription of a reporter gene due to the bridging of a DNA-binding domain and trans-activation domain by a NAP and NAC hybrids can be determined in the absence and in the presence of an agent. An effective agent, which alters the association between NAC and another protein, can be identified by a proportionately altered level of transcription of the reporter gene as compared to the control level of transcription in the absence of the agent.

As understood by those of skill in the art, assay methods for identifying agents that modulate NAC activity generally require comparison to a control. For example, one type of a "control" is a cell or culture that is treated substantially the same as the test cell or test culture exposed to the agent, with the distinction that the "control" cell or culture is not exposed to the agent. Another type of "control" cell or culture may be a cell or culture that is identical to the transfected cells, with the exception that the "control" cell or culture do not express native proteins. Accordingly, the response of the transfected cell to agent is compared to the response (or lack thereof) of the "control" cell or culture to the same agent under the same reaction conditions. Similarly, a "control" can be the extract, partially purified or not, of a cell not exposed to the agent or not expressing certain native proteins. A "control" may also be an isolated compound, for example, a protein (e.g., Skp-1 as used in Examples), which is known to not specifically associate with NAC proteins.

Accordingly, in accordance with another embodiment of the present invention, there is provided a method of identifying an effective agent that alters the association of a NB-ARC and CARD-containing protein (NAC) with a NAC associated protein (NAP), by the steps of:

a. contacting said NAC and NAP proteins, under conditions that allow the NAC and NAP proteins to associate, with an agent suspected of being able to alter the association of the NAC and NAP proteins; and b. detecting the altered association of the NAC and NAP proteins, wherein the altered association identifies an effective agent.

Methods well-known in the art for detecting the altered association of the NAC and NAP proteins, for example, measuring protein:protein binding, protein degradation or apoptotic activity can be employed in bioassays described herein to identify agents as agonists or antagonists of NAC proteins. As described herein, NAC proteins have the ability to self-associate. Thus, methods for identifying effective agents that alter the association of a NAC protein NAP will also be useful for identifying effective agents that alter the ability of NAC to self-associate. Similarly, CARD-X proteins have the ability to interact with other CARD-containing proteins and to self-associate. Thus, methods for identifying effective agents that alter the association of a NAC and another protein will also be useful for identifying effective agents that alter the ability of CARD-X to self-associate or to associate with a heterologous CARD-containing protein.

As used herein, "conditions that allow said NAC and NAP proteins to associate" refers to environmental conditions in which NAC:NAP specifically associate. Such conditions will typically be aqueous conditions, with a pH between 3.0 and 11.0, and temperature below 100° C. Preferably, the conditions will be aqueous conditions with salt concentrations below the equivalent of 1 M NaCl, and pH between 5.0 and 9.0, and temperatures between 0° C. and 50° C. Most preferably, the conditions will range from physiological conditions of normal yeast or mammalian cells, or conditions favorable for carrying out in vitro assays such as immunoprecipitation and GST-NAC:NAP association assays, and the like.

In yet another embodiment of the present invention, there are provided methods for modulating the caspase modulating activity mediated by NAC proteins, the method comprising:

contacting an NAC protein with an effective, modulating amount of an agonist or antagonist identified by the above-described bioassays.

The present invention also provides in vitro screening assays. Such screening assays are particularly useful in that they can be automated, which allows for high through-put screening, for example, of randomly or rationally designed agents such as drugs, peptidomimetics or peptides in order to identify those agents that effectively alter the association of NAC and NAP proteins or the activity of a NAC and, thereby, modulate apoptosis. An in vitro screening assay can utilize, for example, a NAC or a NAC fusion protein such as a NAC-glutathione-S-transferase fusion protein (GST/NAC; see Examples). For use in the in vitro screening assay, the NAC or NAC fusion protein should have an affinity for a solid substrate as well as the ability to associate with a NAC-associated protein. For example, when a NAC is used in the assay, the solid substrate can contain a covalently attached anti-NAC antibody. Alternatively, a GST/NAC fusion protein can be used in the assay and the solid substrate can contain covalently attached glutathione, which is bound by the GST component of the GST/NAC fusion protein. Similarly, a NAC-associated protein, or a GST/CARD-containing protein or GST/NB-ARC-containing protein fusion protein can be used in an in vitro assay as described herein.

An in vitro screening assay can be performed by allowing a NAC or NAC-fusion protein, for example, to bind to the solid support, then adding a NAC-associated protein and an agent to be tested. Control reactions, which do not contain an agent, can be performed in parallel. Following incubation under suitable conditions, which include, for example, an appropriate buffer concentration and pH and time and temperature that permit binding of the particular NAC and NAC-associated protein, the amount of protein that has associated in the absence of an agent and in the presence of an agent can be determined. The association of a NAC-associated protein with a NAC protein can be detected, for example, by attaching a detectable moiety such as a radionuclide or a fluorescent label to a NAC-associated protein and measuring the amount of label that is associated with the solid support, wherein the amount of label detected indicates the amount of association of the NAC-associated protein with a NAC protein. An effective agent is determined by comparing the amount of specific binding in the presence of an agent as compared to the control level of binding, wherein an effective agent alters the association of NAC with the NAC-assocated protein. Such an assay is particularly useful for screening a panel of agents such as a peptide library in order to detect an effective agent.

The invention further provides methods for introducing a nucleic acid encoding a NAC into a cell in a subject, for example, for gene therapy. Viruses are specialized infectious agents that can elude host defense mechanisms and can infect and propagate in specific cell types. Viral based systems provide the advantage of being able to introduce relatively high levels of the heterologous nucleic acid into a variety of cells. Suitable viral vectors for introducing invention nucleic acid encoding an NAC protein into mammalian cells (e.g., vascular tissue segments) are well known in the art. These viral vectors include, for example, Herpes simplex virus vectors (e.g., Geller et al., *Science*, 241:1667–1669 (1988)), Vaccinia virus vectors (e.g., Piccini et al., *Meth. in Enzymology*, 153:545–563 (1987); Cytomegalovirus vectors (Mocarski et al., in *Viral Vectors*, Y. Gluzman and S. H. Hughes, Eds., Cold Spring Harbor Laboratory, Cold Spring Harbor, N.Y., 1988, pp. 78–84), Moloney murine leukemia virus vectors (Danos et al., *Proc. Natl. Acad. Sci., USA*, 85:6469 (1980)), adenovirus vectors (e.g., Logan et al., *Proc. Natl. Acad. Sci., USA*, 81:3655–3659 (1984); Jones et al., *Cell*, 17:683–689 (1979); Berkner, *Biotechniques*, 6:616–626 (1988); Cotten et al., *Proc. Natl. Acad. Sci., USA*, 89:6094–6098 (1992); Graham et al., *Meth. Mol. Biol.*, 7:109–127 (1991)), adeno-associated virus vectors, retrovirus vectors (see, e.g., U.S. Pat. Nos. 4,405,712 and 4,650, 764), and the like. Especially preferred viral vectors are the adenovirus and retroviral vectors.

Suitable retroviral vectors for use herein are described, for example, in U.S. Pat. No. 5,252,479, and in WIPO publications WO 92/07573, WO 90/06997, WO 89/05345, WO 92/05266 and WO 92/14829, incorporated herein by reference, which provide a description of methods for efficiently introducing nucleic acids into human cells using such retroviral vectors. Other retroviral vectors include, for example, the mouse mammary tumor virus vectors (e.g., Shackleford et al., *Proc. Natl. Acad. Sci. USA*, 85:9655–9659 (1988)), and the like.

In particular, the specificity of viral vectors for particular cell types can be utilized to target predetermined cell types. Thus, the selection of a viral vector will depend, in part, on the cell type to be targeted. For example, if a neurodegenerative disease is to be treated by increasing the level of a NAC in neuronal cells affected by the disease, then a viral vector that targets neuronal cells can be used. A vector derived from a herpes simplex virus is an example of a viral vector that targets neuronal cells (Battleman et al., J. Neurosci. 13:941–951 (1993), which is incorporated herein by reference). Similarly, if a disease or pathological condition of the hematopoietic system is to be treated, then a viral vector that is specific for a particular blood cell or its precursor cell can be used. A vector based on a human immunodeficiency virus is an example of such a viral vector (Carroll et al., J. Cell. Biochem. 17E:241 (1993), which is incorporated herein by reference). In addition, a viral vector or other vector can be constructed to express a nucleic acid encoding a NAC in a tissue specific manner by incorporating a tissue-specific promoter or enhancer into the vector (Dai et al., *Proc. Natl. Acad. Sci. USA* 89:10892–10895 (1992), which is incorporated herein by reference).

For gene therapy, a vector containing a nucleic acid encoding a NAC or an antisense nucleotide sequence can be administered to a subject by various methods. For example, if viral vectors are used, administration can take advantage of the target specificity of the vectors. In such cases, there in no need to administer the vector locally at the diseased site. However, local administration can be a particularly effective method of administering a nucleic acid encoding a NAC. In addition, administration can be via intravenous or subcutaneous injection into the subject. Following injection, the viral vectors will circulate until they recognize host cells with the appropriate target specificity for infection. Injection of viral vectors into the spinal fluid also can be an effective mode of administration, for example, in treating a neurodegenerative disease.

Receptor-mediated DNA delivery approaches also can be used to deliver a nucleic acid molecule encoding a NAC into cells in a tissue-specific manner using a tissue-specific ligand or an antibody that is non-covalently complexed with the nucleic acid molecule via a bridging molecule (Curiel et al., *Hum. Gene Ther.* 3:147–154 (1992); Wu and Wu, *J. Biol. Chem.* 262:4429–4432 (1987), each of which is incorporated herein by reference). Direct injection of a naked or a nucleic acid molecule encapsulated, for example, in cationic liposomes also can be used for stable gene transfer into non-dividing or dividing cells in vivo (Ulmer et al., Science 259:1745–1748 (1993), which is incorporated herein by reference). In addition, a nucleic acid molecule encoding a NAC can be transferred into a variety of tissues using the particle bombardment method (Williams et al., Proc. Natl. Acad. Sci. USA 88:2726–2730 (1991), which is incorporated herein by reference). Such nucleic acid molecules can be linked to the appropriate nucleotide sequences required for transcription and translation.

A particularly useful mode of administration of a nucleic acid encoding a NAC is by direct inoculation locally at the site of the disease or pathological condition. Local administration can be advantageous because there is no dilution effect and, therefore, the likelihood that a majority of the targeted cells will be contacted with the nucleic acid molecule is increased. Thus, local inoculation can alleviate the targeting requirement necessary with other forms of administration and, if desired, a vector that infects all cell types in the inoculated area can be used. If expression is desired in only a specific subset of cells within the inoculated area, then a promotor, an enhancer or other expression element specific for the desired subset of cells can be linked to the nucleic acid molecule. Vectors containing such nucleic acid molecules and regulatory elements can be viral vectors, viral genomes, plasmids, phagemids and the like. Transfection vehicles such as liposomes also can be used to introduce a non-viral vector into recipient cells. Such vehicles are well known in the art.

The present invention also provides therapeutic compositions useful for practicing the therapeutic methods described herein. Therapeutic compositions of the present invention, such as pharmaceutical compositions, contain a physiologically compatible carrier together with an invention NAC (or functional fragment thereof), a NAC modulating agent, such as a compound (agonist or antagonist) identified by the methods described herein, or an anti-NAC antibody, as described herein, dissolved or dispersed therein as an active ingredient. In a preferred embodiment, the therapeutic composition is not immunogenic when administered to a mammal or human patient for therapeutic purposes.

As used herein, the terms "pharmaceutically acceptable", "physiologically compatible" and grammatical variations thereof, as they refer to compositions, carriers, diluents and reagents, are used interchangeably and represent that the materials are capable of administration to a mammal without the production of undesirable physiological effects such as nausea, dizziness, gastric upset, and the like.

The preparation of a pharmacological composition that contains active ingredients dissolved or dispersed therein is well known in the art. Typically such compositions are prepared as injectables either as liquid solutions or suspensions; however, solid forms suitable for solution, or suspension, in liquid prior to use can also be prepared. The preparation can also be emulsified.

The active ingredient can be mixed with excipients which are pharmaceutically acceptable and compatible with the active ingredient in amounts suitable for use in the therapeutic methods described herein. Suitable excipients are, for example, water, saline, dextrose, glycerol, ethanol, or the like, as well as combinations of any two or more thereof. In addition, if desired, the composition can contain minor amounts of auxiliary substances such as wetting or emulsifying agents, pH buffering agents, and the like, which enhance the effectiveness of the active ingredient.

The therapeutic composition of the present invention can include pharmaceutically acceptable salts of the components therein. Pharmaceutically acceptable nontoxic salts include the acid addition salts (formed with the free amino groups of the polypeptide) that are formed with inorganic acids such as, for example, hydrochloric acid, hydrobromic acid, perchloric acid, nitric acid, thiocyanic acid, sulfuric acid, phosphoric acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, and the like.

Salts formed with the free carboxyl groups can also be derived from inorganic bases such as, for example, sodium hydroxide, ammonium hydroxide, potassium hydroxide, and the like; and organic bases such as mono-, di-, and tri-alkyl and -aryl amines (e.g., triethylamine, diisopropyl amine, methyl amine, dimethyl amine, and the like) and optionally substituted ethanolamines (e.g., ethanolamine, diethanolamine, and the like).

Physiologically tolerable carriers are well known in the art. Exemplary liquid carriers are sterile aqueous solutions that contain no materials in addition to the active ingredients and water, or contain a buffer such as sodium phosphate at physiological pH, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary additional liquid phases include glycerin, vegetable oils such as cottonseed oil, and water-oil emulsions.

As described herein, an "effective amount" is a predetermined amount calculated to achieve the desired therapeutic effect, e.g., to modulate the protein degradation activity of an invention NAC protein. The required dosage will vary with the particular treatment and with the duration of desired treatment; however, it is anticipated that dosages between about 10 micrograms and about 1 milligram per kilogram of body weight per day will be used for therapeutic treatment. It may be particularly advantageous to administer such compounds in depot or long-lasting form as discussed hereinafter. A therapeutically effective amount is typically an amount of an NAC-modulating agent or compound identified herein that, when administered in a physiologically acceptable composition, is sufficient to achieve a plasma concentration of from about 0.1 $\mu$g/ml to about 100 $\mu$g/ml, preferably from about 1.0 $\mu$g/ml to about 50 $\mu$g/ml, more preferably at least about 2 $\mu$g/ml and usually 5 to 10 $\mu$g/ml. Therapeutic invention anti-NAC antibodies can be administered in proportionately appropriate amounts in accordance with known practices in this art.

Also provided herein are methods of treating pathologies, said method comprising administering an effective amount of an invention therapeutic composition. Such compositions are typically administered in a physiologically compatible composition.

Exemplary diseases related to abnormal cell proliferation contemplated herein for treatment according to the present invention include cancer pathologies, keratinocyte hyperplasia, neoplasia, keloid, benign prostatic hypertrophy, inflammatory hyperplasia, fibrosis, smooth muscle cell proliferation in arteries following balloon angioplasty (restenosis), and the like. Exemplary cancer pathologies contemplated herein for treatment include, gliomas, carcinomas, adenocarcinomas, sarcomas, melanomas, hamartomas, leukemias, lymphomas, and the like.

Methods of treating pathologies of abnormal cell proliferation will include methods of modulating the activity of one or more oncogenic proteins, wherein the oncogenic proteins specifically interact with NAC. Methods of modulating the activity of such oncogenic proteins will include contacting the oncogenic protein with a substantially pure NAC or an active fragment (i.e., oncogenic protein-binding fragment) thereof. This contacting will modulate the activity of the oncogenic protein, thereby providing a method of treating a pathology caused by the oncogenic protein. Further methods of modulating the activity of oncogenic proteins will include contacting the oncogenic protein with an agent, wherein the agent modulates the interactions between NAC and the oncogenic protein.

Also contemplated herein, are therapeutic methods using invention pharmaceutical compositions for the treatment of pathological disorders in which there is too little cell division, such as, for example, bone marrow aplasias, immunodeficiencies due to a decreased number of lymphocytes, and the like. Methods of treating a variety of inflammatory diseases with invention therapeutic compositions are also contemplated herein, such as treatment of sepsis, fibrosis (e.g., scarring), arthritis, graft versus host disease, and the like.

The present invention also provides methods for diagnosing a pathology that is characterized by an increased or decreased level of apoptosis in a cell to determine whether the increased or decreased level of apoptosis is due, for example, to increased or decreased expression of a NAC in the cell or to expression of a variant NAC. The identification of such a pathology, which can be due to altered association of a NAC with a NAC-associated protein in a cell, can allow for intervention therapy using an effective agent or a nucleic acid molecule or an antisense nucleotide sequence as described above. In general, a test sample can be obtained from a subject having a pathology characterized by having or suspected of having increased or decreased apoptosis and can be compared to a control sample from a normal subject to determine whether a cell in the test sample has, for example, increased or decreased expression of NAC. The level of a NAC in a cell can be determined by contacting a sample with a reagent such as an anti-NAC antibody or a NAC-associated protein, either of which can specifically bind a NAC. For example, the level of a NAC in a cell can determined by well known immunoassay or immunohistochemical methods using an anti-NAC antibody (see, for example, Reed et al., supra, 1992; see, also, Harlow and Lane, supra, (1988)). As used herein, the term "reagent" means a chemical or biological molecule that can specifically bind to a NAC or to a bound NAC/NAC-associated protein complex. For example, either an anti-NAC antibody or a NAC-associated protein can be a reagent for a NAC, whereas either an anti-NAC antibody or an anti-NAC-associated protein antibody can be a reagent for a NAC/NAC-associated protein complex.

As used herein, the term "test sample" means a cell or tissue specimen that is obtained from a subject and is to be examined for expression of a NAC in a cell in the sample. A test sample can be obtained, for example, during surgery or by needle biopsy and can be examined using the methods described herein to diagnose a pathology characterized by increased or decreased apoptosis. Increased or decreased expression of a NAC in a cell in a test sample can be determined by comparison to an expected normal level for a NAC in a particular cell type. A normal range of NAC levels in various cell types can be determined by sampling a statistically significant number of normal subjects. In addition, a control sample can be evaluated in parallel with a test sample in order to determine whether a pathology characterized by increased or decreased apoptosis is due to increased or decreased expression of a NAC. The test sample can be examined using, for example, immunohistochemical methods as described above or the sample can be further processed and examined. For example, an extract of a test sample can be prepared and examined to determine whether a NAC that is expressed in a cell in the sample can associate with a NAC-associated protein in the same manner as a NAC from a control cell or whether, instead, a variant NAC is expressed in the cell.

In accordance with another embodiment of the present invention, there are provided diagnostic systems, preferably in kit form, comprising at least one invention nucleic acid encoding NAC, NAC protein, and/or anti-NAC antibody described herein, in a suitable packaging material. In one embodiment, for example, the diagnostic nucleic acids are derived from any of SEQ ID NOs:1, 3 and 5. Invention diagnostic systems are useful for assaying for the presence or absence of nucleic acid encoding NAC in either genomic DNA or in transcribed nucleic acid (such as mRNA or cDNA) encoding NAC.

A suitable diagnostic system includes at least one invention NAC nucleic acid, NAC protein, and/or anti-NAC antibody, preferably two or more invention nucleic acids, proteins and/or antibodies, as a separately packaged chemical reagent(s) in an amount sufficient for at least one assay. Instructions for use of the packaged reagent are also typically included. Those of skill in the art can readily incorporate invention nucleic probes and/or primers into kit form in combination with appropriate buffers and solutions for the practice of the invention methods as described herein.

As employed herein, the phrase "packaging material" refers to one or more physical structures used to house the contents of the kit, such as invention nucleic acid probes or primers, and the like. The packaging material is constructed by well known methods, preferably to provide a sterile, contaminant-free environment. The packaging material has a label which indicates that the invention nucleic acids can be used for detecting a particular sequence encoding NAC including the nucleotide sequences set forth in SEQ ID NOs:1, 3 and 5 or mutations or deletions therein, thereby diagnosing the presence of, or a predisposition for, cancer. In addition, the packaging material contains instructions indicating how the materials within the kit are employed both to detect a particular sequence and diagnose the presence of, or a predisposition for, cancer.

The packaging materials employed herein in relation to diagnostic systems are those customarily utilized in nucleic acid-based diagnostic systems. As used herein, the term "package" refers to a solid matrix or material such as glass, plastic, paper, foil, and the like, capable of holding within fixed limits an isolated nucleic acid, oligonucleotide, or primer of the present invention. Thus, for example, a package can be a glass vial used to contain milligram quantities of a contemplated nucleic acid, oligonucleotide or primer, or it can be a microtiter plate well to which microgram quantities of a contemplated nucleic acid probe have been operatively affixed.

"Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

A diagnostic assay should include a simple method for detecting the amount of a NAC in a sample that is bound to the reagent. Detection can be performed by labeling the reagent and detecting the presence of the label using well known methods (see, for example, Harlow and Lane, supra, 1988; chap. 9, for labeling an antibody). A reagent can be labeled with various detectable moieties including a radiolabel, an enzyme, biotin or a fluorochrome. Materials for labeling the reagent can be included in the diagnostic kit or can be purchased separately from a commercial source. Following contact of a labeled reagent with a test sample and, if desired, a control sample, specifically bound reagent can be identified by detecting the particular moiety.

A labeled antibody that can specifically bind the reagent also can be used to identify specific binding of an unlabeled reagent. For example, if the reagent is an anti-NAC antibody, a second antibody can be used to detect specific binding of the anti-NAC antibody. A second antibody generally will be specific for the particular class of the first antibody. For example, if an anti-NAC antibody is of the IgG class, a second antibody will be an anti-IgG antibody. Such second antibodies are readily available from commercial sources. The second antibody can be labeled using a detectable moiety as described above. When a sample is labeled using a second antibody, the sample is first contacted with a first antibody, then the sample is contacted with the labeled second antibody, which specifically binds to the first antibody and results in a labeled sample.

In accordance with another embodiment of the invention, a method is provided to identify NAC-associated proteins. As used herein, the term "NAC-associated protein" or "NAP" means a protein that can specifically bind to NAC or its alternative isoforms. Because NAC proteins are known to self-associate, NAC proteins are encompassed by the term NAP. An exemplary NAP is a protein or a polypeptide portion of a protein that can bind the NB-ARC, CARD, LRR, or TIM-Barrel-like domains of NAC. Similarly, the term "CARD-X Associated Protein" or "CAP" refers to a protein that can bind specifically to the CARD-X protein. Likewise, since CARD-X proteins are known to self-associate, CARD-X proteins are encompassed by the term CAP. A NAP or CAP can be identified, for example, using in vitro protein binding assays similar to those described in the Examples, by Yeast Two-Hybrid assays similar to those described in the Examples, or by other types of protein-interaction assays and methods.

Using NAC or CARD-X, it is clear to one skilled in the art of protein purification, protein interaction cloning, or protein mass-spectrometry, that NAPs or CAPs can be identified using the methods disclosed herein.

Although the term "NAP" or "CAP" is used generally, it should be recognized that a NAP or CAP that is identified using an assay described herein can be a portion of a protein, which is considered to be a candidate NAP or CAP. As used herein, the term "active fragment" of a NAP or CAP refers to a protein that corresponds to a polypeptide sequence that can bind NAC or CARD-X, respectively, but that consists of only a portion of the full length protein. Although such polypeptides are considered NAPs or CAPs, it is well known that a cDNA sequence obtained from a cDNA library may not encode the full length protein. Thus, a cDNA can encode a polypeptide that is only a portion of a full length protein but, nevertheless, assumes an appropriate conformation and contains a sufficient region so as to bind NAC or CARD-X. However, in the full length protein, the polypeptide can assume a conformation that does not bind NAC or CARD-X, due for example to steric blocking of the NAP or CAP binding site. Such a full length protein is also an example of a NAP or CAP, wherein NAC-binding or CARD-X-binding activity can be activated under the appropriate conditions (i.e., phosphorylation, proteolysis, protein binding, pH change, and the like). For convenience of discussion, the terms "NAP" and "CAP", as used herein, are intended to include a NAP or CAP, respectively, and active fragments thereof.

Since CARD-containing proteins are commonly involved in apoptosis, the association of a NAP or CAP with NAC or CARD-X can affect the level of apoptosis in a cell. The identification by use of the methods described herein of various NAPs or CAPs can provide the necessary insight into cell death or signal transduction pathways controlled by NAC or CARD-X, allowing for the development of assays that are useful for identifying agents that effectively alter the association of a NAP with NAC or a CAP with CARD-X. Such agents can be useful, for example, for providing effective therapy for a cancer in a subject or for treating an autoimmune disease. These same assays can be used for identification of agents that modulate the self-association of NAC via its CARD domain, NB-ARC domain, or other domains within this protein; and, they can be used for identification of agents that modulate the self-association of CARD-X with itself via its CARD domain or other domains found within this protein.

In a normal cell, a steady state level of association of NAP and NAC proteins likely occurs. This steady state level of association of NAP and NAC proteins in a particular cell type can determine the normal level of apoptosis in that cell type. An increase or decrease in the steady state level of association of NAP and NAC proteins in a cell can result in an increased or decreased level of apoptosis in the cell, which can result in a pathology in a subject. The normal association of NAP and NAC proteins in a cell can be altered due, for example, to the expression in the cell of a variant NAP or NAC protein, respectively, either of which can compete with the normal binding function of NAC and, therefore, can decrease the association of NAP and NAC proteins in a cell. The term "variant" is used generally herein to mean a protein that is different from the NAP or NAC protein that normally is found in a particular cell type. In addition, the normal association of NAP and NAC proteins in a cell can be increased or decreased due, for example, to contact of the cell with an agent such as a drug that can effectively alter the association of NAP and NAC proteins in a cell.

NB-ARC and CARD domain proteins of the invention, NACβ, NACγ and NACδ, were characterized, for example, using an in vitro binding assay and CARD-containing proteins were further characterized using the yeast two hybrid system. An in vivo transcription activation assay such as the yeast two hybrid system is particularly useful for identifying and manipulating the association of proteins. In addition, the results observed in such an assay likely mirror the events that naturally occur in a cell. Thus, the results obtained in such an in vivo assay can be predictive of results that can occur in a cell in a subject such as a human subject.

A transcription activation assay such as the yeast two hybrid system is based on the modular nature of transcription factors, which consist of functionally separable DNA-binding and trans-activation domains. When expressed as separate proteins, these two domains fail to mediate gene transcription. However, transcription activation activity can be restored if the DNA-binding domain and the trans-activation domain are bridged together due, for example, to the association of two proteins. The DNA-binding domain and trans-activation domain can be bridged, for example, by expressing the DNA-binding domain and trans-activation domain as fusion proteins (hybrids), provided that the proteins that are fused to the domains can associate with each other. The non-covalent bridging of the two hybrids brings the DNA-binding and trans-activation domains together and creates a transcriptionally competent complex. The association of the proteins is determined by observing transcriptional activation of a reporter gene (see Example I).

The yeast two hybrid systems exemplified herein use various strains of S. cerevisiae as host cells for vectors that express the hybrid proteins. A transcription activation assay also can be performed using, for example, mammalian cells. However, the yeast two hybrid system is particularly useful due to the ease of working with yeast and the speed with which the assay can be performed. For example, yeast host cells containing a lacZ reporter gene linked to a LexA operator sequence were used to demonstrate that the $CARD_L$ domain of NAC (amino acid residues 1128–1473 of SEQ ID NO:2) can interact with several CARD-containing proteins (see Examples). For example, in one case the DNA-binding domain consisted of the LexA DNA-binding domain, which binds the LexA promoter, fused to the $CARD_L$ domain of NAC and the trans-activation domain consisted of the B42 acidic region separately fused to several cDNA sequences which encoded CARD-containing proteins. When the LexA domain was non-covalently bridged to a trans-activation domain fused to a CARD-containing protein, the association activated transcription of the reporter gene.

A NAP, for example, a CARD-containing protein or an NB-ARC-containing protein also can be identified using an in vitro assay such as an assay utilizing, for example, a glutathione-S-transferase (GST) fusion protein as described in the Examples. Such an in vitro assay provides a simple, rapid and inexpensive method for identifying and isolating a NAP. Such an in vitro assay is particularly useful in confirming results obtained in vivo and can be used to characterize specific binding domains of a NAP. For example, a $GST/CARD_L$ fusion protein can be expressed and can be purified by binding to an affinity matrix containing immobilized glutathione. If desired, a sample that can contains a CARD-containing protein or active fragments of a CARD-containing protein can be passed over an affinity column containing bound $GST/CARD_L$ and a CARD-containing protein that binds to $CARD_L$ can be obtained. In addition, $GST/CARD_L$ can be used to screen a cDNA expression library, wherein binding of the $GST/CARD_L$ fusion protein to a clone indicates that the clone contains a cDNA encoding a CARD-containing protein.

In another embodiment of the invention, methods are provided for monitoring the progress of treatment for a pathology that is characterized by an increased or decreased level of apoptosis in a cell, which methods are useful to ascertain the feasability of such treatment. Monitoring such a therapy, such as, e.g., a therapy that alters association of a NAC with a NAC-associated protein in a cell using an effective agent, can allow for modifications in the therapy to be made, including decreasing the amount of effective agent used in therapy, increasing the amount of effective agent, or using a different effective agent. In general, a test sample can be obtained from a subject having a pathology characterized by increased or decreased apoptosis, which sample can be compared to a control sample from a normal subject to determine whether a cell in the test sample has, for example, increased or decreased expression of NAC. Preferably, this control sample is a previous sample from the same patient, thereby providing a direct comparison of changes to the pathology as a result of the therapy. The level of a NAC in a cell can be determined by contacting a sample with a reagent such as an anti-NAC antibody or a NAC-associated protein, either of which can specifically bind a NAC. For example, the level of a NAC in a cell can determined by well known immunoassay or immunohistochemical methods using an anti-NAC antibody (see, for example, Reed et al., supra, 1992; see, also, Harlow and Lane, supra, (1988)).

In accordance with another embodiment of the invention, there are provided methods for determining a prognosis of disease free or overall survival in a patient suffering from cancer. For example, it is contemplated herein that abnormal levels of NAC proteins (either higher or lower) in primary tumor tissue show a high correlation with either increased or decreased tumor recurrence or spread, and therefore indicates the likelihood of disease free or overall survival. Thus, the present invention advantageously provides a significant advancement in cancer management because early identification of patients at risk for tumor recurrence or spread will permit aggressive early treatment with significantly enhanced potential for survival. Also provided are methods for predicting the risk of tumor recurrence or spread in an individual having a cancer tumor; methods for screening a cancer patient to determine the risk of tumor metastasis; and methods for determining the proper course of treatment for a patient suffering from cancer. These methods are carried out by collecting a sample from a patient and comparing the level of NAC expression in the patient to the level of expression in a control or to a reference level of NAC expression as defined by patient population sampling, tissue culture analysis, or any other method known for determining reference levels for determination of disease prognosis. The level of NAC expression in the patient is then classified as higher than the reference level or lower than the reference level, wherein the prognosis of survival or tumor recurrence is different for patients with higher levels than the prognosis for patients with lower levels.

All U.S. patents and all publications mentioned herein are incorporated in their entirety by reference thereto. The invention will now be described in greater detail by reference to the following non-limiting examples.

EXAMPLES 1.0 cDNA Cloning

Figure 1B:
FIG. 1B shows multiple isoforms of NAC. Isoforms of NAC are generated by alternative mRNA splicing, based on cDNA cloning results. The same symbols as in FIG. 1A are used. Two alternatively spliced exons are shown as dotted boxes and hatched boxes, respectively. Note that longer and shorter versions of the CARD domain are produced ($CARD_L$ and $CARD_S$). The four resultant isoforms are described as NACα, NACβ, NACγ and NACδ.
Figure 1C:
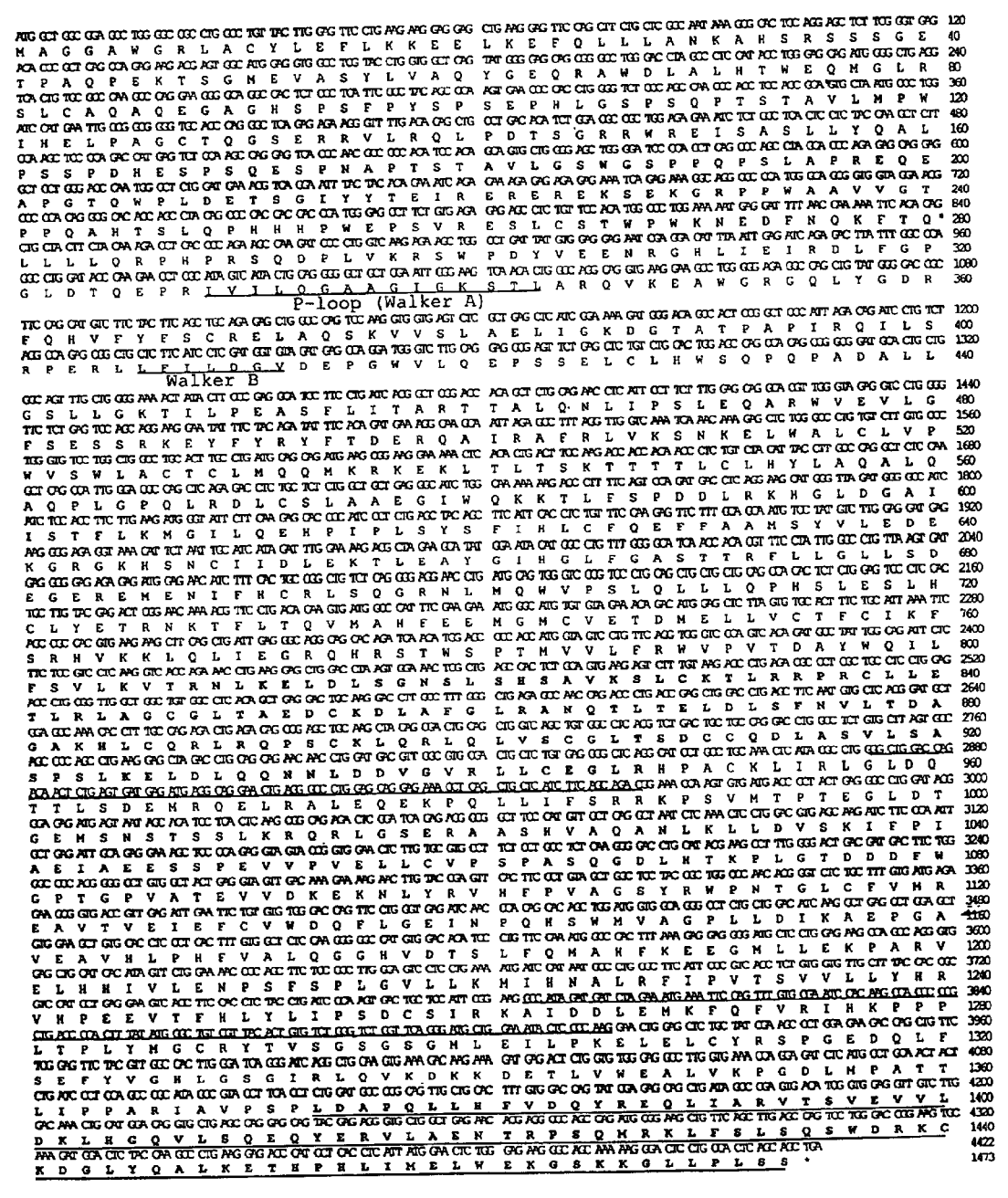

Jurkat total RNA was reverse-transcribed to complementary DNAs using MMLV reverse transcriptase (Stratagene) and random hexanucleotide primers. Three overlapping cDNA fragments of NAC were amplified from the Jurkat complementary DNAs with Turbo Pfu DNA polymerase (Stratagene) using the following oligonucleotide primer sets: primer set 1; 5'-CCGAATTCACCATGGCTGG CGGAGCCTGGGGC-3' (forward; SEQ ID NO:13) and 5'-CCGCTCGAGTCAACAGAGGGTTGTGGTGGTCTT G-3' (reverse; SEQ ID NO:14), primer set 2; 5'-CCCGAAT TCGAACCTCGCATAGTCATACTGC-3' (forward; SEQ ID NO:15) and 5'-GTCCCACAACAGAATTCAATCTCA ACGGTC-3' (reverse; SEQ ID NO:16), and primer set 3; 5'-TGTGATGAGAGAAGCGGTGAC-3' (forward; SEQ ID NO:17) and 5'-CCGCTCGAGCAAAGAAGGGTCAGCC AAAGC-3' (reverse; SEQ ID NO:18). The resultant cDNA fragments were ligated into mammalian expression vector pcDNA-myc (Invitrogen, modified as described in Roy et al., *EMBO J*. 16:6914–6925 (1997)) and assembled to full-length cDNA by ligating fragments 2 and 3 at the EcoRI site to make fragment 4, and by ligating fragments 1 and 4 at the Bst X1 site, as depicted in FIG. 1A. Sequencing analysis of the assembled full-length cDNA was carried out, and splice isoforms (shown as dotted and hatched regions in FIG. 1B) of NAC clones were identified. The full-length NAC nucleotide and protein sequences, including two alternatively spliced regions underlined (nucleotides 2870–2959 and 3784–3915 of SEQ ID NO:1, respectively), are presented in FIG. 1C. The full length nucleotide sequence of three of the isoforms is set forth in SEQ ID NOs:1, 3 and 5 corresponding to NACβ, NACγ and NACδ, respectively.

Comparison of NAC to known protein sequences using Clustal multiple sequence alignment (Thompson et al., Nucleic Acids Research 22:4673–4680 (1994)) revealed that the CARD domain of NAC (see, e.g., residues 1373 to 1473 of SEQ ID NO:2) is similar to numerous CARD domain proteins. Further sequence analysis predicted an $\alpha_8\beta_8$ (TIM)-Barrel-like domain similar to those observed in aldolase and RuBisCo in NAC, located on the immediate amino terminal side of the predicted CARD domain (see, e.g., residues 1079 to 1364 of SEQ ID NO:2). Additionally, a portion of NAC was found to have sequence portions homologous to NB-ARC domains (see, e.g., residues 329 to 547 of SEQ ID NO:2) and a leucine-rich repeat region (see, e.g., residues 808 to 947 of SEQ ID NO:2). Based on its homology to the above proteins the protein of the invention has been termed a NAC protein, as it is a NB-ARC and CARD domain containing protein. ClustalW multiple sequence alignment with other NB-ARC and CARD domain containing proteins confirmed the homology of NAC to other proteins in both the NB-ARC region (particularly in the P-loop, or Walker A, and Walker B portions) and CARD region (FIG. 1D and FIG. 1E, respectively). This sequence analysis represents the first time a domain resembling a TIM-barrel domain has been identified in a protein that also contains a CARD domain, and also the first time a domain resembling a TIM-barrel domain has been identified in a protein that also contains an NB-ARC domain.

2.0 Plasmid Constructions

Complementary DNA encoding the CARD domain of NAC was amplified from Jurkat cDNAs with Turbo Pfu DNA polymerase (Stratagene) and primer set 3 as described above. The resultant PCR fragments were digested with EcoRI and Xho I restriction enzymes and ligated into pGEX-4T1 (Pharmacia) and pcDNA-myc vectors. This region of NAC contains two alternatively spliced isoforms, termed $CARD_L$ (amino acid residues 1128–1473 of SEQ ID NO:2) and $CARD_S$ (amino acid residues 1128–1261 and 1306–1473 of SEQ ID NO:2). The region of cDNA encoding NB-ARC domain was PCR-amplified using primers SEQ ID NO:15 (forward) and SEQ ID NO:14 (reverse). The resultant PCR fragment was digested with EcoRI and Xho I restriction enzymes (yielding a fragment encoding amino acid residues 326–551 of SEQ ID NO:2) and ligated into a pGEX-4T1 and pcDNA-myc vectors.

3.0 In vitro Protein Binding Assays

NB-ARC, $CARD_L$, and $CARD_S$ in pGEX-4T1 were expressed in XL-1 blue *E. coli* cells (Stratagene), and affinity-purified using glutathione (GSH)-sepharose according to known methods, such as those in *Current Protocols in Molecular Biology*, Ausubel et al. eds., John Wiley and Sons (1999). For GST pull-down assays, purified $CARD_L$ and $CARD_S$ GST fusion proteins and GST alone (0.1–0.5 μg immobilized on 10–15 μl GSH-sepharose beads) were incubated with 1 mg/ml of BSA in 100 μl Co-IP buffer [142.4 mM KCl, 5 mM $MgCl_2$, 10 mM HEPES (pH 7.4), 0.5 mM EGTA, 0.2% NP-40, 1 mM DTT, and 1 mM PMSF] for 30 min. at room temperature. The beads were then incubated with 1 μl of rat reticulocyte lysates (TnT-lysate; Promega, Inc.) containing $^{35}$S-labeled, in vitro translated $CARD_L$, $CARD_S$, or control protein Skp-1 in 100 μl Co-IP buffer supplemented with 0.5 mg/ml BSA for overnight at 4° C. The beads were washed four times in 500 μl Co-IP buffer, followed by boiling in 20 μl Laemmli-SDS sample buffer. The eluted proteins were analyzed by SDS-PAGE. The bands of SDS-PAGE gels were detected by fluorography.

Figure 2A:
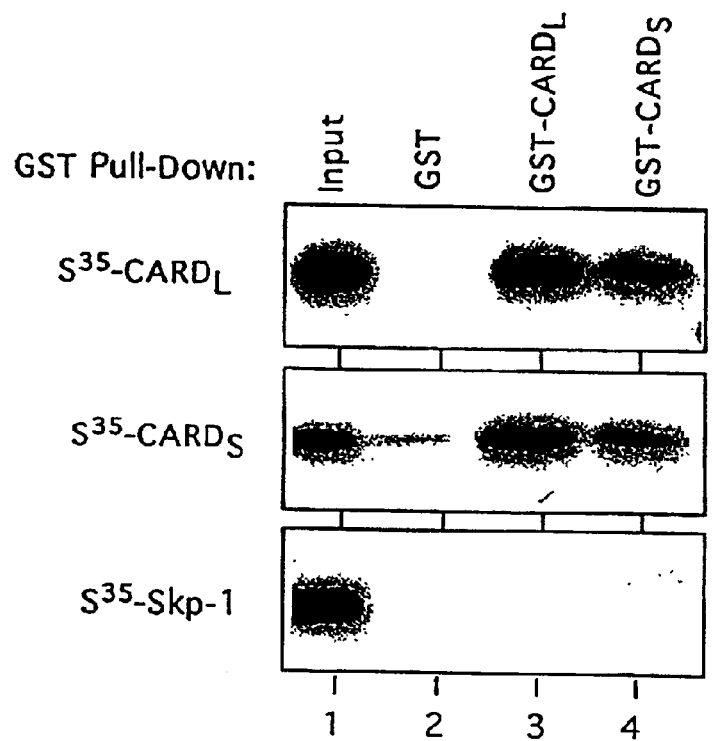
FIGS. 2(A+B) shows self-association of Long and Short CARD domains of NAC. (A) For in vitro binding assays, purified GST fusion proteins immobilized on GSH-sepharose containing $CARD_L$ (lane 3), $CARD_S$ (lane 4), or GST alone (lane 2) were incubated with $^{35}$S-labeled, in vitro translated $CARD_L$ (top panel), $CARD_S$ (middle panel), or control protein Skp-1 (bottom panel). In vitro translation mix (one tenth of input, lane 1) was directly loaded as control. (B) Homophilic interactions of CARD. In vitro translated Apaf-1 (-WD) (top panel), CED4 (middle panel), or control Skp-1 (bottom panel) proteins were incubated with GST (lane 2), GST-$CARD_L$ (lane 3), and GST-$CARD_S$ (lane 4) immobilized on GSH-sepharose beads. In lane 1, one tenth of input $^{35}$S proteins are shown.

The resultant homodimerization pattern reveals that $CARD_L$-$CARD_L$, $CARD_S$-$CARD_S$, and both $CARD_L$-$CARD_S$ containing lanes have very strong signals, whereas lanes containing control GST alone and control Skp-1 have negligible signals (FIG. 2A). Thus, CARD domains of the invention NAC show a very strong ability to self-associate in vitro.

Figure 2B:
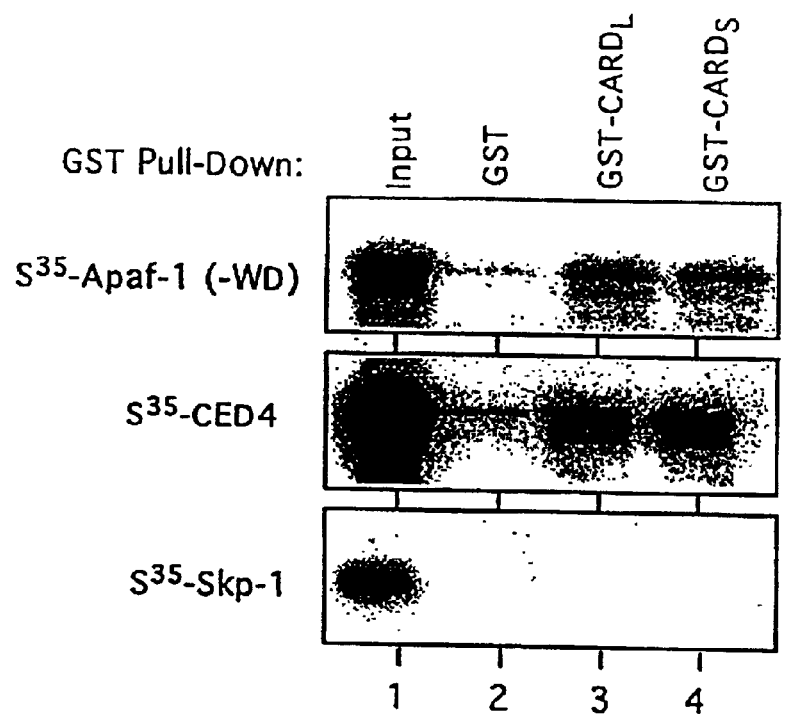

In vitro translated Apaf-1 (lacking its WD domain), CED4, and control Skp-1 proteins were subjected to GST pull-down assay using GSH-sepharose beads conjugated with GST, GST-CARD$_L$, and GST-CARD$_S$ as described above. Both lanes containing GST-CARD$_S$ and lanes containing GST-CARD$_L$ yielded very strong signals when incubated with either Apaf-1 (-WD) or CED4, whereas, the controls GST alone and Skp-1 again yielded negligible signals (FIG. 2B). Thus, in addition to self-association, CARD domains of the invention NAC demonstrate the ability to in vitro associate with other CARD-containing proteins.

4.0 Protein Interaction Studies in Yeast

EGY48 yeast cells (*Saccharomyces cerevisiae*: MATα, trpl, ura3, his, leu2::plexApo6-leu2) were transformed with pGilda-CARD$_L$ plasmids (his marker) encoding the LexA DNA binding domain fused to: CARD domains of NAC (CARD$_L$) and caspase-9; pro-caspase-8; Apaf-1 without its WD domain; Bcl-XL, Bax and Bcl-2 without transmembrane domains. EGY48 were also transformed with vector pJG4-5 (trpl marker) encoding the above listed group of proteins and additionally vRas and FADD as target proteins, fused to B42 transactivation domain, and the cells were transformed with a LexA-LacZ reporter plasmid pSH1840 (ura3 marker,), as previously described (Durfee et al., 1993; Sato et al., 1995). Sources for cells and plasmids were described previously in U.S. Pat. No. 5,632,994, and in Zervous et al., *Cell* 72:223–232 (1993); Gyuris et al., *Cell* 75:791–803 (1993); Golemis et al., In *Current Protocols in Molecular Biology* (ed. Ausubel et al.; Green Publ.; N.Y. 1994), each of which is incorporated herein by reference. Transformants were replica-plated on Burkholder's minimal medium (BMM) plates supplemented with leucine and 2% glucose as previously described (Sato et al., *Gene* 140:291–292 (1994)). Protein-protein interactions were scored by growth of transformants on leucine deficient BMM plates containing 2% galactose and 1% raffinose.

Protein-protein interactions were also evaluated using β-galactosidase activity assays. Colonies grown on BMM/Leu/Glucose plates were filter-lifted onto nitrocellulose membranes, and incubated over-night on BMM/Leu/galactose plates. Yeast cells were lysed by soaking filters in liquid nitrogen and thawing at room temperature. β-galactosidase activity was measured by incubating the filter in 3.2 ml Z buffer (60 mM, Na$_2$HPO$_4$, 40 mM Na$_2$HPO$_4$, 10 mM KCl, 1 mM MgSO$_4$) supplemented with 50 μl X-gal solution (20 mg/ml). Levels of β-galactosidase activity were scaled according to the intensity of blue color generated for each transformant.

The results of this experiment showed colonies on leucine deficient plates for yeast containing NAC-CARD$_L$/LexA fusions together with caspase-9/B42, Apaf-1/B42, and Bax/B42 fusions (FIG. 3). In addition, the NAC-CARD$_L$/LexA:caspase-9/B42 and NAC-CARD$_L$/LexA:Apaf-1/B42 cells had significant amounts of LacZ activity. The cells containing the complementary fusions caspase-9/LexA:NAC-CARD$_L$/B42 and Apaf-1/LexA:NAC-CARD$_L$/B42 also grew on leucine deficient plates and showed significant LacZ activity. Thus all four indicators of protein-:protein interaction confirmed that the CARD$_L$ domain of NAC interacts with the CARD domains of caspase-9 and with Apaf-1. Partial indication of the protein:protein interactions with NAC-CARD$_L$ were observed for Bax, caspase-8, Bcl-XL and Bcl-2, suggesting that a broad range of CARD domain proteins also interact with the CARD domain of NAC.

Similar two-hybrid interaction experiments have been performed using the CARD domain of the CARD-X protein. Table I summarizes the results of the two-hybrid experiments wherein a fusion protein containing the DNA-binding domain of the LexA protein expressed from the pGilda plasmid and a CARD domain from CARD-X or several other CARD-containing proteins, including CARDIAK, NAC (CARD$_L$), Apaf-1, caspases-2, 9, and 11, were expressed in the sames cells as CARD domains from CARD-X, CARDIAK, NAC(CARD$_L$), caspase-9 and cIAP-2, expressed as fusion proteins with a transactivation domain from the B42 protein from the pJG4-5 plasmid, as described above. As shown, the CARD domain of CARD-X interacted with itself but not with the CARD domains of other proteins.

TABLE I

Yeast Two Hybrid Analysis of CARD-X:CARD interactions

|    | pGilda              | pJG4-5         | Results |
|----|---------------------|----------------|---------|
| 1  | CARD-X CARD         | CARD-X-CARD    | +++     |
| 2  | CARD-X CARD         | CARDIAK        | –       |
| 3  | CARD-X CARD         | NAC-CARD$_L$   | –       |
| 4  | CARD-X CARD         | Caspase-9 CARD | –       |
| 5  | CARD-X CARD         | cIAP-2         | –       |
| 6  | CARDIAK             | CARD-X CARD    | –       |
| 7  | NAC-CARD$_L$        | CARD-X CARD    | –       |
| 8  | APAF C3 + C4        | CARD-X CARD    | –       |
| 9  | Caspase-2           | CARD-X CARD    | –       |
| 10 | Caspase-11          | CARD-X CARD    | –       |
| 11 | Caspase 9-C-terminus| CARD-X CARD    | –       |
| 12 | CARDIAK             | CARDIAK        | ++++    |

5.0 Self-Association of NB-ARC Domain of NAC

Figure 4:
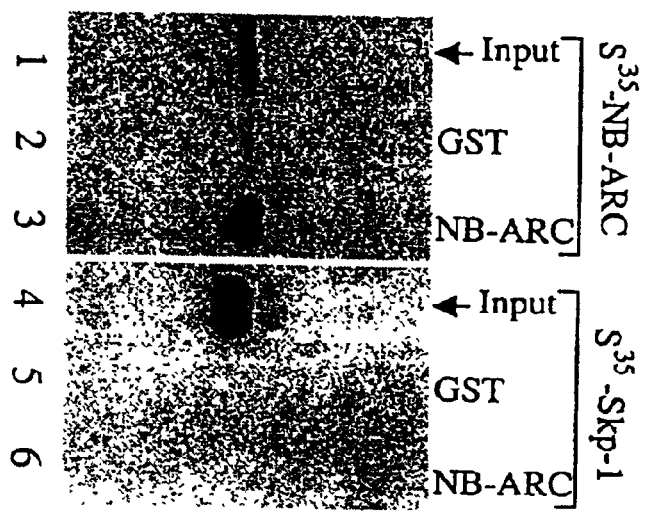
FIG. 4 shows self-association of NB-ARC domain of NAC. In vitro translated, $^{35}$S-labeled rat reticulocyte lysates (1 μl) containing NB-ARC (lanes 2 and 3) or Skp-1 (as a control; lanes 5 and 6) were incubated with purified GST-NB-ARC (lanes 3 and 6) or GST alone (lanes 2 and 5) immobilized on GSH-sepharose beads for in vitro binding assays. In lanes 1 and 4, one tenth of input $^{35}$S proteins are shown.

In vitro translated, $^{35}$S-labeled rat reticulocyte lysates (1 μl) containing NB-ARC or Skp-1 (used as a control) were incubated with GSH-sepharose beads conjugated with purified GST-NB-ARC or GST alone for GST pull-down assay, resolved on SDS-PAGE and visualized by fluorography as described above. One tenth of input were loaded for NB-ARC or Skp-1 as controls. In this assay, the NB-ARC-containing fragment of NAC demonstrates a strong ability to homodimerize (FIG. 4).

The ability to self-associate and to bind other known CARD domains establishes the CARD domains of NAC, CARD$_S$ and CARD$_L$, as capable of the same protein-protein interactions observed in other known CARD domains. The ability of CARD-X to self-associate also establishes this protein as having the same protein-protein interaction properties of known CARD proteins. Thus two isoforms of a new human CARD domain have been characterized, and a highly related sequence of another human protein CARD-X has also been characterized. In addition, the ability of the putative NB-ARC domain of NAC has been shown to both self-associate, establishing this domain as capable of the same protein-protein interactions observed in other known NB-ARC domains. Therefore, the NAC protein has been demonstrated to contain both a functional CARD domain and a functional NB-ARC domain.

6.0 Protein-Protein Interactions of NAC

Transient transfection of 293T, a human embryonic kidney fibroblast cell line, were conducted using SuperFect reagents (Qiagen) according to manufacturer's instructions. The cDNA fragments encoding full-length CED4 and the truncated form of Apaf-1 (Apaf-1ΔWD) comprising amino acids 1–420 of the human Apaf-1 protein were amplified by PCR and subcloned into pcDNA3HA at EcoRI and Xho I sites. Expression plasmids encoding catalytically inactive forms of pro-Casp8 [pro-Casp8 (C/A)] was prepared by replacing Cys 377 with an Ala using site-directed mutagenesis and pro-Casp9 [pro-Casp9 (C/A)] has been described previously, Cardone et al., *Science* 282:1318–1321 (1998)).

293T cells were transiently transfected with an expression plasmid (2 μg) encoding HA-tagged human Apaf-1ΔWD, CED4, pro-Casp8 (C/A) or C-Terminal Flag-tagged pro-Casp9 (C/A) in the presence or absence of a plasmid (2 μg) encoding myc-tagged NAC (encoding amino acid residues 1–1261 and 1306–1473 of SEQ ID NO:2). After 24 hr growth in culture, transfected cells were collected and lysed in Co-IP buffer [142.4 mM KCl, 5 mM $MgCl_2$, 10 mM HEPES (pH 7.4), 0.5 mM EGTA, 0.1% NP-40, and 1 mM DTT] supplemented with 12.5 mM β-glycerolphosphate, 2 mM NaF, 1 mM $Na_3VO_4$, 1 mM PMSF, and 1× protenase inhibitor mix (Boehringer Mannheim). Cell lysates were clarified by microcentrifugation and subjected to immuno-precipitation using either a mouse monoclonal antibody to myc (Santa Cruz Biotechnologies, Inc) or a control mouse IgG. Proteins from the immune complexes were resolved by SDS-PAGE, transferred to nitrocellulose membranes, and subjected to immunoblot analysis using anti-HA antibodies followed by anti-myc antibodies using a standard Western blotting procedure and ECL reagents from Amersham-Pharmacia Biotechnologies, Inc. (Krajewski et al., *Proc. Natl. Acad. Sci. USA* 96:5752–5757 (1999)).

Figure 6A:
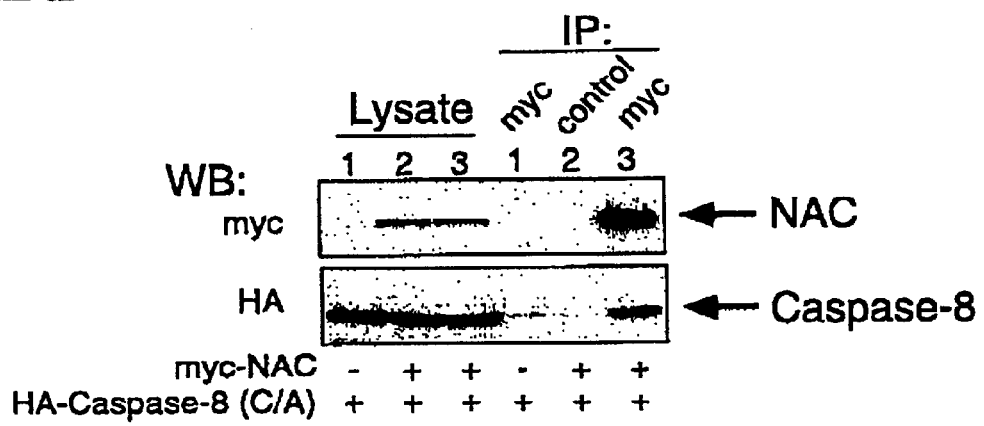
FIGS. 6(A+B) shows that NAC interacts with pro-Casp8, but not pro-Casp9. (A) Interaction with pro-Casp8. 293T cells were transfected with an expression plasmid encoding HA-tagged human pro-Casp8 [HA-Casp8 (C/A)], which harbors an alanine replacement of the catalytic cysteine residue, in the presence (lanes 2 and 3) or absence (lane 1) of myc-NAC expression plasmid. Transfected cells were lysed and subjected to immunoprecipitation (IP) with either anti-myc antibodies (lanes 1 and 3) or a control antibody (lane 2). The immunoprecipitated proteins were resolved by SDS-PAGE, transferred to nitrocellulose, and analyzed by immunoblotting (WB) for pro-Casp8 (bottom panel) using anti-HA antibodies or for NAC (top panel) using anti-myc antibodies. One tenth of the total cell lysates of each transfection was loaded directly in gels as a control (Lysate). (B) Interaction with pro-Casp9. Identical procedures and conditions described for Casp8 were used for Casp9 interaction studies with NAC. The Casp9 expression plasmid [Flag-Casp9 (C/A)] contains a C-terminal Flag-tagged form of pro-Casp9 harboring an alanine replacement of the catalytic cysteine residue. The immunoblots were probed for Casp9 (bottom panel) using a rabbit anti-Casp9 polyclonal antibody derived against GST-Casp9 fusion proteins.
Figure 6B:
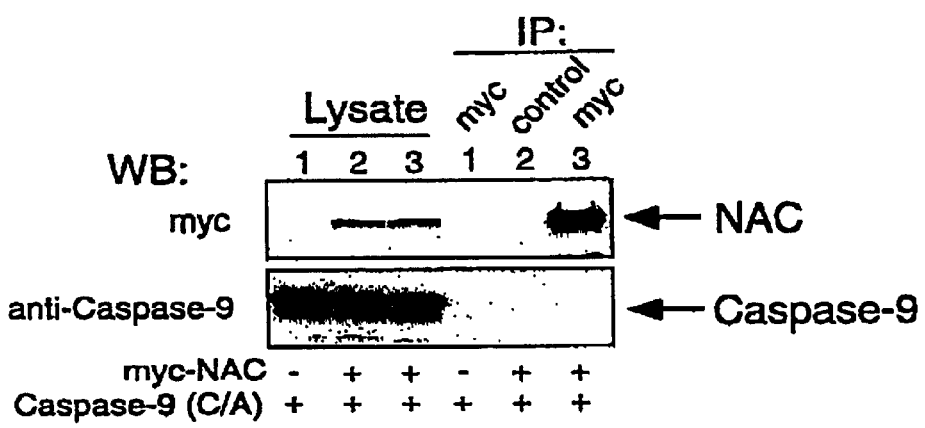

The results show that NAC of the invention interacts with other NB-ARC and CARD-containing proteins, Apaf-1 (FIG. 5A) and CED-4 (FIG. 5B), and additionally with caspase-8 (FIG. 6A), but not with caspase-9 (FIG. 6B). This is in contrast with the observed interaction between caspase-9 and the $CARD_L$ domain of NAC from the above described yeast two-hybrid assay. This may be due to the regulation of the full-length NAC in terms of its ability to interact with pro-caspase-9 such that NAC is in either a latent (off) or active (on) conformation, analogous to Apaf-1 which binds pro-caspase-9 only when cytochrome c is produced to induce a conformational change in Apaf-1. As with NAC, if only the CARD domain of Apaf-1 is expressed, it will bind to pro-caspase-9 independently of the coactivator, cytochrome c (Qin et al., *Nature* 399:549–557 (1999)).

Although the invention has been described with reference to the examples above, it should be understood that various modifications can be made without departing from the spirit of the invention. Accordingly, the invention is limited only by the following claims.

---

That which is claimed is:

1. An isolated nucleic acid molecule encoding a NB-ARC and CARD containing protein (NAC), comprising a nucleotide sequence encoding a polypeptide having at least 80% identity to SEQ ID NO:4 or SEQ ID NO:6, or the complement of said nucleotide sequence,
   wherein said polypeptide forms a CARD domain fold,
   wherein said polypeptide comprises an NB-ARC domain capable of associating with the NB-ARC domain of SEQ ID NO:2,
   wherein said polypeptide does not comprise amino acids 957–987 of SEQ ID NO:2, and
   wherein said polypeptide associates with SEQ ID NO:2 or with Apaf-1.

2. An isolated nucleic acid molecule encoding a NAC, comprising a nucleotide sequence encoding a polypeptide having at least 80% identity to SEQ ID NO:2, or the complement of said nucleotide sequence,
   wherein said polypeptide comprises amino acids 1262–1305 of SEQ ID NO:2,
   wherein said polypeptide forms a CARD domain fold,
   wherein said polypeptide comprises an NB-ARC domain capable of associating with the NB-ARC domain of SEQ ID NO:2, and
   wherein said polypeptide associates with SEQ ID NO:2 or with Apaf-1.

3. The nucleic acid molecule of either claim 1 or claim 2, wherein said nucleic acid molecule is cDNA.

4. A vector containing the nucleic acid molecule of either claim 1 or claim 2.

5. Recombinant cells containing the nucleic acid molecule of either claim 1 or claim 2.

6. An oligonucleotide comprising a nucleotide sequence consisting of nucleotides 985–1641 of SEQ ID NO:1 or its complement, or a fragment thereof consisting of at least 500 contiguous nucleotides therefrom, and a nucleotide sequence at the 5' or 3' end that differs from SEQ ID NO:1 or its compliment.

7. An oligonucleotide comprising a nucleotide sequence consisting of nucleotides 2422–2844 of SEQ ID NO:1 or its complement, and a nucleotide sequence at the 5' or 3' end that differs from SEQ ID NO:1 or its compliment.

8. An oligonucleotide comprising a nucleotide sequence consisting of nucleotides 3235–3960 of SEQ ID NO:1 or its complement, and a nucleotide sequence at the 5' or 3' end that differs from SEQ ID NO:1 or its compliment.

9. An oligonucleotide comprising a nucleotide sequence consisting of nucleotides 2870–2959 of SEQ ID NO:1 or its complement, and a nucleotide sequence at the 5' or 3' end that differs from SEQ ID NO:1 or its compliment.

10. An oligonucleotide comprising a nucleotide sequence consisting of nucleotides 4117–4419 of SEQ ID NO:1 or its complement, and a nucleotide sequence at the 5' or 3' end that differs from SEQ ID NO:1 or its compliment.

11. An oligonucleotide comprising at least 100 contiguous nucleotide of the nucleotide set forth as nucleotides 3784–3915 of SEQ ID NO:1 or its compliment.

12. An oligonucleotide comprising at least 500 contiguous nucleotides up to 1035 contiguous nucleotides of the nucleotide sequence set forth in any of SEQ ID Nos: 1, 3 and 5 or the complement of said nucleotide sequence, and a nucleotide sequence at the 5' or 3' end that differs from the nucleotide sequence set forth in any of SEQ ID Nos: 1, 3 and 5 or the compliment of said nucleotide sequence.

13. The oligonucleotide of any one of claims 6, 7, 8, 9, 10, or 11, wherein said oligonucleotide is labeled with a detectable marker.

14. A kit for detecting the presence of a NAC nucleotide sequence comprising at least one oligonucleotide according to claim 13.

15. A method for expression of a NAC protein, said method comprising culturing cells of claim 5 under conditions suitable for expression of said NAC.

16. A method for identifying a nucleic acid molecule encoding a mammalian NAC, said method comprising:
   contacting a sample containing nucleic acid molecule with the oligonucleotide according to any one of claims 6, 7, 8, 9, 10, or 11, wherein said contacting is effected under high stringency hybridization conditions, and identifying a nucleic acid molecule that hybridize thereto, wherein said nucleic acid molecule encodes a mammalian NAC polypeptide that associates with SEQ ID NO:2 or with Apaf-1.

17. A functional fragment of the nucleic acid molecule of either claim 1 or claim 2, wherein said functional fragment comprises a nucleotide sequence encoding a CARD domain corresponding to amino acids 1128–1261 and 1036–1473 of SEQ ID NO:2, and wherein said functional fragment associates with SEQ ID NO:2 or with Apaf-1.

18. The nucleic acid molecule of claim 1, comprising a nucleotide sequence encoding a polypeptide having at least 95% identity to SEQ ID NO:4 or 6.

19. The nucleic acid molecule of claim 1, comprising a nucleotide sequence encoding amino acids 1128–1261 and 1306–1473 of SEQ ID NO:2.

20. The nucleic acid molecule of claim 1, comprising a nucleotide sequence encoding amino acids 329–547 of SEQ ID NO:2.

21. An isolated nucleic acid molecule encoding a NB-ARC and CARD containing protein (NAC), comprising a nucleotide sequence set forth in any of SEQ ID NOs:3 or 5.

22. An isolated nucleic acid molecule encoding a NB-ARC and CARD containing protein (NAC), comprising a nucleotide sequence set forth in any of SEQ ID NO:4 or 6.

23. The nucleic acid molecule of claim 2, comprising a nucleotide sequence encoding a polypeptide having at least 95% identity to SEQ ID NO:2.

24. The nucleic acid molecule of claim 2, comprising a nucleotide sequence encoding amino acids 1128–1261 and 1306–1473 of SEQ ID NO:2.

25. The nucleic acid molecule of claim 2, comprising a nucleotide sequence encoding amino acids 329–547 of SEQ ID NO:2.

26. An isolated nucleic acid molecule encoding a NB-ARC and CARD containing protein (NAC), comprising a nucleotide sequence set forth in any of SEQ ID NO:2.

27. The nucleic acid molecule of claim 2, wherein the nucleotide sequence of nucleic acid molecule is the same as that set forth in SEQ ID NO:1.

28. A functional fragment of the nucleic acid molecule of either claim 1 or claim 2, wherein said functional fragment comprises a nucleotide sequence encoding a NB-ARC domain corresponding to amino acids 329–547 of SEQ ID NO:2, and wherein said functional fragment associates with SEQ ID NO:2.

29. An oligonucleotide of claim 11, comprising at least 200 contiguous nucleotides.

30. The nucleic acid molecule of claim 21, wherein said nucleic acid molecule is cDNA.

31. A vector containing the nucleic acid molecule of claim 30.

32. Recombinant cells containing the nucleic acid molecule of claim 21.

33. A method for expression of a NAC protein, said method comprising culturing cells of claim 32 under conditions suitable for expression of said NAC.

34. The nucleic acid molecule of claim 22 or 26, wherein said nucleic acid molecule is cDNA.

35. A vector containing the nucleic acid molecule of claim 34.

36. Recombinant cells containing the nucleic acid molecule of claim 34.

37. A method for expression of a NAC protein, said method comprising culturing cells of claim 36 under conditions suitable for expression of said NAC.

38. A functional fragment of an isolated nucleic acid molecule encoding a NB-ARC and CARD containing protein (NAC), comprising a nucleotide sequence set forth in either of SEQ ID NOs:3 or 5, wherein said functional fragment comprises a nucleotide sequence encoding a CARD domain corresponding to amino acids 1128–1261 and 1036–1473 of SEQ ID NO:2, and wherein said functional fragment associates with SEQ ID NO:2 or with Apaf-1.

39. An oligonucleotide consisting of the nucleotide sequence set forth as nucleotides 985–1641 of SEQ ID NO:1 or its complement, or a fragment thereof consisting of at least 500 contiguous nucleotides therefrom.

40. An oligonucleotide consisting of the nucleotide sequence set forth as nucleotides 2422–2844 of SEQ ID NO:1 or its complement.

41. An oligonucleotide consisting of the nucleotide sequence set forth as nucleotides 3235–3960 of SEQ ID NO:1 or its complement.

42. An oligonucleotide consisting of the nucleotide sequence set forth as nucleotides 2870–2959 of SEQ ID NO:1 or its complement.

43. An oligonucleotide consisting of the nucleotide sequence set forth as nucleotides 4117–4419 of SEQ ID NO:1 or its complement.

44. An oligonucleotide comprising a nucleotide sequence consisting of nucleotides 2422–2844 of SEQ ID NO:1 or its complement, or a fragment thereof consisting of at least 30 contiguous nucleotides therefrom, and a nucleotide sequence at the 5' or 3' end that differs from SEQ ID NO:1 or its compliment.

* * * * *

UNITED STATES PATENT AND TRADEMARK OFFICE
CERTIFICATE OF CORRECTION

PATENT NO. : 6,818,750 B2
DATED : November 16, 2004
INVENTOR(S) : Reed, John C.

It is certified that error appears in the above-identified patent and that said Letters Patent is hereby corrected as shown below:

Column 141,
Line 9, please delete "complement, and a nucleotide sequence at the 5' or 3' end" and replace therefore with -- complement, or a fragment thereof consisting of at least 20 contiguous nucleotides therefrom, and a nucleotide sequence at the 5' or 3' end --.
Line 25, please delete "of the nucleotide set forth as nucleotides" and replace therefore with -- of the nucleotide sequence set forth as nucleotides".
Line 27, please delete "oligonucleotide comprising at least 500 contiguous" and replace therefore with -- oligonucleotide consisting of at least 500 contiguous --.
Line 35, please delete "or 11, wherein" and replace therefore with -- 11, or 12, wherein --
Line 56, please delete "corresponding to amino acids 1128-1261 and 1036-1473 of SEQ ID NO:2," and replace therefore with -- corresponding to amino acids 1373-1473 of SEQ ID NO:2, --.

Column 142,
Line 23, please delete "nucleotide sequence of nucleic acid molecule is the same as" and replace therefore with -- nucleotide sequence of said nucleic acid molecule is the same as --
Line 58, please delete "and 1036-1473 of SEQ ID NO:2," and replace therefore with -- and 1306 -1473 of SEQ ID NO:2, --

Signed and Sealed this

Twenty-ninth Day of March, 2005

JON W. DUDAS
*Director of the United States Patent and Trademark Office*